(12) United States Patent
Wolf et al.

(10) Patent No.: US 10,555,963 B2
(45) Date of Patent: *Feb. 11, 2020

(54) KLOTHO PROTEIN AND RELATED COMPOUNDS FOR THE TREATMENT AND DIAGNOSIS OF CANCER

(75) Inventors: Ido Wolf, Or Yehuda (IL); Tamar Rubinek, Or Yehuda (IL); Bella Kaufman, Kiryat Ono (IL); Lilach Abramovitch, Kfar Saba (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 1498 days.

This patent is subject to a terminal disclaimer.

(21) Appl. No.: 13/429,383

(22) Filed: Mar. 25, 2012

(65) Prior Publication Data

US 2012/0178699 A1  Jul. 12, 2012

Related U.S. Application Data

(63) Continuation-in-part of application No. 12/598,963, filed as application No. PCT/IL2008/000618 on May 6, 2008, now abandoned.

(60) Provisional application No. 61/042,918, filed on Apr. 7, 2008, provisional application No. 60/916,787, filed on May 8, 2007.

(30) Foreign Application Priority Data

May 8, 2007  (WO) .................. PCT/IL2008/000618

(51) Int. Cl.
*A61K 31/7088* (2006.01)
*A61K 38/47* (2006.01)

(52) U.S. Cl.
CPC .......... *A61K 31/7088* (2013.01); *A61K 38/47* (2013.01)

(58) Field of Classification Search
None
See application file for complete search history.

(56) References Cited

U.S. PATENT DOCUMENTS

| | | |
|---|---|---|
| 6,136,780 A | 10/2000 | Zagon et al. |
| 6,342,506 B1 | 1/2002 | Giovanella et al. |
| 6,624,170 B2 | 9/2003 | Giovanella et al. |
| 6,696,423 B1 | 2/2004 | Barsoum et al. |
| 6,737,397 B1 | 5/2004 | Zagon et al. |
| RE39,337 E | 10/2006 | Monosov et al. |
| 7,268,120 B1 | 9/2007 | Horton et al. |
| 7,569,706 B2 | 8/2009 | Nemoto et al. |
| 2005/0208015 A1* | 9/2005 | Nemoto et al. ............ 424/85.1 |

FOREIGN PATENT DOCUMENTS

| | | |
|---|---|---|
| EP | 0945506 B1 | 2/2007 |
| WO | WO 00/27885 * | 5/2000 |
| WO | 01/20031 A | 3/2001 |
| WO | 2004100976 A1 | 11/2004 |

OTHER PUBLICATIONS

Machine translation of WO 00/27885 downloaded from JPO dated Apr. 15, 2013.*
Klotho Expression in Epithelial Ovarian Cancer and its Association with Insulin-Like Growth Factors and Disease Progression, Lu, L. et al., Cancer Investigation, 26:2, 185-192, Dec. 20, 2007 1532-4192.
Wang, Klotho, The Long Sought-After Elixir and A Novel Tumor Suppressor?, Cancer Biology and Therapy, Jan. 2006, pp. 20-21, vol. 5, No. 1, Landes Bioscience.
International Report on Patentability dated Nov. 10, 2009 in corresponding International Application No. PCT/IL2008/000618.
Shiraki-Iida et al., Structure of the mouse klotho gene and its two transcripts encoding membrane and secreted protein. Febs Lett. Mar. 6, 1998;424(1-2):6-10.
Spector et al., Activation of AMP-activated protein kinase by human EGF receptor 2/EGF receptor tyrosine kinase inhibitor protects cardiac cells. Proc Natl Acad Sci USA Jun. 19, 2007;104(25):10607-10612.
Tachimori et al., Combination Therapy of S-1 with Selective Cyclooxygenase-2 Inhibitor for Liver Metastasis of Colorectal Carcinoma. Anticancer Res. Mar.-Apr. 2008;28(2A):629-638.
Troiani et al., The use of xenograft models for the selection of cancer treatments with the EGFR as an example. Crit Rev Oncol Hematol. Mar. 2008;65(3):200-211.
Tuomela et al., Alendronate decreases orthotopic PC-3 prostate tumor growth and metastasis to prostate-draining lymph nodes in nude mice. BMC Cancer. Mar. 28, 2008;8:81(12 pages).
Urakawa et al., Klotho converts canonical FGF receptor into a specific receptor for FGF23. Nature. Dec. 7, 2006;444 (7120):770-774.
Utsugi et al., Decreased Insulin Production and Increased Insulin Sensitivity in the Klotho Mutant Mouse, a Novel Animal Model for Human Aging. Metabolism. Sep. 2000;49(9):1118-1123.
van Weerden et al., Use of Nude Mouse Xenograft Models in Prostate Cancer Research. Prostate. Jun. 1, 2000;43 (4):263-271.
Wang and Sun, Current understanding of klotho. Ageing Res Rev. Jan. 2009;8(1):43-51.
Wang, Klotho, The Long Sought-After Elixir and A Novel Tumor Suppressor? Cancer Biol Ther. Jan. 2006;5(1):20-21.
Wolf et al., 15-Hydroxyprostaglandin Dehydrogenase Is a Tumor Suppressor of Human Breast Cancer. Cancer Res. Aug. 1, 2006;66(15):7818-7823.

(Continued)

*Primary Examiner* — Addison D Ault
(74) *Attorney, Agent, or Firm* — JMB Davis Ben-David

(57) ABSTRACT

Disclosed is the use of a klotho protein or related compounds (especially KL1 or KL1 analogue) for treatment, and especially treatment of cancer, alone or together with other active pharmaceutical ingredients such as chemotherapeutic agents.

8 Claims, 19 Drawing Sheets

Specification includes a Sequence Listing.

(56) References Cited

OTHER PUBLICATIONS

Wolf et al., Association between diabetes mellitus and adverse characteristics of breast cancer at presentation. Eur J Cancer. May 2006;42(8):1077-1082.
Wolf et al., FOXA1: Growth inhibitor and a favorable prognostic factor in human breast cancer. Int J Cancer. Mar. 1, 2007;120(5):1013-1022.
Yamamoto et al., Regulation of Oxidative Stress by the Anti-aging Hormone Klotho. J Biol Chem. Nov. 11, 2005;280 (45):38029-38034.
Yee, Targeting insulin-like growth factor pathways. Br J Cancer. Feb. 27, 2006;94(4):465-468.
Zarrabeitia et al., Klotho Gene Polymorphism and Male Bone Mass. Calcif Tissue Int. Jan. 2007;80(1):10-14.
Abramovitz et al., KL1 internal repeat mediates klotho tumor suppressor activities and inhibits bFGF and IGF-1 in signaling pancreatic cancer. Clin Cancer Res. Jul. 1, 2011;17(13):4254-4266.
Arap et al., Cancer Treatment by Targeted Drug Delivery to Tumor Vasculature in a Mouse Model. Science. Jan. 16, 1998;279(5349):377-380.
Arking et al., Association of human aging with a functional variant of klotho. Proc Natl Acad Sci USA. Jan. 22, 2002;99(2):856-861.
Arking et al., KLOTHO Allele Status and the Risk of Early-Onset Occult Coronary Artery Disease. Am J Hum Genet. May 2003;72(5):1154-1161.
Bartucci et al., Differential Insulin-like Growth Factor I Receptor Signaling and Function in Estrogen Receptor (ER)- positive MCF-7 and ER-negative MDA-MB-231 Breast Cancer Cells. Cancer Res. Sep. 15, 2001;61(18):6747-6754.
Beck and Reichert, Therapeutic Fc-fusion proteins and peptides as successful alternatives to antibodies. MAbs. Sep.-Oct. 2011;3(5):415-416.
Bergmann et al., Insulin-like Growth Factor I Overexpression in Human Pancreatic Cancer: Evidence for Autocrine and Paracrine Roles. Cancer Res. May 15, 1995;55(10):2007-2011.
Cha et al., Removal of sialic acid involving Klotho causes cell-surface retention of TRPV5 channel via binding to galectin-1. Proc Natl Acad Sci U S A. Jul. 15, 2008;105(28):9805-9810 plus supporting information pp. 1-6.
Chen et al., Insulin stimulates the cleavage and release of the extracellular domain of Klotho by ADAM10 and ADAM17. Proc Natl Acad Sci USA. Dec. 11, 2007;104(50):19796-19801.
Chihara et al., Klotho Protein Promotes Adipocyte Differentiation. Endocrinology. Aug. 2006;147(8):3835-3842.
de Oliveira, Klotho RNAi induces premature senescence of human cells via a p53/p21 dependent pathway. FEBS Lett. Oct. 16, 2006;580(24):5753-5758.
Edderkaoui et al., Insulin-like Growth Factor-I Receptor Mediates the Prosurvival Effect of Fibronectin. J Biol Chem. Sep. 14, 2007;282(37):26646-26655.
El-Shewy et al., The Insulin-like growth factor type 1 and insulin-like growth factor type 2/mannose-6-phosphate receptors independently regulate ERK1/2 activity in HEK293 cells. J Biol Chem. Sep. 7, 2007;282(36):26150-26157.
Geier et al., Insulin-like Growth Factor-I Inhibits Cell Death Induced by Anticancer Drugs in the MCF-7 Cells: Involvement of Growth Factors in Drug Resistance. Cancer Invest. 1995;13(5):480-486.
Gery et al., Down-Regulation and Growth Inhibitory Role of C/EBPalpha in Breast Cancer. Clin Cancer Res. May 1, 2005;11(9):3184-3190.
Gillet et al., The Development of Gene Therapy: From Monogenic Recessive Disorders to Complex Diseases Such as Cancer. Methods Mol Biol. 2009;542:5-54.
Gomis et al., C/EBPβ at the core of the TGFβ cytostatic response and its evasion in metastatic breast cancer cells. Cancer Cell. Sep. 2006;10(3):203-214.
Gura, Systems for Identifying New Drugs Are Often Faulty. Science. Nov. 7, 1997;278(5340):1041-1042.
Haimsohn et al., Aurintricarboxylic Acid Induces a Distinct Activation of the IGF-I Receptor Signaling within MDA-231 Cells. Endocrinology. Mar. 2002;143(3):837-845.
Haluska et al., In vitro and In vivo Antitumor Effects of the Dual Insulin-Like Growth Factor-I/Insulin Receptor Inhibitor, BMS-554417. Cancer Res. Jan. 1, 2006;66(1):362-371.
Honors and Kinzig, The role of insulin resistance in the development of muscle wasting during cancer cachexia. J Cachexia Sarcopenia Muscle. Mar. 2012;3(1):5-11.
Huang, Regulation of ion channels by secreted Klotho: mechanisms and implications. Kidney Int. May 2010;77 (10):855-860.
Ikushima et al., Anti-apoptotic and anti-senescence effects of Klotho on vascular endothelial cells. Biochem Biophys Res Commun. Jan. 20, 2006;339(3):827-832.
Imura et al., Secreted Klotho protein in sera and CSF: implication for post-translational cleavage in release of Klotho protein from cell membrane. FEBS Lett. May 7, 2004;565(1-3):143-147.
Imura et al., α-Klotho as a Regulator of Calcium Homeostasis. Science. Jun. 15, 2007;316(5831):1615-1618.
International Search Report dated May 9, 2008 in corresponding International Application No. PCT/IL2008/000618.
International Preliminary Report on Patentability dated Nov. 10, 2009 in corresponding International Application No. PCT/IL2008/000618.
Ito et al., Molecular cloning and expression analyses of mouse [beta ]klotho, which encodes a novel Klotho family protein. Mech Dev. Nov. 2000;98(1-2):115-119.
Karna et al.. Serum and tissue level of insulin-like growth factor-I (IGF-I) and IGF-I binding proteins as an index of pancreatitis and pancreatic cancer. Int J Exp Pathol. Oct. 2002;83(5):239-45.
Kato et al., Establishment of the Anti-Klotho Monoclonal Antibodies and Detection of Klotho Protein in Kidneys. Biochem Biophys Res Commun. Jan. 19, 2000;267(2):597-602.
Kim et al., Klotho is a genetic risk factor for ischemic stroke caused by cardioembolism in Korean females. Neurosci Lett. Oct. 30, 2006;407(3):189-194.
Kuro-O et al., Mutation of the mouse klotho gene leads to a syndrome resembling ageing. Nature. Nov. 6, 1997;390 (6655):45-51.
Kurosu et al., Regulation of Fibroblast Growth Factor-23 Signaling by Klotho. J Biol Chem. Mar. 10, 2006;281 (10):6120-6123.
Kurosu et al., Suppression of Aging in Mice by the Hormone Klotho. Science. Sep. 16, 2005;309(5742):1829-1833 plus supplemental material accessed Dec. 18, 2014:1-16.
Lacroix and Leclercq, Relevance of breast cancer cell lines as models for breast tumours: an update. Breast Cancer Res Treat. Feb. 2004;83(3):249-289.
Li et al., Role of cdk2 in the sequential phosphorylation/activation of C/EBPγ during adipocyte differentiation. Proc Natl Acad Sci USA Jul. 10, 2007;104(28):11597-11602.
Liu et al., Klotho suppresses RIG-I-mediated senescence-associated inflammation. Nat Cell Biol. Mar. 2011;13 (3):254-262.
Lorenzi et al., Evidence against a direct role of klotho in insulin resistance. Pflugers Arch. Feb. 2010;459(3):465-473.
Lu et al., Klotho Expression in Epithelial Ovarian Cancer and its Association with Insulin-Like Growth Factors and Disease Progression. Cancer Invest. Mar. 2008;26(2):185-192.
Masiakos et al., Human Ovarian Cancer, Cell Lines, and Primary Ascites Cells Express the Human Mullerian Inhibiting Substance (MIS) Type II Receptor, Bind, and Are Responsive to MIS. Clin Cancer Res. Nov. 1999;5 (11):3488-3499.
Matsumura et al., Identification of the Human Klotho Gene and Its Two Transcripts Encoding Membrane and Secreted Klotho Protein. Biochem Biophys Res Commun. Jan. 26, 1998;242(3):626-630.
McElroy et al., Fluorescent LYVE-1 antibody to image lymphatic trafficking of cancer cells. J Surg Res. Jan. 2009;151(1):68-73.
Mitsiades et al., Inhibition of the insulin-like growth factor receptor-1 tyrosine kinase activity as a therapeutic strategy for multiple myeloma, other hematologic malignancies, and solid tumors. Cancer Cell. Mar. 2004;5(3):221-230.
Molta, Etanercept in Biologics in General Medicine. Boehncke et al., Springer-Verlag Berlin Heidelberg, 2007; Chap 4:32-41.
Nabeshima and Imura, α-Klotho: A Regulator That Integrates Calcium Homeostasis. Am J Nephrol. 2008;28 (3):455-464.

(56) References Cited

OTHER PUBLICATIONS

Noro et al., Gefitinib (IRESSA) sensitive lung cancer cell lines show phosphorylation of AKT without ligand stimulation. BMC Cancer. Dec. 6, 2006;6:277 (12 pages).

Ohyama et al., Molecular Cloning of Rat klotho cDNA: Markedly Decreased Expression of klotho by Acute Inflammatory Stress. Biochem Biophys Res Commun. Oct. 29, 1998;251(3):920-925.

Osterberg and Green, Guidance for Industry and Reviewers: Estimating the Safe Starting Dose in Clinical Trials for Therapeutics in Adult Healthy Volunteers. Federal Register, Jan. 2003;88(11): 1-26 . Accessible on-line at http:/fwww_fda_gov/cder/guidance/index_htm or http:/fwww_fda_gov/ohrms/dockets/defaulthtm.

Ryan et al., Advances in PEGylation of Important Biotech Molecules: Delivery Aspects. Expert Opin Drug Deily. Apr. 2008;5(4):371-383.

Schlachterman et al., Combined Resveratrol, Quercetin, and Catechin Treatment Reduces Breast Tumor Growth in a Nude Mouse Model. Transl Oncol. Mar. 2008;1(1):19-27.

\* cited by examiner

| Treatment | control | hKL | hKL1 |
|---|---|---|---|
| N tumors (%) | 16 (100%) | 14 (88%) | 12 (75%) |
| Tumor weight (mg ± SD) | 513 ± 304 | 226 ± 201 | 127 ± 93 |

```
                          SEQUENCE LISTING

<160> NUMBER OF SEQ ID NOS: 18

<210> SEQ ID NO 1
<211> LENGTH: 1012
<212> TYPE: PRT
<213> ORGANISM: homo sapiens
<300> PUBLICATION INFORMATION:
<302> TITLE: Polypeptide, Novel DNA and novel antibody
<308> DATABASE ACCESSION NUMBER: AAQ41828
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(1012)

<400> SEQUENCE: 1

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
```

```
                    245                 250                 255
Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670
```

```
Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
        690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Gly Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
        850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys  Lys Gly Arg
        995                 1000                1005

Arg Ser  Tyr Lys
    1010

<210> SEQ ID NO 2
<211> LENGTH: 549
<212> TYPE: PRT
<213> ORGANISM: homo sapiens
<300> PUBLICATION INFORMATION:
<302> TITLE: Polypeptide, novel DNA and novel antibody
<308> DATABASE ACCESSION NUMBER: AAQ41829
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(549)
```

<400> SEQUENCE: 2

Met Pro Ala Ser Ala Pro Pro Arg Arg Pro Pro Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly

```
                    405                 410                 415
Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
                435                 440                 445

Gly Val Asp Val Ile Gly Tyr Thr Ala Trp Ser Leu Met Asp Gly Phe
            450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
            515                 520                 525

Asp Asn Tyr Ile Gln Val Ser Gln Leu Thr Lys Pro Ile Ser Ser Leu
530                 535                 540

Thr Lys Pro Tyr His
545

<210> SEQ ID NO 3
<211> LENGTH: 1014
<212> TYPE: PRT
<213> ORGANISM: Mus musculus
<300> PUBLICATION INFORMATION:
<302> TITLE: Polypeptide, novel DNA and novel antibody
<308> DATABASE ACCESSION NUMBER: AAQ41830
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(1014)

<400> SEQUENCE: 3

Met Leu Ala Arg Ala Pro Pro Arg Arg Pro Pro Arg Leu Val Leu Leu
1               5                   10                  15

Arg Leu Leu Leu Leu His Leu Leu Leu Ala Leu Arg Ala Arg Cys
                20                  25                  30

Leu Ser Ala Glu Pro Gly Gln Gly Ala Gln Thr Trp Ala Arg Phe Ala
                35                  40                  45

Arg Ala Pro Ala Pro Glu Ala Ala Gly Leu Leu His Asp Thr Phe Pro
            50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
                100                 105                 110

Ser Gly Ala Pro Ser Pro Pro Leu Ser Ser Thr Gly Asp Val Ala Ser
            115                 120                 125

Asp Ser Tyr Asn Asn Val Tyr Arg Asp Thr Glu Gly Leu Arg Glu Leu
130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
                180                 185                 190
```

-continued

```
Leu Tyr His Trp Asp Leu Pro Gln Arg Leu Gln Asp Thr Tyr Gly Gly
            195                 200                 205

Trp Ala Asn Arg Ala Leu Ala Asp His Phe Arg Asp Tyr Ala Glu Leu
    210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
    290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
        355                 360                 365

Phe Ala Leu Ser Phe Gly Pro Thr Leu Ser Phe Gln Leu Leu Asp Pro
    370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
            420                 425                 430

Met Tyr Tyr Leu Lys Lys Phe Ile Met Glu Thr Leu Lys Ala Ile Arg
        435                 440                 445

Leu Asp Gly Val Asp Val Ile Gly Tyr Thr Ala Trp Ser Leu Met Asp
    450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
            500                 505                 510

Glu Asn Gln Pro Leu Glu Gly Thr Phe Pro Cys Asp Phe Ala Trp Gly
        515                 520                 525

Val Val Asp Asn Tyr Val Gln Val Asp Thr Thr Leu Ser Gln Phe Thr
    530                 535                 540

Asp Pro Asn Val Tyr Leu Trp Asp Val His His Ser Lys Arg Leu Ile
545                 550                 555                 560

Lys Val Asp Gly Val Val Ala Lys Lys Arg Lys Pro Tyr Cys Val Asp
                565                 570                 575

Phe Ser Ala Ile Arg Pro Gln Ile Thr Leu Leu Arg Glu Met Arg Val
            580                 585                 590

Thr His Phe Arg Phe Ser Leu Asp Trp Ala Leu Ile Leu Pro Leu Gly
        595                 600                 605
```

```
Asn Gln Thr Gln Val Asn His Thr Val Leu His Phe Tyr Arg Cys Met
    610             615             620
Ile Ser Glu Leu Val His Ala Asn Ile Thr Pro Val Ala Leu Trp
625             630             635             640
Gln Pro Ala Ala Pro His Gln Gly Leu Pro His Ala Leu Ala Lys His
                645             650             655
Gly Ala Trp Glu Asn Pro His Thr Ala Leu Ala Phe Ala Asp Tyr Ala
            660             665             670
Asn Leu Cys Phe Lys Glu Leu Gly His Trp Val Asn Leu Trp Ile Thr
            675             680             685
Met Asn Glu Pro Asn Thr Arg Asn Met Thr Tyr Arg Ala Gly His His
690             695             700
Leu Leu Arg Ala His Ala Leu Ala Trp His Leu Tyr Asp Asp Lys Phe
705             710             715             720
Arg Ala Ala Gln Lys Gly Lys Ile Ser Ile Ala Leu Gln Ala Asp Trp
                725             730             735
Ile Glu Pro Ala Cys Pro Phe Ser Gln Asn Asp Lys Glu Val Ala Glu
            740             745             750
Arg Val Leu Glu Phe Asp Ile Gly Trp Leu Ala Glu Pro Ile Phe Gly
            755             760             765
Ser Gly Asp Tyr Pro Arg Val Met Arg Asp Trp Leu Asn Gln Lys Asn
770             775             780
Asn Phe Leu Leu Pro Tyr Phe Thr Glu Asp Glu Lys Lys Leu Val Arg
785             790             795             800
Gly Ser Phe Asp Phe Leu Ala Val Ser His Tyr Thr Thr Ile Leu Val
                805             810             815
Asp Trp Glu Lys Glu Asp Pro Met Lys Tyr Asn Asp Tyr Leu Glu Val
            820             825             830
Gln Glu Met Thr Asp Ile Thr Trp Leu Asn Ser Pro Ser Gln Val Ala
            835             840             845
Val Val Pro Trp Gly Leu Arg Lys Val Leu Asn Trp Leu Arg Phe Lys
850             855             860
Tyr Gly Asp Leu Pro Met Tyr Val Thr Ala Asn Gly Ile Asp Asp Asp
865             870             875             880
Pro His Ala Glu Gln Asp Ser Leu Arg Ile Tyr Tyr Ile Lys Asn Tyr
                885             890             895
Val Asn Glu Ala Leu Lys Ala Tyr Val Leu Asp Asp Ile Asn Leu Cys
            900             905             910
Gly Tyr Phe Ala Tyr Ser Leu Ser Asp Arg Ser Ala Pro Lys Ser Gly
            915             920             925
Phe Tyr Arg Tyr Ala Ala Asn Gln Phe Glu Pro Lys Pro Ser Met Lys
930             935             940
His Tyr Arg Arg Ile Ile Asp Ser Asn Gly Phe Leu Gly Ser Gly Thr
945             950             955             960
Leu Gly Arg Phe Cys Pro Glu Glu Tyr Thr Val Cys Thr Glu Cys Gly
                965             970             975
Phe Phe Gln Thr Arg Lys Ser Leu Leu Val Phe Ile Ser Phe Leu Val
            980             985             990
Phe Thr Phe Ile Ile Ser Leu Ala  Leu Ile Phe His Tyr  Ser Lys Lys
            995             1000            1005
Gly Gln  Arg Ser Tyr Lys
   1010
```

-continued

```
<210> SEQ ID NO 4
<211> LENGTH: 550
<212> TYPE: PRT
<213> ORGANISM: Mus musculus
<300> PUBLICATION INFORMATION:
<302> TITLE: Polypeptide, novel DNA and novel antibody
<308> DATABASE ACCESSION NUMBER: AAQ41831
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(550)

<400> SEQUENCE: 4

Met Leu Ala Arg Ala Pro Pro Arg Arg Pro Arg Leu Val Leu Leu
1               5                   10                  15

Arg Leu Leu Leu Leu His Leu Leu Leu Ala Leu Arg Ala Arg Cys
                20                  25                  30

Leu Ser Ala Glu Pro Gly Gln Gly Ala Gln Thr Trp Ala Arg Phe Ala
                35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
                100                 105                 110

Ser Gly Ala Pro Ser Pro Pro Leu Ser Ser Thr Gly Asp Val Ala Ser
                115                 120                 125

Asp Ser Tyr Asn Asn Val Tyr Arg Asp Thr Glu Gly Leu Arg Glu Leu
            130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
                180                 185                 190

Leu Tyr His Trp Asp Leu Pro Gln Arg Leu Gln Asp Thr Tyr Gly Gly
            195                 200                 205

Trp Ala Asn Arg Ala Leu Ala Asp His Phe Arg Asp Tyr Ala Glu Leu
    210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
                260                 265                 270

Leu Leu Leu Ala His Ala Lys Val Trp His Leu Tyr Asn Thr Ser Phe
            275                 280                 285

Arg Pro Thr Gln Gly Gly Arg Val Ser Ile Ala Leu Ser Ser His Trp
    290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
                340                 345                 350
```

-continued

```
Asp Phe Thr Glu Ser Glu Lys Arg Leu Ile Arg Gly Thr Ala Asp Phe
        355                 360                 365

Phe Ala Leu Cys Phe Gly Pro Thr Leu Ser Phe Gln Leu Leu Asp Pro
    370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
            420                 425                 430

Met Tyr Tyr Leu Lys Lys Phe Ile Met Glu Thr Leu Lys Ala Ile Arg
                435                 440                 445

Leu Asp Gly Val Asp Val Ile Gly Tyr Thr Ala Trp Ser Leu Met Asp
            450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
                500                 505                 510

Glu Asn Gln Pro Leu Glu Gly Thr Phe Pro Cys Asp Phe Ala Trp Gly
            515                 520                 525

Val Val Asp Asn Tyr Val Gln Val Ser Pro Leu Thr Lys Pro Ser Val
            530                 535                 540

Gly Leu Leu Leu Pro His
545                 550

<210> SEQ ID NO 5
<211> LENGTH: 1015
<212> TYPE: PRT
<213> ORGANISM: homo sapiens
<300> PUBLICATION INFORMATION:
<302> TITLE: Polypeptide, novel DNA and novel antibody
<308> DATABASE ACCESSION NUMBER: AAQ41832
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(1015)

<400> SEQUENCE: 5

Met Ser Asn Gly Gly Leu Gln Arg Ser Val Ile Leu Ser Ala Leu Ile
1               5                   10                  15

Leu Leu Arg Ala Val Thr Gly Phe Ser Gly Asp Gly Arg Ala Ile Trp
            20                  25                  30

Ser Lys Asn Pro Asn Phe Thr Pro Val Asn Glu Ser Gln Leu Phe Leu
        35                  40                  45

Tyr Gly Thr Phe Pro Lys Asn Phe Phe Trp Gly Ile Gly Thr Gly Ala
    50                  55                  60

Leu Gln Val Glu Gly Ser Trp Lys Lys Asp Gly Lys Gly Pro Ser Ile
65                  70                  75                  80

Trp Asp His Phe Ile His Thr His Leu Lys Asn Val Ser Ser Thr Asn
                85                  90                  95

Gly Ser Ser Asp Ser Tyr Ile Phe Leu Glu Lys Asp Leu Ser Ala Leu
            100                 105                 110

Asp Phe Ile Gly Val Ser Phe Tyr Gln Phe Ser Ile Ser Trp Pro Arg
        115                 120                 125
```

```
Leu Phe Pro Asp Gly Ile Val Thr Val Ala Asn Ala Lys Gly Leu Gln
130                 135                 140

Tyr Tyr Ser Thr Leu Leu Asp Ala Leu Val Leu Arg Asn Ile Glu Pro
145                 150                 155                 160

Ile Val Thr Leu Tyr His Trp Asp Leu Pro Leu Ala Leu Gln Glu Lys
                165                 170                 175

Tyr Gly Gly Trp Lys Asn Asp Thr Ile Ile Asp Ile Phe Asn Asp Tyr
            180                 185                 190

Ala Thr Tyr Cys Phe Gln Met Phe Gly Asp Arg Val Lys Tyr Trp Ile
        195                 200                 205

Thr Ile His Asn Pro Tyr Leu Val Ala Trp His Gly Tyr Gly Thr Gly
210                 215                 220

Met His Ala Pro Gly Glu Lys Gly Asn Leu Ala Ala Val Tyr Thr Val
225                 230                 235                 240

Gly His Asn Leu Ile Lys Ala His Ser Lys Val Trp His Asn Tyr Asn
                245                 250                 255

Thr His Phe Arg Pro His Gln Lys Gly Trp Leu Ser Ile Thr Leu Gly
            260                 265                 270

Ser His Trp Ile Glu Pro Asn Arg Ser Glu Asn Thr Met Asp Ile Phe
        275                 280                 285

Lys Cys Gln Gln Ser Met Val Ser Val Leu Gly Trp Phe Ala Asn Pro
290                 295                 300

Ile His Gly Asp Gly Asp Tyr Pro Glu Gly Met Arg Lys Lys Leu Phe
305                 310                 315                 320

Ser Val Leu Pro Ile Phe Ser Glu Ala Glu Lys His Glu Met Arg Gly
                325                 330                 335

Thr Ala Asp Phe Phe Ala Phe Ser Phe Gly Pro Asn Asn Phe Lys Pro
            340                 345                 350

Leu Asn Thr Met Ala Lys Met Gly Gln Asn Val Ser Leu Asn Leu Arg
        355                 360                 365

Glu Ala Leu Asn Trp Ile Lys Leu Glu Tyr Asn Asn Pro Arg Ile Leu
370                 375                 380

Ile Ala Glu Asn Gly Trp Phe Thr Asp Ser Arg Val Lys Thr Glu Asp
385                 390                 395                 400

Thr Thr Ala Ile Tyr Met Met Lys Asn Phe Leu Ser Gln Val Leu Gln
                405                 410                 415

Ala Ile Arg Leu Asp Glu Ile Arg Val Phe Gly Tyr Thr Ala Trp Ser
            420                 425                 430

Leu Leu Asp Gly Phe Glu Trp Gln Asp Ala Tyr Thr Ile Arg Arg Gly
        435                 440                 445

Leu Phe Tyr Val Asp Phe Asn Ser Lys Gln Lys Glu Arg Lys Pro Lys
450                 455                 460

Ser Ser Ala His Tyr Tyr Lys Gln Ile Ile Arg Glu Asn Gly Phe Ser
465                 470                 475                 480

Leu Lys Glu Ser Thr Pro Asp Val Gln Gly Gln Phe Pro Cys Asp Phe
                485                 490                 495

Ser Trp Gly Val Thr Glu Ser Val Leu Lys Pro Glu Ser Val Ala Ser
            500                 505                 510

Ser Pro Gln Phe Ser Asp Pro His Leu Tyr Val Trp Asn Ala Thr Gly
        515                 520                 525

Asn Arg Leu Leu His Arg Val Glu Gly Val Arg Leu Lys Thr Arg Pro
530                 535                 540

Ala Gln Cys Thr Asp Phe Val Asn Ile Lys Lys Gln Leu Glu Met Leu
```

-continued

```
               545                 550                 555                 560
       Ala Arg Met Lys Val Thr His Tyr Arg Phe Ala Leu Asp Trp Ala Ser
                           565                 570                 575

Val Leu Pro Thr Gly Asn Leu Ser Ala Val Asn Arg Gln Ala Leu Arg
                           580                 585                 590

Tyr Tyr Arg Cys Val Val Ser Glu Gly Leu Lys Leu Gly Ile Ser Ala
                       595                 600                 605

Met Val Thr Leu Tyr Tyr Pro Thr His Ala His Leu Gly Leu Pro Glu
               610                 615                 620

Pro Leu His Ala Asp Gly Trp Leu Asn Pro Ser Thr Ala Glu Ala
       625                 630                 635                 640

Phe Gln Ala Tyr Ala Gly Leu Cys Phe Gln Glu Leu Gly Asp Leu Val
                           645                 650                 655

Lys Leu Trp Ile Thr Ile Asn Glu Pro Asn Arg Leu Ser Asp Ile Tyr
                           660                 665                 670

Asn Arg Ser Gly Asn Asp Thr Tyr Gly Ala Ala His Asn Leu Leu Val
                       675                 680                 685

Ala His Ala Leu Ala Trp Arg Leu Tyr Asp Gln Gln Phe Arg Pro Ser
       690                 695                 700

Gln Arg Gly Ala Val Ser Leu Ser Leu His Ala Asp Trp Ala Glu Pro
       705                 710                 715                 720

Ala Asn Pro Tyr Ala Asp Ser His Trp Arg Ala Glu Arg Phe Leu
                           725                 730                 735

Gln Phe Glu Ile Ala Trp Phe Ala Glu Pro Leu Phe Lys Thr Gly Asp
                           740                 745                 750

Tyr Pro Ala Ala Met Arg Glu Tyr Ile Ala Ser Lys His Arg Arg Gly
                       755                 760                 765

Leu Ser Ser Ala Leu Pro Arg Leu Thr Glu Ala Glu Arg Leu
                       770                 775                 780

Leu Lys Gly Thr Val Asp Phe Cys Ala Leu Asn His Phe Thr Thr Arg
       785                 790                 795                 800

Phe Val Met His Glu Gln Leu Ala Gly Ser Arg Tyr Asp Ser Asp Arg
                       805                 810                 815

Asp Ile Gln Phe Leu Gln Asp Ile Thr Arg Leu Ser Ser Pro Thr Arg
                       820                 825                 830

Leu Ala Val Ile Pro Trp Gly Val Arg Lys Leu Leu Arg Trp Val Arg
                       835                 840                 845

Arg Asn Tyr Gly Asp Met Asp Ile Tyr Ile Thr Ala Ser Gly Ile Asp
       850                 855                 860

Asp Gln Ala Leu Glu Asp Asp Arg Leu Arg Lys Tyr Tyr Leu Gly Lys
       865                 870                 875                 880

Tyr Leu Gln Glu Val Leu Lys Ala Tyr Leu Ile Asp Lys Val Arg Ile
                           885                 890                 895

Lys Gly Tyr Tyr Ala Phe Lys Leu Ala Glu Glu Lys Ser Lys Pro Arg
                       900                 905                 910

Phe Gly Phe Phe Thr Ser Asp Phe Lys Ala Lys Ser Ser Ile Gln Phe
                       915                 920                 925

Tyr Asn Lys Val Ile Ser Ser Arg Gly Phe Pro Phe Glu Asn Ser Ser
                       930                 935                 940

Ser Arg Cys Ser Gln Thr Gln Glu Asn Thr Glu Cys Thr Val Cys Leu
       945                 950                 955                 960

Phe Leu Val Gln Lys Lys Pro Leu Ile Phe Leu Gly Cys Cys Phe Phe
                           965                 970                 975
```

Ser Thr Leu Val Leu Leu Ser Ile Ala Ile Phe Gln Arg Gln Lys
            980                 985                 990

Arg Arg Lys Phe Trp Lys Ala Lys  Asn Leu Gln His Ile  Pro Leu Lys
        995                 1000                1005

Lys Gly  Lys Arg Val Val Ser
    1010              1015

<210> SEQ ID NO 6
<211> LENGTH: 3163
<212> TYPE: DNA
<213> ORGANISM: homo sapiens
<300> PUBLICATION INFORMATION:
<302> TITLE: Polypeptide, novel DNA and novel antibody
<308> DATABASE ACCESSION NUMBER: AR343616
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(3163)

<400> SEQUENCE: 6

```
cgcgcagcat gcccgccagc gccccgccgc gccgcccgcg gccgccgccg ccgtcgctgt      60
cgctgctgct ggtgctgctg ggcctgggcg gccgccgcct cgtgcggag ccgggcgacg     120 gcgcgcagac ctgggcccgt gtctcgcggc ctcctgcccc cgaggccgcg ggcctcttcc     180 agggcaccttt ccccgacggc ttcctctggg ccgtgggcag cgccgcctac agaccgaggg    240
gcggctggca gcagcacggc aagggtgcgt ccatctggga cacgttcacc caccacccc     300 tggcaccccc gggagactcc cggaacgcca gtctgccgtt gggcgccccg tcgccgctgc    360
agcccgccac cggggacgta gccagcgaca gctacaacaa cgtcttccgc gacacggagg    420
cgctgcgcga gctcgggtc actcactacc gcttctccat ctcgtgggcg cgagtgctcc     480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720
acaaccccta cgtggtggcc tggcacggct acgccaccgg gcgcctggcc ccggcatcc     780 ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggttttg ccaaacccgt atttattgat ggtgactatc   1020
ccgagagcat gaagaataac ctttcatcta ttctgcctga ttttactgaa tctgagaaaa   1080
agttcatcaa ggaactgct gactttttttg ctctttgctt tggacccacc ttgagttttc   1140
aacttttgga ccctcacatg aagttccgcc aattggaatc tccaacctg aggcaactgc    1200 tttcctggat tgaccttgaa tttaaccatc tcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atgggtgga tgtcatcggg tataccgcat   1380
ggtccctcat ggatggtttc gagtggcaca gaggttacag catcaggcgt ggactcttct   1440
atgttgactt tctaagccag gacaagatgt tgttgccaaa gtcttcagcc ttgttctacc   1500
aaaagctgat agagaaaaat ggcttcccctc ctttacctga aaatcagccc ctagaaggga   1560
catttccctg tgactttgct tgggagttg ttgacaacta cattcaagta gataccactc   1620
```

| | |
|---|---|
| tgtctcagtt taccgacctg aatgtttacc tgtgggatgt ccaccacagt aaaaggctta | 1680 |
| ttaaagtgga tggggttgtg accaagaaga ggaaatccta ctgtgttgac tttgctgcca | 1740 |
| tccagcccca gatcgcttta ctccaggaaa tgcacgttac acattttcgc ttctccctgg | 1800 |
| actgggccct gattctccct ctgggtaacc agtcccaggt gaaccacacc atcctgcagt | 1860 |
| actatcgctg catggccagc gagcttgtcc gtgtcaacat caccccagtg gtggccctgt | 1920 |
| ggcagcctat ggccccgaac caaggactgc cgcgcctcct ggccaggcag ggcgcctggg | 1980 |
| agaacccta cactgccctg cctttgcag agtatgcccg actgtgcttt caagagctcg | 2040 |
| gccatcacgt caagctttgg ataacgatga atgagccgta caaggaat atgcataca | 2100 |
| gtgctggcca caaccttctg aaggcccatg ccctggcttg gcatgtgtac aatgaaaagt | 2160 |
| ttaggcatgc tcagaatggg aaaatatcca tagccttgca ggctgattgg atagaacctg | 2220 |
| cctgcccttt ctcccaaaag gacaaagagg tggccgagag agttttggaa tttgacattg | 2280 |
| gctggctggc tgagcccatt ttcggctctg gagattatcc atgggtgatg agggactggc | 2340 |
| tgaaccaaag aaacaatttt cttcttcctt atttcactga agatgaaaaa aagctaatcc | 2400 |
| agggtacctt tgacttttg gctttaagcc attataccac catccttgta gactcagaaa | 2460 |
| aagaagatcc aataaaatac aatgattacc tagaagtgca agaaatgacc gacatcacgt | 2520 |
| ggctcaactc ccccagtcag gtggcggtag tgccctgggg gttgcgcaaa gtgctgaact | 2580 |
| ggctgaagtt caagtacgga gacctcccca tgtacataat atccaacgga atcgatgacg | 2640 |
| ggctgcatgc tgaggacgac cagctgaggg tgtattatat gcagaattac ataaacgaag | 2700 |
| ctctcaaagc ccacatactg gatggtatca atctttgcgg atactttgct tattcgttta | 2760 |
| acgaccgcac agctccgagg tttggcctct atcgttatgc tgcagatcag tttgagccca | 2820 |
| aggcatccat gaaacattac aggaaaatta ttgacagcaa tggtttcccg ggcccagaaa | 2880 |
| ctctggaaag attttgtcca gaagaattca ccgtgtgtac tgagtgcagt ttttttcaca | 2940 |
| cccgaaagtc tttactggct ttcatagctt ttctattttt tgcttctatt atttctctct | 3000 |
| cccttatatt ttactactcg aagaaaggca gaagaagtta caaatagttc tgaacatttt | 3060 |
| tctattcatt cattttgaaa taattatgca gacacatcag ctgttaacca tttgcacctc | 3120 |
| taagtgttgt gaaactgtaa atttcataca tttgacttct aga | 3163 |

<210> SEQ ID NO 7
<211> LENGTH: 3435
<212> TYPE: DNA
<213> ORGANISM: homo sapiens
<300> PUBLICATION INFORMATION:
<302> TITLE: Polypeptide, novel DNA and novel antibody
<308> DATABASE ACCESSION NUMBER: AR343617
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(3435)

<400> SEQUENCE: 7

| | |
|---|---|
| cgcgcagcat gcccgccagc gccccgccgc gccgcccgcg gccgccgccg ccgtcgctgt | 60 |
| cgctgctgct ggtgctgctg ggcctgggcg gccgccgcct gcgtgcggag ccgggcgacg | 120 |
| gcgcgcagac ctgggcccgt gtctcgcggc ctcctgcccc cgaggccgcg ggcctcttcc | 180 |
| agggcacctt ccccgacggc ttcctctggg ccgtgggcag cgccgcctac cagaccgagg | 240 |
| gcggctggca gcagcacggc aagggtgcgt ccatctggga cacgttcacc caccacccc | 300 |
| tggcaccccc gggagactcc cggaacgcca gtctgccgtt gggcgccccg tcgccgctgc | 360 |

```
agcccgccac cggggacgta gccagcgaca gctacaacaa cgtcttccgc gacacggagg    420
cgctgcgcga gctcgggggtc actcactacc gcttctccat ctcgtgggcg cgagtgctcc    480
ccaatggcag cgcgggcgtc cccaaccgcg aggggctgcg ctactaccgg cgcctgctgg    540
agcggctgcg ggagctgggc gtgcagcccg tggtcaccct gtaccactgg gacctgcccc    600
agcgcctgca ggacgcctac ggcggctggg ccaaccgcgc cctggccgac cacttcaggg    660
attacgcgga gctctgcttc cgccacttcg gcggtcaggt caagtactgg atcaccatcg    720 acaacccta cgtggtggcc tggcacggct acgccaccgg gcgcctggcc cccggcatcc    780
ggggcagccc gcggctcggg tacctggtgg cgcacaacct cctcctggct catgccaaag    840
tctggcatct ctacaatact tctttccgtc ccactcaggg aggtcaggtg tccattgccc    900
taagctctca ctggatcaat cctcgaagaa tgaccgacca cagcatcaaa gaatgtcaaa    960
aatctctgga ctttgtacta ggttggtttg ccaaacccgt atttattgat ggtgactatc   1020
ccgagagcat gaagaataac ctttcatcta ttctgcctga ttttactgaa tctgagaaaa   1080
agttcatcaa aggaactgct gacttttttg ctctttgctt tggacccacc ttgagttttc   1140
aacttttgga ccctcacatg aagttccgcc aattggaatc tcccaacctg aggcaactgc   1200
tttcctggat tgaccttgaa tttaaccatc ctcaaatatt tattgtggaa aatggctggt   1260
ttgtctcagg gaccaccaag agagatgatg ccaaatatat gtattacctc aaaaagttca   1320
tcatggaaac cttaaaagcc atcaagctgg atggggtgga tgtcatcggg tataccgcat   1380
ggtccctcat ggatggtttc gagtggcaca gaggttacag catcaggcgt ggactcttct   1440
atgttgactt tctaagccag acaagatgt tgttgccaaa gtcttcagcc ttgttctacc   1500
aaaagctgat agagaaaaat ggcttccctc ctttacctga aaatcagccc ctagaaggga   1560
catttccctg tgactttgct tggggagttg ttgacaacta cattcaagta agtcagctga   1620
caaaaccaat cagcagtctc accaagcccct atcactagta gataccactc tgtctcagtt   1680
taccgacctg aatgtttacc tgtgggatgt ccaccacagt aaaaggctta ttaaagtgga   1740 tgggggttgtg accaagaaga ggaaatccta ctgtgttgac tttgctgcca tccagcccca   1800
gatcgcttta ctccaggaaa tgcacgttac acattttcgc ttctccctgg actgggccct   1860
gattctccct ctgggtaacc agtcccaggt gaaccacacc atcctgcagt actatcgctg   1920
catggccagc gagcttgtcc gtgtcaacat caccccagtg gtggccctgt ggcagcctat   1980
ggccccgaac caaggactgc cgcgcctcct ggccaggcag ggcgcctggg agaaccccta   2040
cactgccctg gcctttgcag agtatgcccg actgtgcttt caagagctcg gccatcacgt   2100
caagctttgg ataacgatga atgagccgta tacaaggaat atgacataca gtgctggcca   2160
caaccttctg aaggcccatg ccctggcttg catgtgtac aatgaaaagt ttaggcatgc   2220
tcagaatggg aaaatatcca tagccttgca ggctgattgg atagaacctg cctgcccttt   2280
ctcccaaaag acaaagagg tggccgagag agtttttggaa tttgacattg gctggctggc   2340
tgagcccatt ttcggctctg gagattatcc atgggtgatg agggactggc tgaaccaaag   2400
aaacaatttt cttcttcctt atttcactga agatgaaaaa aagctaatcc agggtacctt   2460 tgacttttg gctttaagcc attataccac catccttgta gactcagaaa agaagatcc   2520 aataaaatac aatgattacc tagaagtgca agaaatgacc gacatcacgt ggctcaactc   2580
ccccagtcag gtggcggtag tgccctgggg gttgcgcaaa gtgctgaact ggctgaagtt   2640
caagtacgga gacctcccca tgtacataat atccaacgga atcgatgacg ggctgcatgc   2700
tgaggacgac cagctgaggg tgtattatat gcagaattac ataaacgaag ctctcaaagc   2760
```

```
ccacatactg gatggtatca atctttgcgg atactttgct tattcgttta acgaccgcac    2820
agctccgagg tttggcctct atcgttatgc tgcagatcag tttgagccca aggcatccat    2880
gaaacattac aggaaaatta ttgacagcaa tggtttcccg ggcccagaaa ctctggaaag    2940
attttgtcca gaagaattca ccgtgtgtac tgagtgcagt ttttttcaca cccgaaagtc    3000
tttactggct ttcatagctt ttctattttt tgcttctatt atttctctct cccttatatt    3060
ttactactcg aagaaggca gaagaagtta caaatagttc tgaacatttt tctattcatt    3120
cattttgaaa taattatgca gacacatcag ctgttaacca tttgcacctc taagtgttgt    3180
gaaactgtaa atttcataca tttgacttct agaaaacatt tttgtggctt atgacagagg    3240
ttttgaaatg ggcataggtg atcgtaaaat attgaataat gcgaatagtg cctgaatttg    3300
ttctcttttt gggtgattaa aaaactgaca ggcactataa tttctgtaac acactaacaa    3360
aagcatgaaa ataggaacc acaccaatgc aacatttgtg cagaaatttg aatgacaaga    3420
ttaggaatat tttct                                                    3435
```

<210> SEQ ID NO 8
<211> LENGTH: 5032
<212> TYPE: DNA
<213> ORGANISM: homo sapiens
<300> PUBLICATION INFORMATION:
<302> TITLE: Polypeptide, novel DNA and novel antibody
<308> DATABASE ACCESSION NUMBER: AR343618
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(5032)

<400> SEQUENCE: 8

```
cctcccggct cccgcagcat gctagcccgc gcccctcctc gccgcccgcc gcggctggtg      60
ctgctccgtt tgctgttgct gcatctgctg ctgctcgccc tgcgcgcccg ctgcctgagc     120
gctgagccgg gtcagggcgc gcagacctgg gctcgcttcg cgcgcgctcc tgccccagag     180
gccgctggcc tcctccacga caccttcccc gacggtttcc tctgggcggt aggcagcgcc     240
gcctatcaga ccgagggcgg ctggcgacag cacggcaaag gcgcgtccat ctgggacact     300
ttcacccatc actctggggc ggccccgtcc gactccccga tcgtcgtggc gccgtcgggt     360
gccccgtcgc ctccctgtc ctccactgga gatgtggcca gcgatagtta caacaacgtc     420
taccgcgaca cagaggggct gcgcgaactg ggggtcaccc actaccgctt ctccatatcg     480
tgggcgcggg tgctccccaa tggcaccgcg ggcactccca accgcagggg gctgcgctac     540
taccggcggc tgctggagcg gctgcgggag ctgggcgtgc agccggtggt taccctgtac     600
cattgggacc tgccacagcg cctgcaggac acctatggcg gatgggccaa tcgccctg      660 gccgaccatt tcagggatta tgccgagctc tgcttccgcc acttcggtgg tcaggtcaag     720
tactggatca ccattgacaa cccctacgtg gtggcctggc acgggtatgc caccgggcgc     780
ctggccccgg gcgtgagggg cagctccagg ctcgggtacc tggttgccca aacctactt     840 ttggctcatg ccaaagtctg gcatctctac aacacctctt tccgccccac acagggaggc     900
cgggtgtcta tcgccttaag ctcccattgg atcaatcctc gaagaatgac tgactataat     960
atcagagaat gccagaagtc tcttgacttt gtgctaggct ggtttgccaa acccatattt    1020
attgatggcg actacccaga gagtatgaag aacaacctct cgtctcttct gcctgatttt    1080
actgaatctg agaagaggct catcagagga actgctgact tttttgctct ctccttcgga    1140
ccaaccttga gctttcagct attggaccct aacatgaagt tccgccaatt ggagtctccc    1200
```

```
aacctgaggc agcttctgtc ttggatagat ctggaatata accaccctcc aatatttatt    1260
gtggaaaatg gctggtttgt ctcgggaacc accaaaaggg atgatgccaa atatatgtat    1320
tatctcaaga agttcataat ggaaaccttg aaagcaatca gactggatgg ggtcgacgtc    1380
attgggtaca ccgcgtggtc gctcatggac ggtttcgagt ggcataggg ctacagcatc     1440 cggcgaggac tcttctacgt tgactttctg agtcaggaca aggagctgtt gccaaagtct    1500
tcggccttgt tctaccaaaa gctgatagag acaatggct ttcctccttt acctgaaaac     1560
cagccccttg aagggacatt tccctgtgac tttgcttggg gagttgttga caactacgtt    1620
caagtggaca ctactctctc tcagtttact gacccgaatg tctatctgtg ggatgtgcat    1680
cacagtaaga ggcttattaa agtagacggg gttgtagcca agaagagaaa accttactgt    1740
gttgatttct ctgccatccg gcctcagata accttacttc gagaaatgcg ggtcacccac    1800
tttcgcttct ccctggactg ggccctgatc ttgcctctgg gtaaccagac ccaagtgaac    1860
cacacggttc tgcacttcta ccgctgcatg atcagcgagc tggtgcacgc caacatcact    1920
ccagtggtgg ccctgtggca gccagcagcc ccgcaccaag gcctgccaca tgcccttgca    1980
aaacatgggg cctgggagaa cccgcacact gctctggcgt ttgcagacta cgcaaacctg    2040
tgttttaaag agttgggtca ctgggtcaat ctctggatca ccatgaacga gccaaacaca    2100
cggaacatga cctatcgtgc cgggcaccac ctccctgagag cccatgcctt ggcttggcat    2160
ctgtacgatg acaagtttag gcggctcag aaaggcaaaa tatccatcgc cttgcaggct     2220
gactggatag aaccggcctg cccttttctct caaaatgaca agaagtggc cgagagagtt     2280 ttggaatttg atataggctg gctggcagag cctattttg gttccggaga ttatccacgt      2340
gtgatgaggg actggctgaa ccaaaaaaac aatttttcttt tgccctattt caccgaagat    2400 gaaaaaagc tagtccgggg ttcctttgac ttcctggcgg tgagtcatta caccaccatt     2460
ctggtagact gggaaaagga ggatccgatg aaatacaacg attacttgga ggtacaggag    2520
atgactgaca tcacatggct caactctccc agtcaggtgg cagtggtgcc ttggggctg     2580 cgcaaagtgc tcaactggct aaggttcaag tacggagacc tcccgatgta tgtgacagcc    2640
aatggaatcg atgatgaccc ccacgccgag caagactcac tgaggatcta ttatattaag    2700
aattatgtga atgaggctct gaaagcctac gtgttggacg acatcaacct tgtggctac     2760 tttgcgtatt cacttagtga tcgctcagct cccaagtctg gcttttatcg atatgctgcg    2820
aatcagtttg agcccaaacc atctatgaaa cattacagga gaattattga cagcaatggc    2880
ttcctgggtt ctggaacact gggaaggttt tgtccagaag aatacactgt gtgcaccgaa    2940
tgtggatttt ttcaaacccg gaagtctttg ctggtcttca tctcgtttct gttttttact    3000
tttattattt ctcttgctct cattttcac tactccaaga aaggccagag aagttataag      3060
taatgtgaac gtctgcctgg ccattcgctt tgggatcaag atgtacacgc cgtcagccgt    3120
ttgcacctct ctgtgttgtg agccgcattc cacacatttc gattctagaa aacctttttt    3180
gtcatgggtg gtagaggttt taaacaggaa ttggtgagaa taaatattg caggtgaat      3240 ggtatctgaa tctgctctct ttggtggcaa ttacggaatt atactcacca cagtttctac    3300 agtgcccgg aatggaaggc atagaatacg gtagggataa cagtgccaag cagacagaag     3360
tttaaagaac aactttaggg acttgtttat ccatggccat ttttaaattc actcctgttg    3420
gggagtaaca ctctctcaat taccatctta acacctggac tttacctgat ccagttttac    3480
aaggtgaagt agaaaaatat ccagtaaagg tggccaagag ccctgagtcc agagcagccc    3540
```

| | |
|---|---|
| attaagaagc actattccta ccaaatgctg ctaatgtcaa tttacaaata tacttagaaa | 3600 |
| gcacattatg gacatttgta ttcttgtgaa tgttttgag gtgtgcccta aaccccagat | 3660 |
| ccttgagggc tttctcttac caactttcct ttcagagcct gcttgttgga gattcttccc | 3720 |
| cagccccctt cccctttccc tcttgctctg ccccacctcg ctccaccag cttgctccag | 3780 |
| cccaaagatt ctttatttgt ttctcattac cgaaggttgt gagccaccat gtggtttctg | 3840 |
| ggatttgaac tcatgacctc cggaggagct gtcatgctct taaccagccc atgttgaaga | 3900 |
| ttcttttgat aaatattcac aaaaaataaa gatgagccat gagctgttgg cctcttcgga | 3960 |
| agcggaaact gagtgatttg attgaacatc cttttatctt tgaccagacc ttggaatgaa | 4020 |
| tgcaatgacc tttcccacag gaagaaggag gagctctcag tcaaactgta aagaatgcct | 4080 |
| cttcagaata tgctgtcagt gcttggatgc catgatgttc aactttctta gtcgatccgg | 4140 |
| cagcaatcac agtgtgagca cactgggaac ctgtccttgc ggccgccgag atctaccgtg | 4200 |
| tgcttctgtg aagaggcttt gacgtagccc ctctttgagc tcttacacca tgctactgac | 4260 |
| ttctagaaag gctaattagg tcttcttcta cacctaatac cctaagtctt actgactctc | 4320 |
| acgggagaag tctctgtgct acacctgagt ggtcttattg ataaccctga taccagatca | 4380 |
| ggcaagataa atccgtcata gcaggcatgg ctacccttgc tgccacaggg tcacagcaca | 4440 |
| tagctcatca ccctgttatt cttcatcttg caatgtggta tggttttcct ggtgaatgat | 4500 |
| cagcttttgc tgtggtattc tttatacatc tggacttatt attgaaatca aatgctatag | 4560 |
| aatcaatagt ttattttatg tctatttttc ttgatcgcag agtaatatat attaattgta | 4620 |
| aaaaatttaa gaaacaaaaa ctatatgtaa agaaaaaatt ataatataat acagagatgc | 4680 |
| tgctgacagt tcctatgtgt tgtgttttgt atactgagat catgtgatac gtaggcatac | 4740 |
| atcttcttgg gttttttgt ttttgttttt tgttttgttt tgttttgttt tggttttttg | 4800 |
| agatagggtt tctctgtata gccctggctg tcctggaact cactttgcag accaggctag | 4860 |
| cctcaaactc ttattcattt ttactgaagt aattttctg tcattagtct tcaagagcaa | 4920 |
| aactttaata gttatggaga atattgccag aacagctcaa aactgtttta tttgttggtc | 4980 |
| caatttccca ttaattagtt caataataaa tatcatttag aaataaaaaa aa | 5032 |

<210> SEQ ID NO 9
<211> LENGTH: 1650
<212> TYPE: DNA
<213> ORGANISM: homo sapiens
<300> PUBLICATION INFORMATION:
<302> TITLE: Polypeptide, novel DNA and novel antibody
<308> DATABASE ACCESSION NUMBER: AR343619
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(1650)

<400> SEQUENCE: 9

| | |
|---|---|
| atgctagccc gcgcccctcc tcgccgcccg ccgcggctgg tgctgctccg tttgctgttg | 60 |
| ctgcatctgc tgctgctcgc cctgcgcgcc cgctgcctga gcgctgagcc gggtcagggc | 120 |
| gcgcagacct gggctcgctt cgcgcgcgct cctgccccag aggccgctgg cctcctccac | 180 |
| gacaccttcc ccgacggttt cctctgggcg gtaggcagcg ccgcctatca gaccgagggc | 240 |
| ggctggcgac agcacggcaa aggcgcgtcc atctgggaca cttcaccca tcactctggg | 300 |
| gcggccccgt ccgactcccc gatcgtcgtg gcgccgtcgg gtgcccgtc gcctcccctg | 360 |
| tcctccactg gagatgtggc cagcgatagt tacaacaacg tctaccgcga cacagagggg | 420 |

| | |
|---|---|
| ctgcgcgaac tgggggtcac ccactaccgc ttctccatat cgtgggcgcg ggtgctcccc | 480 |
| aatggcaccg cggcactcc caaccgcgag gggctgcgct actaccgcg gctgctggag | 540 |
| cggctgcggg agctgggcgt gcagccggtg gttaccctgt accattggga cctgccacag | 600 |
| cgcctgcagg acacctatgg cggatgggcc aatcgcgccc tggccgacca tttcagggat | 660 |
| tatgccgagc tctgcttccg ccacttcggt ggtcaggtca agtactggat caccattgac | 720 |
| aaccccctacg tggtggcctg gcacgggtat gccaccgggc gcctggcccc gggcgtgagg | 780 |
| ggcagctcca ggctcgggta cctggttgcc cacaacctac ttttggctca tgccaaagtc | 840 |
| tggcatctct acaacacctc tttccgcccc acacagggag gccgggtgtc tatcgcctta | 900 |
| agctcccatt ggatcaatcc tcgaagaatg actgactata atatcagaga atgccagaag | 960 |
| tctcttgact ttgtgctagg ctggtttgcc aaacccatat ttattgatgg cgactaccca | 1020 |
| gagagtatga agaacaacct ctcgtctctt ctgcctgatt ttactgaatc tgagaagagg | 1080 |
| ctcatcagag gaactgctga ctttttttgct ctctgcttcg gaccaacctt gagctttcag | 1140 |
| ctattggacc ctaacatgaa gttccgccaa ttggagtctc ccaacctgag gcagcttcts | 1200 |
| tcttggatag atctggaata taaccaccct ccaatatttta ttgtggaaaa tggctggttt | 1260 |
| gtctcgggaa ccaccaaaag ggatgatgcc aaatatatgt attatctcaa gaagttcata | 1320 |
| atggaaacct aaaagcaat cagactggat ggggtcgacg tcattgggta caccgcgtgg | 1380 |
| tcgctcatga cggttttcga gtggcatagg ggctacagca tccggcgagg actcttctac | 1440 |
| gttgactttc tgagtcagga caaggagctg ttgccaaagt cttcggcctt gttctaccaa | 1500 |
| aagctgatag aggacaatgg ctttcctcct ttacctgaaa accagcccct tgaagggaca | 1560 |
| tttccctgtg actttgcttg gggagttgtt gacaactacg tacaagtaag tcctttgaca | 1620 |
| aaacccagtg tcggcctctt gcttcctcac | 1650 |

<210> SEQ ID NO 10
<211> LENGTH: 3460
<212> TYPE: DNA
<213> ORGANISM: homo sapiens
<300> PUBLICATION INFORMATION:
<302> TITLE: Polypeptide, novel DNA and novel antibody
<308> DATABASE ACCESSION NUMBER: AR343620
<309> DATABASE ENTRY DATE: 2003-08-17
<310> PATENT DOCUMENT NUMBER: US 6,579,850
<311> PATENT FILING DATE: 1999-06-25
<313> RELEVANT RESIDUES IN SEQ ID NO: (1)..(3460)

<400> SEQUENCE: 10

| | |
|---|---|
| cagggaatga atggatttc ttcagcactg atgaaataac cacacgctat aggaatacaa | 60 |
| tgtccaacgg gggattgcaa agatctgtca tcctgtcagc acttattctg ctacgagctg | 120 |
| ttactggatt ctctggagat ggaagagcta tggtctaa aaatcctaat tttactccgg | 180 |
| taaatgaaag tcagctgttt ctctatggca cttttcctaa aaacttttc tggggtattg | 240 |
| ggactggagc attgcaagtg aagggagtt ggaagaagga tggaaaagga ccttctatat | 300 |
| gggatcattt catccacaca caccttaaaa atgtcagcag cacgaatggt tccagtgaca | 360 |
| gttatatttt tctggaaaaa gacttatcag ccctggattt tataggagtt tctttttatc | 420 |
| aattttcaat ttcctggcca aggcttttcc ccgatggaat agtaacagtt gccaacgcaa | 480 |
| aaggtctgca gtactacagt actcttctgg acgctctagt gcttagaaac attgaaccta | 540 |
| tagttacttt ataccactgg gatttgcctt tggcactaca agaaaaatat gggggtggaa | 600 |
| aaaatgatac cataatagat atcttcaatg actatgccac atactgtttc cagatgtttg | 660 |

```
gggaccgtgt caaatattgg attacaattc acaacccata tctagtggct tggcatgggt      720
atgggacagg tatgcatgcc cctggagaga agggaaattt agcagctgtc tacactgtgg      780
gacacaactt gatcaaggct cactcgaaag tttggcataa ctacaacaca catttccgcc      840
cacatcagaa gggttggtta tcgatcacgt tgggatctca ttggatcgag ccaaaccggt      900
cggaaaacac gatggatata ttcaaatgtc aacaatccat ggtttctgtg cttggatggt      960
ttgccaaccc tatccatggg gatggcgact atccagaggg gatgagaaag aagttgttct     1020
ccgttctacc cattttctct gaagcagaga agcatgagat gagaggcaca gctgatttct     1080
ttgccttttc ttttggaccc aacaacttca agcccctaaa caccatggct aaaatgggac     1140
aaaatgtttc acttaattta agagaagcgc tgaactggat taaactggaa tacaacaacc     1200
ctcgaatctt gattgctgag aatggctggt tcacagacag tcgtgtgaaa acagaagaca     1260
ccacggccat ctacatgatg aagaatttcc tcagccaggt gcttcaagca ataaggttag     1320
atgaaatacg agtgtttggt tatactgcct ggtctctcct ggatggcttt aatggcagg      1380 atgcttacac catccgccga ggattatttt atgtggattt taacagtaaa cagaaagagc     1440
ggaaacctaa gtcttcagca cactactaca aacagatcat acgagaaaat ggttttctctt     1500 taaaagagtc cacgccagat gtgcagggcc agtttccctg tgacttctcc tggggtgtca     1560
ctgaatctgt tcttaagccc gagtctgtgg cttcgtcccc acagttcagc gatcctcatc     1620
tgtacgtgtg aacgccact ggcaacagac tgttgcaccg agtggaaggg gtgaggctga      1680
aaacacgacc cgctcaatgc acagattttg taaacatcaa aaaacaactt gagatgttgg     1740
caagaatgaa agtcacccac taccggtttg ctctggattg ggcctcggtc cttcccactg     1800
gcaacctgtc cgcggtgaac cgacaggccc tgaggtacta caggtgcgtg gtcagtgagg     1860
ggctgaagct tggcatctcc gcgatggtca ccctgtatta tccgaccac gcccacctag      1920 gcctccccga gcctctgttg catgccgacg ggtggctgaa cccatcgacg gccgaggcct     1980
tccaggccta cgctggggctg tgcttccagg agctggggga cctggtgaag ctctggatca     2040
ccatcaacga gcctaaccgg ctaagtgaca tctacaaccg ctctggcaac gacacctacg     2100
gggcggcgca caacctgctg gtgggccacg ccctggcctg gcgcctctac gaccagcagt     2160
tcaggccgtc acagcgcggg gccgtgtcgc tgtcgctgca cgcggactgg gcggaacccg     2220
ccaaccccta tgctgactcg cactggaggg cggccgagcg cttcctgcag ttcgagatcg     2280
cctggttcgc cgagccgctc ttcaagaccg gggactaccc cgcggccatg agggaataca     2340
ttgcctccaa gcaccgacgg gggctttcca gctcggccct gccgcgcctc accgaggccg     2400
aaaggaggct gctcaagggc acggtcgact tctgcgcgct caaccacttc accactaggt     2460
tcgtgatgca cgagcagctg gccggcagcc gctacgactc ggacagggac atccagtttc     2520
tgcaggacat caccgcctg agctccccca cgcgcctggc tgtgattccc tggggggtgc     2580
gcaagctgct gcgtgggtc cggaggaact acgcgacat ggacatttac atcaccgcca      2640
gtggcatcga cgaccaggct ctggaggatg accggctccg gaagtactac ctagggaagt     2700
accttcagga ggtgctgaaa gcatacctga ttgataaagt cagaatcaaa ggctattatg     2760
cattcaaact ggctgaagag aaatctaaac ccagatttgg attcttcaca tctgatttta     2820
aagctaaatc ctcaatacaa ttttacaaca aagtgatcag cagcaggggc ttccctttg     2880 agaacagtag ttctagatgc agtcagaccc aagaaaatac agagtgcact gtctgcttat     2940
tccttgtgca gaagaaacca ctgatattcc tgggttgttg cttcttctcc accctggttc     3000
tactcttatc aattgccatt tttcaaaggc agaagagaag aaagttttgg aaagcaaaaa     3060
```

```
acttacaaca cataccatta aagaaaggca agagagttgt tagctaaact gatctgtctg    3120
catgatagac agtttaaaaa ttcatcccag ttccatatgc tggtaactta caggagatat    3180
acctgtatta tagaaagaca atctgagata cagctgtaac caaggtgatg acaattgtct    3240
ctgctgtgtg gttcaaagaa cattcccctta ggtgttgaca tcagtgaact cagttcttgg    3300
atgtaaacat aaaggcttca tcctgacagt aagctatgag gattacatgc tacattgctt    3360
cttaaagttt catcaactgt attccatcat tctgctttag ctttcatctc taccaatagc    3420
tacttgtggt acaataaatt attttttaaga agaaaaaaaa                          3460
```

<210> SEQ ID NO 11
<211> LENGTH: 1012
<212> TYPE: PRT
<213> ORGANISM: homo sapiens
<300> PUBLICATION INFORMATION:
<308> DATABASE ACCESSION NUMBER: NP_004786
<309> DATABASE ENTRY DATE: 2008-04-20
<313> RELEVANT RESIDUES IN SEQ ID NO: (1)..(1012)

<400> SEQUENCE: 11

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
```

-continued

```
            275                 280                 285
Thr Gln Gly Gly Gln Val Ser Ile Ala Leu Ser Ser His Trp Ile Asn
        290                 295                 300
Pro Arg Arg Met Thr Asp His Ser Ile Lys Glu Cys Gln Lys Ser Leu
305                 310                 315                 320
Asp Phe Val Leu Gly Trp Phe Ala Lys Pro Val Phe Ile Asp Gly Asp
                325                 330                 335
Tyr Pro Glu Ser Met Lys Asn Asn Leu Ser Ser Ile Leu Pro Asp Phe
            340                 345                 350
Thr Glu Ser Glu Lys Lys Phe Ile Lys Gly Thr Ala Asp Phe Phe Ala
        355                 360                 365
Leu Cys Phe Gly Pro Thr Leu Ser Phe Gln Leu Leu Asp Pro His Met
370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
                405                 410                 415
Trp Phe Val Ser Gly Thr Thr Lys Arg Asp Asp Ala Lys Tyr Met Tyr
            420                 425                 430
Tyr Leu Lys Lys Phe Ile Met Glu Thr Leu Lys Ala Ile Lys Leu Asp
        435                 440                 445
Gly Val Asp Val Ile Gly Tyr Thr Ala Trp Ser Leu Met Asp Gly Phe
450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
            500                 505                 510
Gln Pro Leu Glu Gly Thr Phe Pro Cys Asp Phe Ala Trp Gly Val Val
        515                 520                 525
Asp Asn Tyr Ile Gln Val Asp Thr Thr Leu Ser Gln Phe Thr Asp Leu
530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
                565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
        595                 600                 605
Ser Gln Val Asn His Thr Ile Leu Gln Tyr Tyr Arg Cys Met Ala Ser
        610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
                645                 650                 655
Trp Glu Asn Pro Tyr Thr Ala Leu Ala Phe Ala Glu Tyr Ala Arg Leu
            660                 665                 670
Cys Phe Gln Glu Leu Gly His His Val Lys Leu Trp Ile Thr Met Asn
        675                 680                 685
Glu Pro Tyr Thr Arg Asn Met Thr Tyr Ser Ala Gly His Asn Leu Leu
        690                 695                 700
```

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
        740                 745                 750

Leu Glu Phe Asp Ile Gly Trp Leu Ala Glu Pro Ile Phe Gly Ser Gly
    755                 760                 765

Asp Tyr Pro Trp Val Met Arg Asp Trp Leu Asn Gln Arg Asn Asn Phe
770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 12
<211> LENGTH: 1012
<212> TYPE: PRT
<213> ORGANISM: homo sapiens
<300> PUBLICATION INFORMATION:
<308> DATABASE ACCESSION NUMBER: CAH71888
<309> DATABASE ENTRY DATE: 2008-02-24
<313> RELEVANT RESIDUES IN SEQ ID NO: (1)..(1012)

<400> SEQUENCE: 12

Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Leu Arg
            20                  25                  30

```
Ala Glu Pro Gly Asp Gly Ala Gln Thr Trp Ala Arg Phe Ser Arg Pro
             35                  40                  45

Pro Ala Pro Glu Ala Ala Gly Leu Phe Gln Gly Thr Phe Pro Asp Gly
 50                  55                  60

Phe Leu Trp Ala Val Gly Ser Ala Ala Tyr Gln Thr Glu Gly Gly Trp
 65                  70                  75                  80

Gln Gln His Gly Lys Gly Ala Ser Ile Trp Asp Thr Phe Thr His His
                 85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
```

```
                    450                 455                 460
Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                    485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
                515                 520                 525

Asp Asn Tyr Ile Gln Val Asp Thr Thr Leu Ser Gln Phe Thr Asp Leu
                530                 535                 540

Asn Val Tyr Leu Trp Asp Val His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
                595                 600                 605

Ser Gln Val Asn His Thr Ile Leu Gln Tyr Tyr Arg Cys Met Ala Ser
                610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
                660                 665                 670

Cys Phe Gln Glu Leu Gly His His Val Lys Leu Trp Ile Thr Met Asn
                675                 680                 685

Glu Pro Tyr Thr Arg Asn Met Thr Tyr Ser Ala Gly His Asn Leu Leu
                690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
                755                 760                 765

Asp Tyr Pro Trp Val Met Arg Asp Trp Leu Asn Gln Arg Asn Asn Phe
                770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
865                 870                 875                 880
```

```
Ala Glu Asp Asp Gln Leu Arg Val Tyr Tyr Met Gln Asn Tyr Ile Asn
            885                 890                 895

Glu Ala Leu Lys Ala His Ile Leu Asp Gly Ile Asn Leu Cys Gly Tyr
        900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 13
<211> LENGTH: 1012
<212> TYPE: PRT
<213> ORGANISM: homo sapiens
<300> PUBLICATION INFORMATION:
<308> DATABASE ACCESSION NUMBER: BAA24940
<309> DATABASE ENTRY DATE: 2004-11-03
<313> RELEVANT RESIDUES IN SEQ ID NO: (1)..(1012)

<400> SEQUENCE: 13

Met Pro Ala Ser Ala Pro Pro Arg Arg Pro Arg Pro Pro Gln Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
            85                  90                  95

Pro Leu Ala Pro Pro Gly Asp Ser Arg Asn Ala Ser Leu Pro Leu Gly
        100                 105                 110

Ala Pro Ser Pro Leu Gln Pro Ala Thr Gly Asp Val Ala Ser Asp Ser
    115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
    195                 200                 205
```

```
Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
            355                 360                 365

Leu Cys Phe Gly Pro Thr Leu Ser Phe Gln Leu Leu Asp Pro His Met
370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
                580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
610                 615                 620

Glu Leu Val Arg Val Asn Ile Thr Pro Val Val Ala Leu Trp Gln Pro
```

```
                    625                 630                 635                 640
            Met Ala Pro Asn Gln Gly Leu Pro Arg Leu Leu Ala Arg Gln Gly Ala
                            645                 650                 655

Trp Glu Asn Pro Tyr Thr Ala Leu Ala Phe Ala Glu Tyr Ala Arg Leu
                            660                 665                 670

Cys Phe Gln Glu Leu Gly His His Val Lys Leu Trp Ile Thr Met Asn
                            675                 680                 685

Glu Pro Tyr Thr Arg Asn Met Thr Tyr Ser Ala Gly His Asn Leu Leu
                            690                 695                 700

Lys Ala His Ala Leu Ala Trp His Val Tyr Asn Glu Lys Phe Arg His
            705                 710                 715                 720

Ala Gln Asn Gly Lys Ile Ser Ile Ala Leu Gln Ala Asp Trp Ile Glu
                            725                 730                 735

Pro Ala Cys Pro Phe Ser Gln Lys Asp Lys Glu Val Ala Glu Arg Val
                            740                 745                 750

Leu Glu Phe Asp Ile Gly Trp Leu Ala Glu Pro Ile Phe Gly Ser Gly
                            755                 760                 765

Asp Tyr Pro Trp Val Met Arg Asp Trp Leu Asn Gln Arg Asn Asn Phe
                            770                 775                 780

Leu Leu Pro Tyr Phe Thr Glu Asp Glu Lys Lys Leu Ile Gln Gly Thr
            785                 790                 795                 800

Phe Asp Phe Leu Ala Leu Ser His Tyr Thr Thr Ile Leu Val Asp Ser
                            805                 810                 815

Glu Lys Glu Asp Pro Ile Lys Tyr Asn Asp Tyr Leu Glu Val Gln Glu
                            820                 825                 830

Met Thr Asp Ile Thr Trp Leu Asn Ser Pro Ser Gln Val Ala Val Val
                            835                 840                 845

Pro Trp Gly Leu Arg Lys Val Leu Asn Trp Leu Lys Phe Lys Tyr Gly
                            850                 855                 860

Asp Leu Pro Met Tyr Ile Ile Ser Asn Gly Ile Asp Asp Gly Leu His
            865                 870                 875                 880

Ala Glu Asp Asp Gln Leu Arg Val Tyr Tyr Met Gln Asn Tyr Ile Asn
                            885                 890                 895

Glu Ala Leu Lys Ala His Ile Leu Asp Gly Ile Asn Leu Cys Gly Tyr
                            900                 905                 910

Phe Ala Tyr Ser Phe Asn Asp Arg Thr Ala Pro Arg Phe Gly Leu Tyr
                            915                 920                 925

Arg Tyr Ala Ala Asp Gln Phe Glu Pro Lys Ala Ser Met Lys His Tyr
                            930                 935                 940

Arg Lys Ile Ile Asp Ser Asn Gly Phe Pro Gly Pro Glu Thr Leu Glu
            945                 950                 955                 960

Arg Phe Cys Pro Glu Glu Phe Thr Val Cys Thr Glu Cys Ser Phe Phe
                            965                 970                 975

His Thr Arg Lys Ser Leu Leu Ala Phe Ile Ala Phe Leu Phe Phe Ala
                            980                 985                 990

Ser Ile Ile Ser Leu Ser Leu Ile Phe Tyr Tyr Ser Lys Lys Gly Arg
                            995                 1000                1005

Arg Ser Tyr Lys
                    1010

<210> SEQ ID NO 14
<211> LENGTH: 1012
<212> TYPE: PRT
<213> ORGANISM: homo sapiens
```

<300> PUBLICATION INFORMATION:
<308> DATABASE ACCESSION NUMBER: EAX08526
<309> DATABASE ENTRY DATE: 2006-12-18
<313> RELEVANT RESIDUES IN SEQ ID NO: (1)..(1012)

<400> SEQUENCE: 14

```
Met Pro Ala Ser Ala Pro Pro Arg Arg Pro Arg Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
                35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380
```

```
Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
            405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
            450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
            485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Leu
530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
            565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
            595                 600                 605

Ser Gln Val Asn His Thr Ile Leu Gln Tyr Tyr Arg Cys Met Ala Ser
            610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
            645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
            675                 680                 685

Glu Pro Tyr Thr Arg Asn Met Thr Tyr Ser Ala Gly His Asn Leu Leu
            690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
            725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
            770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
```

```
                    805                 810                 815
Glu Lys Glu Asp Pro Ile Lys Tyr Asn Asp Tyr Leu Glu Val Gln Glu
                820                 825                 830

Met Thr Asp Ile Thr Trp Leu Asn Ser Pro Ser Gln Val Ala Val Val
            835                 840                 845

Pro Trp Gly Leu Arg Lys Val Leu Asn Trp Leu Lys Phe Lys Tyr Gly
        850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Met Gln Asn Tyr Ile Asn
                885                 890                 895

Glu Ala Leu Lys Ala His Ile Leu Asp Gly Ile Asn Leu Cys Gly Tyr
                900                 905                 910

Phe Ala Tyr Ser Phe Asn Asp Arg Thr Ala Pro Arg Phe Gly Leu Tyr
            915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
                980                 985                 990

Ser Ile Ile Ser Leu Ser Leu Ile  Phe Tyr Tyr Ser Lys  Lys Gly Arg
            995                 1000                1005

Arg Ser  Tyr Lys
    1010

<210> SEQ ID NO 15
<211> LENGTH: 549
<212> TYPE: PRT
<213> ORGANISM: homo sapiens
<300> PUBLICATION INFORMATION:
<308> DATABASE ACCESSION NUMBER: BAA24941
<309> DATABASE ENTRY DATE: 2004-11-02
<313> RELEVANT RESIDUES IN SEQ ID NO: (1)..(549)

<400> SEQUENCE: 15

Met Pro Ala Ser Ala Pro Pro Arg Arg Pro Arg Pro Pro Gln Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140
```

```
Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gln Val Ser Ile Ala Leu Ser Ser His Trp Ile Asn
290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
        370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Ser Gln Leu Thr Lys Pro Ile Ser Ser Leu
        530                 535                 540

Thr Lys Pro Tyr His
545
```

<210> SEQ ID NO 16
<211> LENGTH: 549
<212> TYPE: PRT
<213> ORGANISM: homo sapiens
<300> PUBLICATION INFORMATION:
<308> DATABASE ACCESSION NUMBER: EAX08525
<309> DATABASE ENTRY DATE: 2006-12-18
<313> RELEVANT RESIDUES IN SEQ ID NO: (1)..(549)

<400> SEQUENCE: 16

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
            20                  25                  30

Ala Glu Pro Gly Asp Gly Ala Gln Thr Trp Ala Arg Phe Ser Arg Pro
        35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala

-continued

```
                355                 360                 365
Leu Cys Phe Gly Pro Thr Leu Ser Phe Gln Leu Leu Asp Pro His Met
370                     375                 380
Lys Phe Arg Gln Leu Glu Ser Pro Asn Leu Arg Gln Leu Leu Ser Trp
385                     390                 395                 400
Ile Asp Leu Glu Phe Asn His Pro Gln Ile Phe Ile Val Glu Asn Gly
                        405                 410                 415
Trp Phe Val Ser Gly Thr Thr Lys Arg Asp Asp Ala Lys Tyr Met Tyr
                420                     425                 430
Tyr Leu Lys Lys Phe Ile Met Glu Thr Leu Lys Ala Ile Lys Leu Asp
            435                 440                 445
Gly Val Asp Val Ile Gly Tyr Thr Ala Trp Ser Leu Met Asp Gly Phe
    450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
                485                 490                 495
Tyr Gln Lys Leu Ile Glu Lys Asn Gly Phe Pro Pro Leu Pro Glu Asn
                500                 505                 510
Gln Pro Leu Glu Gly Thr Phe Pro Cys Asp Phe Ala Trp Gly Val Val
            515                 520                 525
Asp Asn Tyr Ile Gln Val Ser Gln Leu Thr Lys Pro Ile Ser Ser Leu
    530                 535                 540
Thr Lys Pro Tyr His
545

<210> SEQ ID NO 17
<211> LENGTH: 273
<212> TYPE: PRT
<213> ORGANISM: homo sapiens
<300> PUBLICATION INFORMATION:
<308> DATABASE ACCESSION NUMBER: CAC94767
<309> DATABASE ENTRY DATE: 2005-04-18
<313> RELEVANT RESIDUES IN SEQ ID NO: (1)..(273)

<400> SEQUENCE: 17

Met Pro Ala Ser Ala Pro Pro Arg Arg Pro Arg Pro Pro Pro Ser
1               5                   10                  15
Leu Ser Leu Leu Leu Val Leu Leu Gly Leu Gly Gly Arg Arg Leu Arg
                20                  25                  30
Ala Glu Pro Gly Asp Gly Ala Gln Thr Trp Ala Arg Phe Ser Arg Pro
            35                  40                  45
Pro Ala Pro Glu Ala Ala Gly Leu Phe Gln Gly Thr Phe Pro Asp Gly
        50                  55                  60
Phe Leu Trp Ala Val Gly Ser Ala Ala Tyr Gln Thr Glu Gly Gly Trp
65                  70                  75                  80
Gln Gln His Gly Lys Gly Ala Ser Ile Trp Asp Thr Phe Thr His His
                85                  90                  95
Pro Leu Ala Pro Pro Gly Asp Ser Arg Asn Ala Ser Leu Pro Leu Gly
                100                 105                 110
Ala Pro Ser Pro Leu Gln Pro Ala Thr Gly Asp Val Ala Ser Asp Ser
            115                 120                 125
Tyr Asn Asn Val Phe Arg Asp Thr Glu Ala Leu Arg Glu Leu Gly Val
    130                 135                 140
Thr His Tyr Arg Phe Ser Ile Ser Trp Ala Arg Val Leu Pro Asn Gly
145                 150                 155                 160
```

Ser Ala Gly Val Pro Asn Arg Glu Gly Leu Arg Tyr Tyr Arg Arg Leu
            165                 170                 175

Leu Glu Arg Leu Arg Glu Leu Gly Val Gln Pro Val Val Thr Leu Tyr
        180                 185                 190

His Trp Asp Leu Pro Gln Arg Leu Gln Asp Ala Tyr Gly Gly Trp Ala
            195                 200                 205

Asn Arg Ala Leu Ala Asp His Phe Arg Asp Tyr Ala Glu Leu Cys Phe
        210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu

<210> SEQ ID NO 18
<211> LENGTH: 739
<212> TYPE: PRT
<213> ORGANISM: homo sapiens
<300> PUBLICATION INFORMATION:
<308> DATABASE ACCESSION NUMBER: CAC94773
<309> DATABASE ENTRY DATE: 2005-04-18
<313> RELEVANT RESIDUES IN SEQ ID NO: (1)..(739)

<400> SEQUENCE: 18

Ala His Ala Lys Val Trp His Leu Tyr Asn Thr Ser Phe Arg Pro Thr
1               5                   10                  15

Gln Gly Gly Gln Val Ser Ile Ala Leu Ser Ser His Trp Ile Asn Pro
            20                  25                  30

Arg Arg Met Thr Asp His Ser Ile Lys Glu Cys Gln Lys Ser Leu Asp
        35                  40                  45

Phe Val Leu Gly Trp Phe Ala Lys Pro Val Phe Ile Asp Gly Asp Tyr
    50                  55                  60

Pro Glu Ser Met Lys Asn Asn Leu Ser Ser Ile Leu Pro Asp Phe Thr
65                  70                  75                  80

Glu Ser Glu Lys Lys Phe Ile Lys Gly Thr Ala Asp Phe Phe Ala Leu
                85                  90                  95

Cys Phe Gly Pro Thr Leu Ser Phe Gln Leu Leu Asp Pro His Met Lys
            100                 105                 110

Phe Arg Gln Leu Glu Ser Pro Asn Leu Arg Gln Leu Leu Ser Trp Ile
        115                 120                 125

Asp Leu Glu Phe Asn His Pro Gln Ile Phe Ile Val Glu Asn Gly Trp
    130                 135                 140

Phe Val Ser Gly Thr Thr Lys Arg Asp Asp Ala Lys Tyr Met Tyr Tyr
145                 150                 155                 160

Leu Lys Lys Phe Ile Met Glu Thr Leu Lys Ala Ile Lys Leu Asp Gly
                165                 170                 175

Val Asp Val Ile Gly Tyr Thr Ala Trp Ser Leu Met Asp Gly Phe Glu
            180                 185                 190

Trp His Arg Gly Tyr Ser Ile Arg Arg Gly Leu Phe Tyr Val Asp Phe
        195                 200                 205

Leu Ser Gln Asp Lys Met Leu Leu Pro Lys Ser Ser Ala Leu Phe Tyr
    210                 215                 220

Gln Lys Leu Ile Glu Lys Asn Gly Phe Pro Pro Leu Pro Glu Asn Gln

```
                225                 230                 235                 240

Pro Leu Glu Gly Thr Phe Pro Cys Asp Phe Ala Trp Gly Val Val Asp
                245                 250                 255

Asn Tyr Ile Gln Val Asp Thr Thr Leu Ser Gln Phe Thr Asp Leu Asn
                260                 265                 270

Val Tyr Leu Trp Asp Val His His Ser Lys Arg Leu Ile Lys Val Asp
                275                 280                 285

Gly Val Val Thr Lys Lys Arg Lys Ser Tyr Cys Val Asp Phe Ala Ala
                290                 295                 300

Ile Gln Pro Gln Ile Ala Leu Leu Gln Glu Met His Val Thr His Phe
305                 310                 315                 320

Arg Phe Ser Leu Asp Trp Ala Leu Ile Leu Pro Leu Gly Asn Gln Ser
                325                 330                 335

Gln Val Asn His Thr Ile Leu Gln Tyr Tyr Arg Cys Met Ala Ser Glu
                340                 345                 350

Leu Val Arg Val Asn Ile Thr Pro Val Val Ala Leu Trp Gln Pro Met
                355                 360                 365

Ala Pro Asn Gln Gly Leu Pro Arg Leu Leu Ala Arg Gln Gly Ala Trp
                370                 375                 380

Glu Asn Pro Tyr Thr Ala Leu Ala Phe Ala Glu Tyr Ala Arg Leu Cys
385                 390                 395                 400

Phe Gln Glu Leu Gly His His Val Lys Leu Trp Ile Thr Met Asn Glu
                405                 410                 415

Pro Tyr Thr Arg Asn Met Thr Tyr Ser Ala Gly His Asn Leu Leu Lys
                420                 425                 430

Ala His Ala Leu Ala Trp His Val Tyr Asn Glu Lys Phe Arg His Ala
                435                 440                 445

Gln Asn Gly Lys Ile Ser Ile Ala Leu Gln Ala Asp Trp Ile Glu Pro
                450                 455                 460

Ala Cys Pro Phe Ser Gln Lys Asp Lys Glu Val Ala Glu Arg Val Leu
465                 470                 475                 480

Glu Phe Asp Ile Gly Trp Leu Ala Glu Pro Ile Phe Gly Ser Gly Asp
                485                 490                 495

Tyr Pro Trp Val Met Arg Asp Trp Leu Asn Gln Arg Asn Asn Phe Leu
                500                 505                 510

Leu Pro Tyr Phe Thr Glu Asp Glu Lys Lys Leu Ile Gln Gly Thr Phe
                515                 520                 525

Asp Phe Leu Ala Leu Ser His Tyr Thr Thr Ile Leu Val Asp Ser Glu
                530                 535                 540

Lys Glu Asp Pro Ile Lys Tyr Asn Asp Tyr Leu Glu Val Gln Glu Met
545                 550                 555                 560

Thr Asp Ile Thr Trp Leu Asn Ser Pro Ser Gln Val Ala Val Val Pro
                565                 570                 575

Trp Gly Leu Arg Lys Val Leu Asn Trp Leu Lys Phe Lys Tyr Gly Asp
                580                 585                 590

Leu Pro Met Tyr Ile Ile Ser Asn Gly Ile Asp Asp Gly Leu His Ala
                595                 600                 605

Glu Asp Asp Gln Leu Arg Val Tyr Tyr Met Gln Asn Tyr Ile Asn Glu
                610                 615                 620

Ala Leu Lys Ala His Ile Leu Asp Gly Ile Asn Leu Cys Gly Tyr Phe
625                 630                 635                 640

Ala Tyr Ser Phe Asn Asp Arg Thr Ala Pro Arg Phe Gly Leu Tyr Arg
                645                 650                 655
```

```
Tyr Ala Ala Asp Gln Phe Glu Pro Lys Ala Ser Met Lys His Tyr Arg
            660             665             670

Lys Ile Ile Asp Ser Asn Gly Phe Pro Gly Pro Glu Thr Leu Glu Arg
            675             680             685

Phe Cys Pro Glu Glu Phe Thr Val Cys Thr Glu Cys Ser Phe His
        690             695             700

Thr Arg Lys Ser Leu Leu Ala Phe Ile Ala Phe Leu Phe Phe Ala Ser
705                 710             715                 720

Ile Ile Ser Leu Ser Leu Ile Phe Tyr Tyr Ser Lys Lys Gly Arg Arg
                725             730             735

Ser Tyr Lys
```

KLOTHO PROTEIN AND RELATED COMPOUNDS FOR THE TREATMENT AND DIAGNOSIS OF CANCER

RELATED PATENT APPLICATIONS

The present application is a Continuation-in-Part of U.S. Ser. No. 12/598,963, the US National Phase of PCT/IL2008/000618, having an International filing date of 6 May 2008 and published as WO 2008/135993 on 13 Nov. 2008, which gains priority from U.S. Provisional Patent Application No. 60/916,787 filed 8 May 2007 and from U.S. Provisional Patent Application No. 61/042,918 filed 7 Apr. 2008, both included by reference as if fully set forth herein.

Some aspects of the teachings herein have been published in the peer-reviewed article published online on 13 May 2011 in Clinical Cancer Research by some of the Inventors entitled "KL1 internal repeat mediates klotho tumor suppressor activities and inhibits bFGF and IGF-1 signaling in pancreatic cancer", which is included by reference as if fully set-forth herein.

FIELD AND BACKGROUND OF THE INVENTION

The present invention relates to the field of therapeutics, and more specifically to the use of the klotho protein and related compounds for the treatment and diagnosis of cancer, such as breast cancer and pancreatic cancer as well as other IGF-1 dependent cancers.

Cancer is a group of diseases in which cells grow and divide without respect to normal limits, forming a tumor, and invading and destroying adjacent tissues. Cancer cells may spread to other locations in the body, resulting in a metastatic tumor composed of cells of the same type as those of the original tumor. Cancers are treated in a number of ways including surgery (excision of a tumor), radiation therapy (directed irradiation with X-rays to destroy cancer cells) and chemotherapy (administration of APIs that are more toxic to cancer cells than to non-cancer cells). All these therapies are associated with severe side-effects, and their activity in most types of metastatic cancers is limited.

Common forms of cancer include breast cancer and pancreatic cancer.

Breast cancer, in which malignant cells develop in the tissues of the breast, is the most common cancer among women, and the second most common cause of cancer death in women in the United States. Breast tissue is composed of lobes and ducts and also includes blood vessels and lymph vessels, which are connected to lymph nodes. Clusters of lymph nodes are found near the breast in the axilla, under the arm, above the collarbone, and in the chest. Several different types of breast cancer exist, which vary with respect to the types of cells in which they first appear, the symptoms which develop, and how frequently they occur.

Risk factors for breast cancer include older age, early age onset of menstruation, never having given birth, family history (mother or sister) of breast cancer, radiation therapy to the chest, increased density of breast tissue as identified by mammogram, use of hormones such as estrogen and progesterone, frequent alcohol consumption, race-associated factors, and the presence of particular genetic mutations.

In addition, the presence of benign breast disease is associated with an increased risk of breast cancer. Thus, proliferative lesions without atypia are associated with a 1.5- to 2-fold increased risk of breast cancer, whereas atypical hyperplasias are associated with a 4- to 5-fold increased risk. Currently, there are no markers which can predict increased risk of breast cancer among benign breast disease patients.

Breast cancer can metastasize to almost any other part of the body, including the lymph nodes, bones, liver, lungs, and brain. Metastatic breast cancer is incurable with a median survival period of about 2 years. Breast cancers are treated with surgery, radiation therapy, chemotherapy and, according to specific tumor characteristics, may also also be treated with hormonal therapy or antibodies directed against human epidermal growth factor (HER2) protein. Treatment is also administered before (neo-adjuvant) or after (adjuvant) a surgery in which the primary tumor has been removed, in order to prevent disease recurrence. All forms of therapy, including chemotherapy, radiotherapy hormonotherapy and biological therapy may also be used.

Pancreatic cancer is a malignant tumor of the pancreas. Each year about 33,000 individuals in the United States are diagnosed with this condition, and more than 60,000 in Europe. Depending on the extent of the tumor at the time of diagnosis, the prognosis is generally regarded as poor. Median survival from diagnosis is around 3 to 6 months; 5-year survival is much less than 5%; and complete remission is extremely rare. With 37,170 cases diagnosed in the United States in 2007, and 33,700 deaths, pancreatic cancer has the highest fatality rate of all cancers and is the fourth highest cancer killer in the United States among both men and women. Although it accounts for only 2.5% of new cases, pancreatic cancer is responsible for 6% of cancer deaths each year.

Treatment of pancreatic cancer depends on the stage of the cancer, and includes surgical removal of tumors and chemotherapy. The Whipple procedure is the most common surgical treatment for pancreatic cancers. This procedure is a major surgical operation involving the pancreas, duodenum, and other organs, and carries a significant degree of risk.

Patients diagnosed with pancreatic cancer typically have a poor prognosis partly because the cancer usually causes no symptoms early on, leading to locally advanced or metastatic disease at time of diagnosis. As a result of the aggressive invasion and early metastasis characteristics of the disease, 90% of patients have surgically unresectable disease at the time of diagnosis.

Chemotherapeutic agents for treating cancers in general include alkylating agents, antimetabolites, anthracyclines, plant alkaloids, topoisomerase inhibitors, hormone receptor modulators, and hormone level modulators. Chemotherapeutic agents are generally associated with severe side effects, due mainly to the inability of the chemotherapeutic agent to distinguish between normal and healthy cells, such that certain fast-growing, normal cells are also attacked. These include blood cells forming in the bone marrow and cells in the digestive tract (mouth, stomach, intestines, esophagus), reproductive system (sexual organs), and hair follicles. Some chemotherapeutic agents may affect cells of vital organs, such as the heart, kidney, bladder, lungs, and nervous system.

Commonly used chemotherapeutic agents for treatment of pancreatic cancer and breast cancer are taxanes, anthracyclines and antimetabolites such as fluorouracil and gemcitabine. Combination therapy with doxorubicin or mitomycin, may also be used. All of these are associated with side effects. For example, fluorouracil commonly causes diarrhea, mouth ulcers, hair thinning or hair loss, and increased risk of infection; and gemcitabine is associated with nausea, swelling of the feet or legs or weight gain due to fluid retention, flu like symptoms such as headache, chills and fever, and increased risk of infection.

The only therapy currently available for metastatic pancreatic cancer is standard chemotherapy (normally using gencitabine, either alone or in combination with capecitabine, erlotinib or platinum agents), which adds about 1 to 2 months to the median survival time.

When the presence of cancer is suspected in a patient, an imaging study is first performed, such as x-ray, ultrasonography or computed tomography. Imaging studies show the presence, location and size of an abnormal mass, but not whether the mass is cancerous. Cancer can only be positively diagnosed by biopsy, which involves removal of a small tissue sample. The biopsy may be performed using fine needle aspiration, wherein a narrow needle is inserted into a lump or tumor, and cells are withdrawn.

Some types of tumors, including breast tumors, may require an excisional biopsy, wherein a whole lump is surgically removed.

Tissue obtained by biopsy is generally analyzed by microscopic analysis of histological sections, which is a time consuming process, requiring a certain amount of subjective evaluation by the pathologist conducting the analysis.

Given the importance of detecting cancer early in its development, and the potential harm that may occur as a result of false positives or false negatives from mammography and other techniques for screening of various types of cancer, a substantial need remains for a more accurate and less invasive means of determining the presence of cancer. Moreover, currently used techniques cannot predict cancer development among patients with benign breast cancer.

It has therefore been desirable to find a treatment for cancer, such as pancreatic cancer and breast cancer, which overcomes at least some of the drawbacks of the background art.

It is further desirable to find a method of diagnosis of cancer which overcomes at least some of the drawbacks of the background art.

SUMMARY OF THE INVENTION

Some embodiments of the present invention relate to the use of klotho protein and related compounds in the treatment and diagnosis of cancer, such as breast cancer and pancreatic cancer.

According to an aspect of some embodiments of the present invention, there is provided klotho protein or DNA encoding klotho protein for use in the treatment of cancer. According to some embodiments, the klotho protein or DNA is used together with a chemotherapeutic agent.

According to an aspect of some embodiments of the present invention, there is provided for the use of klotho protein or of DNA encoding klotho protein in the manufacture of a medicament for the treatment of cancer, substantially as described in the specification. According to some embodiments, the klotho protein or DNA is used together with a chemotherapeutic agent.

According to an aspect of some embodiments of the present invention, there is provided for the use of a composition comprising a pharmaceutically acceptable amount of a klotho protein or of DNA encoding klotho protein for the treatment of cancer. According to some embodiments, the klotho protein or DNA is used together with a chemotherapeutic agent. According to some embodiments, the composition further comprises a chemotherapeutic agent.

According to an aspect of some embodiments of the present invention, there is provided a method for treating cancer, comprising administering to a subject in need thereof a pharmaceutically effective amount of a composition comprising a klotho protein or a DNA encoding klotho protein. According to some embodiments, the method further comprises co-administration of a chemotherapeutic agent.

According to an aspect of some embodiments of the present invention, there is provided a pharmaceutical composition comprising a klotho protein or DNA encoding klotho protein and a pharmaceutically acceptable carrier for use as a medicament for treating cancer. According to some embodiments, the composition further comprises a chemotherapeutic agent.

According to some embodiments of the present invention, the cancer is an IGF-1 dependent cancer. In some embodiments, the IGF-1 dependent cancer is colon cancer, prostate cancer, lung cancer, cervical cancer or ovarian cancer.

According to some embodiments, the cancer is breast cancer.

According to some embodiments, the cancer is pancreatic cancer.

According to some embodiments, the klotho protein comprises native klotho protein.

According to some embodiments, the klotho protein is a soluble protein.

According to some embodiments, the klotho protein is selected from the group consisting of: a) an isolated polypeptide including the amino acid sequence selected from the group of amino acid sequences represented by SEQ ID NOS: 1, 2, 3, 4, 5, 11, 12, 13, 14 and 15; b) an isolated polypeptide having a homology of at least 80% or more with a polypeptide including the amino acid sequence selected from the group of amino acid sequences represented by SEQ ID NOS: 1, 2, 3, 4, 5, 11, 12, 13, 14 and 15; c) an isolated polypeptide comprising an amino acid sequence wherein at least one amino acid of the amino acid sequence of a polypeptide comprising an amino acid sequence selected from amino acid sequences represented by SEQ ID NOS: 1, 2, 3, 4, 5, 11, 12, 13, 14 and 15 is deleted, substituted or added; and d) an isolated polypeptide comprising an amino acid sequence selected from the group of amino acid sequences represented by residues 31 to 982 of SEQ ID NO: 1, residues 34 to 1012 of SEQ ID NO: 1, residues 34 to 549 of SEQ ID NO: 2 and residues 36 to 1014 of SEQ ID NO: 3. In some embodiments, the homology is of at least 90% or more, at least 95% or more and even of at least 98% or more.

According to some embodiments, the DNA encoding klotho protein is selected from the group consisting of: a) DNA encoding a polypeptide comprising an amino acid sequence selected from the amino acid sequences represented by SEQ ID NOS: 1, 2, 3, 4, 5, 11, 12, 13, 14 and 15 or isolated polypeptides having a homology of at least 80% (in some embodiments, the homology is of at least 90%, at least 95% and even of at least 98%) or more therewith or a DNA encoding a polypeptide comprising an amino acid sequence wherein at least one amino acid of the amino acid sequence of a polypeptide comprising an amino acid sequence selected from amino acid sequences represented by SEQ ID NOS: 1, 2, 3, 4, 5, 11, 12, 13, 14 and 15 is deleted, substituted or added; b) DNA encoding a polypeptide comprising an amino acid sequence selected from the amino acid sequences represented by residues 31 to 982 of SEQ ID NO: 1, residues 34 to 1012 of SEQ ID NO: 1, residues 34 to 549 of SEQ ID NO: 2 and residues 36 to 1014 of SEQ ID NO: 3, and c) DNA comprising a DNA sequence selected from DNA sequences represented by SEQ ID NOS: 6, 7, 8, 9 and 10; d) DNA which hybridizes with a DNA described in (a), (b) or (c) under stringent conditions.

According to some embodiments, the DNA encoding klotho protein is provided inserted in a recombinant vector suitable for gene therapy.

According to some embodiments, the klotho protein or DNA encoding klotho protein is of a form selected from the group consisting of murine, human, bovine, canine or equine forms.

According to some embodiments of methods or uses of the present invention, the klotho protein or DNA encoding klotho protein and the chemotherapeutic agent are administered in a single dosage form. According to some embodiments, the klotho protein or DNA encoding klotho protein and the chemotherapeutic agent are administered sequentially in separate dosage forms.

According to an aspect of some embodiments of the present invention, there is provided a composition comprising a combination of at least two active pharmaceutical ingredients, wherein a first active pharmaceutical ingredient is a klotho protein and a second active pharmaceutical ingredient is at least one chemotherapeutic agent, wherein the amount of the at least one klotho protein alone and the amount of the at least one chemotherapeutic agent alone is insufficient to achieve the therapeutic effect achieved by the administration of the combination of two or more of the agents.

According to an aspect of some embodiments of the present invention, there is provided a method for the diagnosis of cancer in a subject, the method comprising: measuring a level of klotho protein present in a test sample obtained from the subject; and comparing the level of klotho protein in the test sample to that of a reference sample wherein a reduced level of klotho protein in the test sample relative to that of the reference sample is indicative of the presence of cancer in the subject. In some embodiments, a reduced level of klotho protein in the test sample relative to that of the reference sample is indicative of an increased risk for developing cancer.

According to some embodiments, the cancer diagnosed is an IGF-1 dependent cancer, for example, colon cancer, prostate cancer, lung cancer, cervical cancer and ovarian cancer.

According to some embodiments, the diagnosed cancer is breast cancer.

According to some embodiments, the diagnosed cancer is pancreatic cancer.

According to some embodiments, the test sample comprises a biopsy of tissue from a breast tumor, and the reference sample comprises a biopsy of normal breast tissue adjacent to the breast tumor. According to some embodiments, the method is used for screening benign breast disease patients for the presence of breast cancer. According to some embodiments, the method is used for screening benign breast disease patients for evaluating the relative risk of developing of breast cancer.

According to an aspect of some embodiments of the present invention, there is provided a method of predicting the development of cancer in a benign breast disease patient, the method comprising: measuring a level of klotho protein in a test sample obtained from a benign breast lesion; and comparing the level of klotho protein in the test sample to that of a reference sample comprising breast tissue from an area adjacent to the lesion wherein a reduced level of klotho protein in the test sample relative to that of the reference sample is indicative of a relatively higher risk for developing breast cancer.

According to an aspect of some embodiments of the invention, there is also provided a method of treatment, comprising administering to a subject in need thereof a pharmaceutically effective amount of a composition comprising an isolated polypeptide including an amino acid sequence having at least 80% homology to the amino acid sequence represented by SEQ ID NO: 2, or a DNA encoding therefor. SEQ ID NO: 2 corresponds to human KL1.

In some embodiments, the method comprises treatment of cancer, in some embodiments an IGF-1 dependent cancer, in some embodiments, a cancer selected from the group consisting of colon cancer, prostate cancer, lung cancer, cervical cancer and ovarian cancer, in some embodiments breast cancer, and in some embodiments pancreatic cancer.

In some embodiments, the homology is of at least 90%, at least 95% and in some embodiments even of at least 98%.

In some embodiments, the DNA encoding the polypeptide is provided inserted in a recombinant vector suitable for gene therapy.

In some embodiments, the method further comprises co-administration of a chemotherapeutic agent. In some embodiments, the chemotherapeutic agent is selected from the group consisting of alkylating agents, antimetabolites, anthracyclines, plant alkaloids, topoisomerase inhibitors, hormone receptor modulators and hormone level modulators Depending on the embodiment, the polypeptide or DNA encoding therefor and a co-administered chemotherapeutic agent may be administered in a single dosage form or may be administered sequentially in separate dosage forms.

According to an aspect of some embodiments of the invention, there is also provided a pharmaceutical composition comprising an isolated polypeptide including an amino acid sequence having at least 80% homology to the amino acid sequence represented by SEQ ID NO: 2, or a DNA encoding therefor and a pharmaceutically acceptable carrier. As noted above, SEQ ID NO: 2 corresponds to human KL1.

In some embodiments, the homology is of at least 90%, at least 90%, at least 95% and in some embodiments even of at least 98%.

In some embodiments, the composition is configured as an extended release form, which is capable of releasing the polypeptide over a predetermined release period, such that a clinically effective plasma level of the polypeptide is maintained for at least 24 hours, such as at least 48 hours, at least 72 hours, at least one week, and even at least one month.

In some embodiments, the DNA encoding the polypeptide is provided inserted in a recombinant vector suitable for gene therapy.

In some embodiments, the composition further comprises a chemotherapeutic agent in addition to the polypeptide. In some embodiments, the chemotherapeutic agent is selected from the group consisting of alkylating agents, antimetabolites, anthracyclines, plant alkaloids, topoisomerase inhibitors, hormone receptor modulators and hormone level modulators.

According to an aspect of some embodiments of the invention there is also provided a composition comprising a combination of at least two active pharmaceutical ingredients, wherein a first active pharmaceutical ingredient is a klotho protein and a second active pharmaceutical ingredient is at least one chemotherapeutic agent, wherein the amount of the at least one klotho protein alone and the amount of the at least one chemotherapeutic agent alone is insufficient to achieve the therapeutic effect achieved by the administration of the combination of two or more of the agents; and wherein the klotho protein is an isolated polypeptide including an amino acid sequence having at least 80% homology to the amino acid sequence represented by SEQ ID NO: 2, or a DNA encoding therefor and a pharmaceutically acceptable carrier. In some embodiments, the homology is of at least 90%, at least 90%, at least 95% and in some embodiments even of at least 98%. In some embodiments, the chemotherapeutic agent is selected from the group consisting of alkylating agents, antimetabolites, anthracyclines, plant alkaloids, topoisomerase inhibitors, hormone receptor modulators and hormone level modulators. In some embodiments, the composition is configured as an extended release form, which is capable of releasing the polypeptide over a predetermined release period, such that a clinically effective plasma level of the polypeptide is maintained for at least 24 hours, such as at least 48 hours, at least 72 hours, at least one week, and even at least one month. In some embodiments, the DNA encoding the polypeptide is provided inserted in a recombinant vector suitable for gene therapy.

Unless otherwise defined, all technical and scientific terms used herein have the same meaning as commonly understood by one of ordinary skill in the art to which this invention pertains. In case of conflict, the patent specification, including definitions, will control.

As used herein, the term "treating" includes curing a condition, treating a condition, preventing a condition, treating symptoms of a condition, curing symptoms of a condition, ameliorating symptoms of a condition, treating effects of a condition, ameliorating effects of a condition, and preventing results of a condition.

As used herein, the terms "comprising". "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more" unless the context clearly dictates otherwise.

BRIEF DESCRIPTION OF THE FIGURES

Some embodiments of the invention are herein described, by way of example only, with reference to the accompanying figures. The description, together with the figures, makes apparent how embodiments of the invention may be practiced to those skilled in the art. It is stressed that the particulars shown in the figures are by way of example and for purposes of illustrative discussion of embodiments of the invention.

In the figures.

DESCRIPTION OF SOME EMBODIMENTS OF THE INVENTION

Figure 1:
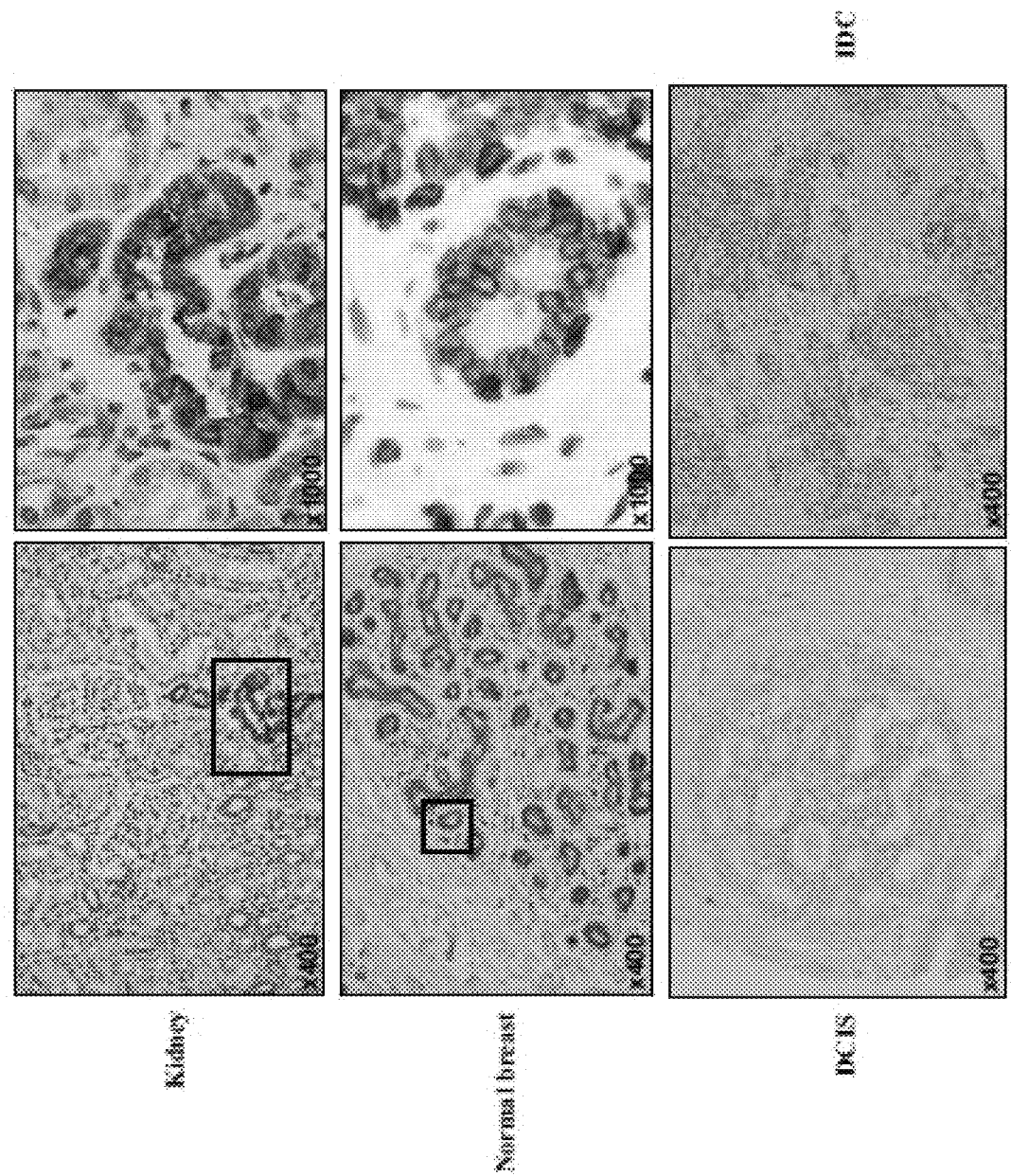
FIG. 1 shows immunohistochemical staining of klotho protein. Upper panel: Kidney section [magnifications: ×400, left and ×1000, right]. Middle panel: normal breast, shown at ×400, left and x 1000 magnifications. Lower panel, Ductal carcinoma in situ (DCIS, left) and invasive ductal carcinoma (IDC, right)

The present invention, in some embodiments, relates to the field of therapeutics, and more specifically to the use of klotho protein and related compounds for treatment and for diagnosis, for example of cancer. In some embodiments, the cancer is an IGF-1 dependent cancer, for example, colon cancer, prostate cancer, lung cancer, cervical cancer, ovarian cancer, but especially breast cancer and pancreatic cancer.

The klotho protein gene was identified as a potent suppressor of aging (Kuro-o et al., 1997). Mice homozygous for a mutated klotho protein allele exhibit a syndrome resembling human aging and suffer from osteoporosis, atherosclerosis and a short lifespan; while klotho protein over-expression extends lifespan and is associated with reduced fertility and insulin resistance (Kuro-o et al., 1997; Kurosu et al., 2005).

Anti-aging pharmaceutical compositions including klotho protein (human and murine) as well as DNA encoding this protein have been described in PCT/JP1997/004585 (published, inter alia, in EP 0 945 506 B1) which is included by reference as if fully set forth herein.

Compositions for reducing or increasing phosphorus and/or vitamin D level in blood, used for preventing and/or treating osteoporosis or rachitis, comprising klotho protein or anti-klotho protein antibody have been described in PCT/JP2004/006899 published as WO2004/100976.

Klotho protein (for example, SEQ ID NO: 1 from human kidney or SEQ ID NO: 3 from murine kidney) is a single pass transmembrane protein located at the cell membrane (Ito et al., 2000; Kuro-o et al., 1997; Matsumura et al., 1998; Shiraki-Iida et al., 1998) and also detected in the Golgi apparatus (Imura et al., 2007). Human Klotho protein (full-length (FL)-hKL; seq ID: 1) is 1012 amino acid residues long while murine Klotho protein (full-length (FL)-mKL; seq ID: 3) is 1014 amino acid residues long. Human Klotho protein is anchored in a cell membrane through the C-terminus (residues 981-1012).

The extracellular domain of klotho protein is composed of two spherically-folded domains, KL1 (in humans, residues 29-568, 540 residues long, seq ID: 2) and KL2 (in humans, residues 569-980, 411 residues long), which share amino acid sequence homology to β-glucosidase but lacks glucosidase catalytic activity (Kuro-o et al., 1997). The N-terminus of human Klotho protein (residues 1-28) trails from KL1. KL1 may also be transcribed through an alternative splicing (1.5). It is known that in vivo, KL1 and KL2 can be cleaved together to form a single 130 kDa secreted klotho protein, also called soluble klotho protein, (sol-hKL or sol-mKL) which is shed into the serum and act as a circulating hormone (Imura et al., 2004), or can be cleaved separately as a 68 kDa protein (KL11). The 64 kDa protein (KL2) was not detected in body fluids. It has been shown recently that A Desintegrin and Metalloproteinase (ADAM) 10 and 17 participate in this process in response to insulin stimulation (Chen et al., 2007).

Only full length klotho can function as a co-receptor for FG23 (Kurosu et al., 2006; Wu et al., 2008).

Secreted Klotho protein (sol-hKL) has been implicated in a number of biological activities including: a humoral factor that regulates activity of multiple glycoproteins on the cell surface including ion channels and growth factor receptors such as insulin/insulin-like growth factor-1 receptors.

mRNA expression analysis identified klotho protein mainly in the distal renal tubules and the choroid plexus in the brain, but also in sex-hormone-responsive tissues including the placenta, testes and ovaries (Kuro-o et al., 1997; Ohyama et al., 1998; Shiraki-Iida et al., 1998). The expression of klotho protein in breast or pancreatic tissue has not hitherto been explored.

Klotho protein-modulated receptors include the insulin receptor (IR) (Kuro-o et al., 1997), the IGF-1 receptor (IGF-1R) and several fibroblast growth factor receptors (FGFR), but not the epidermal growth factor receptor (EGFR) (Kurosu et al., 2006; Urakawa et al., 2006). Treatment of cultured cells with soluble klotho protein inhibited insulin-induced glucose uptake, and reduced stimulation-induced phosphorylation of the IR, the IGF-IR and the insulin receptor substrates (IRS)-1 and -2 (Kurosu et al., 2005). Moreover, klotho protein-deficient mice are hypoglycemic and extremely sensitive to insulin (Kuro-o et al., 1997; Utsugi et al., 2000), while klotho protein over-expressing mice are associated with insulin resistance (Kurosu et al., 2005). Klotho protein also functions as an obligate co-receptor for FGF23, a bone-derived hormone that induces phosphate excretion into urine. Mice lacking klotho protein, and/or FGF23 not only exhibit phosphate retention but also display a premature-aging syndrome, revealing an unexpected link between phosphate metabolism and aging. Klotho protein inhibits activation of the FGFRs by bFGF in human embryonic kidney (HEK) 293 and COS7 cells (Wolf et al., 2008; Urakawa et al., 2006; Kurosu et al., 2006).

Klotho protein-induced inhibition of the IGF-1R may also affect the expression of the transcription factors CCAAT/enhancer-binding protein (C/EBP) α and β. These factors are down-regulated by the IGF-1 pathway and were recently identified as breast cancer growth suppressors (Gery et al., 2005; Gomis et al., 2006; Wolf et al., 2006a). The C/EBP family is involved in adipocyte differentiation and klotho protein-deficient mice have barely detected amounts of white adipose tissue (Kuro-o et al., 1997). Indeed, klotho protein has been identified recently as an inducer of adipocyte differentiation, and this activity is mediated through up-regulation of these transcription factors (Chihara et al., 2006).

Klotho protein may play a role in human diseases, and klotho protein polymorphism was associated with reduced life span, coronary heart disease and osteoporosis (Arking et al., 2003; Arking et al., 2002; Kim et al., 2006; Zarrabeitia et al., 2007).

Klotho protein has been shown to affect the activity of several signaling pathways, which may participate in breast cancer tumorigenesis, through modulation of ligand-dependent activation of their specific membranal receptors. Increased serum insulin levels are associated with adverse prognosis in breast cancer, high circulating IGF-1 levels are associated with increased risk of premenopausal breast cancer, and inhibition of the insulin and IGF-1 pathways inhibits growth of breast cancer cells (Bartucci et al., 2001; Wolf et al., 2006b; Yee, 2006).

Klotho protein expression and activities in breast cancer has never before been elucidated. As klotho protein is expressed in various hormone-responsive tissues, and as klotho protein activity is associated with inhibition of the IGF-1 and insulin pathways, it was considered by the present inventors that klotho protein may have tumor suppressor activities in breast cancer.

The present inventors have identified high klotho protein expression in normal breast tissue and low klotho protein expression in breast cancer; noted inhibition of breast cancer cell growth following over-expression of klotho protein, and growth enhancement of klotho protein-expressing cells following klotho protein knock-down; and revealed modulation of the IGF-1 and the insulin pathways by klotho protein. Taken together, the results suggest klotho protein as a novel breast cancer tumor suppressor.

Insulin like growth factor-1 (IGF-1) is also a powerful mediator of pancreatic cancer. Both IGF-1 and IGF-1 receptor (IGF-IR) are overexpressed in human pancreatic tumors as well as in pancreatic cancer cell lines (Bergmann, U., et al, 1995, Karna. E., et al, 2002). Blockage of the IGF-1RR by a dominant negative inhibitor suppresses tumorigenicity both in vitro and in vivo and increase sensitivity of pancreatic tumors to radiation and chemotherapy-induced apoptosis (Edderkaoui, M., et al. 2007). Thus, the inventors consider that the IGF-1 pathway may serve as an attractive target for novel therapies against pancreatic cancer.

Klotho protein has previously been identified as an inhibitor of the IGF-1 system in hepatocytes and muscle cells. The effects of klotho protein on inhibition of the IGF-1 system in cancer cells, such as pancreatic and breast cancer cells, have not hitherto been studied.

The present inventors have found that klotho protein has an inhibitory effect on growth of cell lines, including breast cancer cell lines and pancreatic cancer cell lines. This is exceptionally surprising and entirely unexpected in light of the fact that Klotho protein has been demonstrated to have an anti-senescence and anti-apoptotic activity.

Immunohistochemistry analysis of klotho protein expression in both pancreatic cells and breast tissue arrays revealed high levels of klotho protein expression in normal breast samples and normal pancreatic cells, but very low expression in cancerous breast cells or cancerous pancreatic cells. In cancer samples, high klotho protein expression was associated with smaller tumor size and reduced K167 staining.

Forced expression of klotho protein reduced proliferation of MCF-7 and MDA-MB-231 breast cancer cells, while klotho protein silencing in MCF-7 cells, which normally express klotho protein, enhanced proliferation. Moreover, forced expression of klotho protein in these cells inhibited ligand-dependent IGF-1 and insulin pathways activation, and induced upregulation of the transcription factor CCAAT/enhancer-binding protein (C/EBP) 13, a breast cancer growth inhibitor which is negatively regulated by the IGF-1-AKT axis. Co-immunoprecipitation revealed an interaction between klotho protein and the IGF-1 receptor. Klotho protein did not affect activation of the epidermal growth factor pathway.

Over-expression of klotho protein was similarly found to inhibit growth of pancreatic cell lines Panc1, Colo357 and Mia Paca, and to inhibit the IGF-1 pathway in Panc1 cells, by inhibition of phosphorylation of the IGF-1 receptor, and its downstream targets AKT1 and ERK1/2.

These data suggest klotho protein as a potential tumor suppressor and identify it as an inhibitor of the IGF-1 pathway, for example in human breast cancer or pancreatic cancer. Insulin like growth factor-1 (IGF-1) is also a powerful mediator of other cancers, such as colon cancer, lung cancer, ovarian cancer, cervical cancer and prostate cancer. Thus, the data found by the Inventors suggest that klotho protein as a potential tumor suppressor in IGF-1 dependent cancers in addition to human breast cancer or pancreatic cancer, for example colon cancer, lung cancer, ovarian cancer, cervical cancer and prostate cancer.

Treatment, for Example of Cancer

Thus, as discussed herein and as described in detail in the Examples section below, it has been surprisingly found by the present inventors that klotho protein and related compounds are useful in affecting cancer cells and therefore in the treatment of cancer.

According to some embodiments, the present invention therefore provides use of klotho protein (including related compounds such as a fragment, an analog, a mimetic, a derivative or salt thereof) as a therapeutic agent for the treatment of cancer.

In some embodiments the present invention provides a method of treatment of cancer comprising administering to a subject in need thereof a pharmaceutically effective amount of a klotho protein.

In some embodiments, the present invention further provides the use of a composition comprising a pharmaceutically acceptable amount of a klotho protein for the treatment of cancer.

Some embodiments of the present invention are based on the surprising discovery that isolated polypeptides including an amino acid sequence having at least 80% (in some embodiments at least 90%, at least 95% and even of at least 98%) homology to the amino acid sequence represented by SEQ ID NO: 2 (KL1), or DNA encoding thereof, are effective as medicaments, especially for treating cancer, and/or when administered to a subject cause relatively few and/or less severe unwanted side effects. Herein, such polypeptides are called "KL1 analogues".

Types of Cancer

In some embodiments, the cancer is an IGF-1 dependent cancer. According to some aspects of embodiments of the present invention, the cancer is selected from the group consisting of breast cancer, pancreatic cancer, colon cancer, lung cancer, cervical cancer, ovarian cancer, and prostate cancer. According to some embodiments of the present invention, the cancer is breast cancer, According to some embodiments of the present invention, the cancer is pancreatic cancer.

According to some embodiments of the present invention, the cancer may be metastatic cancer.

Klotho Protein

The klotho protein may be any suitable klotho protein and may be made, isolated, and purified in any suitable fashion with which one skilled in the art, for example as described hereinbelow or in PCT/JP1997/004585 (published, inter alia, in EP 0 945 506 B1). Specific representative examples of klotho proteins suitable for use in implementing some embodiments of the teachings of the present invention include proteins described herein and in PCT/JP1997/004585

In some embodiments, a klotho protein used in implementing the teachings of the present invention is a complete, or substantially complete, full-length klotho protein (FL-KL). Typical such complete klotho proteins are isolated polypeptides including the amino acid sequence selected from the group of amino acid sequences represented by SEQ ID NOS: 1, 3, 5, and 11. Although not wishing to be held to any one theory, it is believed that in some embodiments, a complete or substantially complete klotho protein that is administered to a subject is modified in the body of a subject (for example by cleavage of at least one peptide bond, shortening of the N-terminus and/or shortening of the C-terminus) and the thus-modified polypeptide provides the desired effect, e.g., treating cancer.

In some embodiments, a klotho protein used in implementing the teachings of the present invention is a cleaved extracellular portion of a complete klotho protein. Typical such extracellular portions of a klotho protein are isolated polypeptides including the amino acid sequence selected from the group of amino acid sequences represented by SEQ ID NOS: 2 (KL1), 4, 12 and 13.

In some embodiments, a klotho protein used in implementing the teachings of the present invention is a portion of a complete klotho protein. Typical such portions of complete klotho proteins are isolated polypeptides including the amino acid sequence selected from the group of amino acid sequences represented by SEQ ID NOS: 14, 15 as well as solubilized klotho protein, see below.

In some embodiments, a klotho protein used in implementing the teachings of the present invention is a solubilized klotho protein, for example solubilized by removal of one or more amino acid residues from the C-terminus, the N-terminus or both the C-terminus and the N-terminus, as is known to one skilled in the art and as described, for example, in Kurosu et al., 2005. Typical such solubilized klotho proteins are isolated polypeptides including an amino acid sequence selected from the group of amino acid sequences represented by residues 31 to 982 of SEQ ID NO: 1 (see experimental section below), residues 34 to 1012 of SEQ ID) NO: 1 (as disclosed in PCT/JP1997/004585), residues 34 to 549 of SEQ ID NO: 2 (KL1, as disclosed in PCT/JP1997/004585) and residues 36 to 1014 of SEQ ID NO: 3 (as disclosed in PCT/JP1997/004585).

In some embodiments, a klotho protein used in implementing the teachings of the present invention is an isolated polypeptides having a homology of at least 80% or more (e.g., at least 90%, at least 95% and even at least 98% homology) with a polypeptide including the amino acid sequence selected from the group of amino acid sequences represented by any of SEQ ID NOS: 1 to 5 or 11 to 15.

In some embodiments, a klotho protein used in implementing the teachings of the present invention is an isolated polypeptide comprising an amino acid sequence wherein at least one amino acid of the amino acid sequence of a polypeptide comprising an amino acid sequence selected from amino acid sequences represented by SEQ ID NOS: 1 to 5 or 11 to 15 is deleted, substituted or added.

It is important to note that in some embodiments it is preferred that a klotho protein administered to a subject be allogeneic (from the same species as the subject) as opposed to heterologous. For example, for treating cancer in humans, in some embodiments it is preferred to use a human klotho protein (e.g., SEQ ID NOS: 1, 2, 5 or 11 to 15). For example, for treating cancer in a mouse, in some embodiments it is preferred to use a murine klotho protein (e.g., SEQ ID NOS: 3 or 4).

According to some embodiments of the present invention, the klotho protein is a native protein, a derivative or analog thereof, or an active segment of the native protein.

According to some embodiments of the present invention, the klotho protein is a soluble or solubilized form of klotho protein.

According to some embodiments, the Klotho protein is a pegylated klotho protein, for example, a protein substantially similar or identical to klotho proteins described herein that has been pegylated to improve pharmacokinetics or other parameters. Various advantages of pegylation and methods for pegylation of proteins such as klotho proteins are known in the art, see for example Ryan S M, Mantovani G, Wang X, Haddleton D M, Brayden D J "Advances in PEGylation of important biotech molecules: delivery aspects" in Expert Opin Drug Deliv. 2008, 0.5(4), 371-383.

Specific examples of klotho proteins suitable for implementing some embodiments of the teachings of the present invention are described herein with reference to the amino acid sequences in the appended sequence listing. The thus-described listed klotho proteins are summarized:

| SEQ ID NO: | species/source | AA residues | accession no. |
| --- | --- | --- | --- |
| 1* | human kidney | 1012 | AAQ41828 |
| 2* | human kidney | 549 | AAQ41829 |
| 3* | mouse kidney | 1014 | AAQ41830 |
| 4* | mouse kidney | 550 | AAQ41831 |
| 5* | human pancreas | 1015 | AAQ41832 |
| 11 | human | 1012 | EAX08526 |
| 12 | human | 549 | BAA24941 |
| 13 | human | 549 | EAX08525 |

-continued

| SEQ ID NO: | species/source | AA residues | accession no. |
|---|---|---|---|
| 14 | human | 273 | CAC94767 |
| 15 | human | 739 | CAC94773 |

*fully described in PCT/JP1997/004585

Administration

The klotho protein (especially KL1 or KL1 analogue) may be administered by any suitable route, for example as described in PCT/JP1997/004585. For example, the klotho protein (especially KL1 or KL1 analogue) may be administered by parenteral (including intravenous, intradermal, intraperitoneal, intramuscular and subcutaneous) routes. Alternatively, the klotho protein (especially KL1 or KL1 analogue) may be administered by other delivery routes, including oral, nasal, buccal, sublingual, intra-tracheal, transdermal, transmucosal, and pulmonary. The klotho protein (especially KL1 or KL1 analogue) may be administered by continuous release or delivery, using, for example, an infusion pump, continuous infusion, controlled release formulations utilizing polymer, oil or water insoluble matrices.

Carriers or excipients known in the art can also be used to facilitate administration of the klotho protein (especially KL1 or KL1 analogue). Examples of carriers and excipients include calcium carbonate, calcium phosphate, various sugars such as lactose, or types of starch, cellulose derivatives, gelatin, vegetable oils, polyethylene glycols and physiologically compatible solvents.

According to some embodiments, the klotho protein (especially KL1 or KL1 analogue) is administered in extended release form, which is capable of releasing the protein over a predetermined release period, such that a clinically effective plasma level of the klotho protein (especially KL1 or KL1 analogue) is maintained for at least 24 hours, such as at least 48 hours, at least 72 hours, at least one week, or at least one month.

According to some embodiments of the present invention, the klotho protein (especially KL1, or KL1 analogue) may be administered in combination with one or more chemotherapeutic agents, including, for example, alkylating agents, antimetabolites, anthracyclines, plant alkaloids, topoisomerase inhibitors, hormone receptor modulators, hormone level modulators, and other antitumour agents.

Examples of suitable alkylating agents include, without limitation, busulfan, carboplatin, carmustine, cisplatin, chloroambucil, cyclophosphamide, dacarbazine, hexamethylmelamine, ifosfamide, mechlorethamine, melphalan, oxoplatin, streptozocin, temozolomide, thiotepa, and uramustine.

Non-limiting examples of suitable antimetabolites include azathioprine, capecitabine, carmofur, cladribine, clofarabine, cytarabine, fludarabine, fluorouracil, gemcitabine, mercaptopurine, methotrexate, premetrexed, raltitrexed, tegafur, and tioguanine.

Suitable anthracyclines include, for example, daunorubicin, doxorubicin, epirubicin, idarubicin, mitoxantrone and valrubicin.

Examples of suitable plant alkaloids include docetaxel, paclitaxel, vinblastine, vincristine, vindesine, and vinorelbine. Examples of suitable topoisomerase inhibitors include include amsacrine, etoposide, etoposide phosphate, irinotecan, teniposide, and topotecan. Examples of suitable hormone receptor modulators include tamoxifen; and estrogen antagonists, such as faslodex. Examples of suitable hormone level modulators include aromatose inhibitors, such as letrozole, anastrazole and aromasin. Examples of other antitumor agents include dactinomycin, and other chemotherapeutic agents for treatment of obesity-related cancers, such as trastuzumab (herceptin), lapatinib, bevacizumab (avastin), cetuximab (erbitux), panitumumab, erlotinib, and sunitinib.

Preferably, the klotho protein (especially KL1 or KL1 analogue) and the chemotherapeutic agent are administered by subcutaneous or intravenous injection.

The chemotherapeutic agent may optionally be provided in a combined dosage form, together with the klotho protein. Alternatively, the chemotherapeutic agent may be provided in a separate dosage form, for co-administration or sequential administration, either before or after administration of the klotho protein.

The present invention further provides a composition comprising pharmaceutically acceptable amounts of a klotho protein (especially KL1 or KL1 analogue) and a chemotherapeutic agent as an additional active pharmaceutical ingredient.

The composition may optionally be provided in extended-release form, as described above with regard to the klotho protein alone.

According to some embodiments of the present invention, there is provided a composition comprising a combination of at least two active pharmaceutical ingredients, at least one of which is a klotho protein (especially KL1 or KL1 analogue) and at least one of which is a chemotherapeutic agent, wherein the amount of klotho protein (especially KL1 or KL1 analogue) and amount of the chemotherapeutic agent alone is insufficient to achieve the therapeutic effect achieved by the administration of the combination of two or more of the active pharmaceutical ingredients. The composition of the present invention comprises, in addition to the active pharmaceutical ingredients, a pharmaceutically acceptable carrier, and may optionally further comprise one or more pharmaceutically acceptable excipients.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered subcutaneously. Saline solutions and aqueous dextrose and glycerol solutions can also be employed as liquid carriers, particularly for injectable solutions.

If desired, solutions of the above dosage compositions may be thickened with a thickening agent such as methylcellulose. They may be prepared in emulsified form, such as either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

In general, the composition of the present invention is prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH-1 or an additional solute to control tonicity.

Treatment Using Gene Therapy

Discussed above were various embodiments of the present invention where a klotho protein (especially KL1 or KL1 analogue), a polypeptide, was administered to a subject in order to treat cancer. In some embodiments, rather than administering a polypeptide, gene therapy is used, whereby a DNA encoding for a klotho protein (especially KL1 or KL1 analogue) is administered, in the usual way, to a subject. The thus-administered DNA causes the body of the subject to produce endogenous klotho protein (especially KL1 or KL1 analogue) in amounts sufficient to lead to the desired anti-cancer effect. In some embodiments, the DNA is delivered inserted in a recombinant vector (e.g., a bacteria) suitable for gene therapy.

Thus, according to some embodiments, the present invention therefore provides use of DNA-encoding for klotho protein (especially KL1 or KL1 analogue) (or related compounds) as a therapeutic agent for the treatment of cancer.

In some embodiments the present invention provides a method of treatment of cancer comprising administering to a subject in need thereof DNA encoding klotho protein (especially KL1 or KL1 analogue) or related compound, e.g., a fragment, an analog, a mimetic or a derivative thereof.

In some embodiments, the cancer is an IGF-1 dependent cancer. According to some aspects of embodiments of the present invention, the cancer is selected from the group consisting of breast cancer, pancreatic cancer, colon cancer, lung cancer, cervical cancer, ovarian cancer, and prostate cancer. According to some embodiments of the present invention, the cancer is breast cancer. According to some embodiments of the present invention, the cancer is pancreatic cancer.

According to some embodiments of the present invention, the cancer may be metastatic cancer.

The DNA encoding klotho protein (especially KL1 or KL1 analogue) may be a DNA for encoding any suitable klotho protein (especially KL1 or KL1 analogue) and may be made, isolated, purified, and provided in any suitable fashion with which one skilled in the art, for example as described in PCT/JP1997/004585 (published, inter alia, in EP 0 945 506 B1). For example, as is well known to one skilled in the art, a preferred way of providing a protein-encoding DNA, such as DNA encoding klotho protein (especially KL1 or KL1 analogue), is by inserting the DNA in a recombinant vector, especially a recombinant vector suitable for gene therapy.

In some embodiments, the DNA encoding klotho protein is a DNA encoding a polypeptide comprising an amino acid sequence selected from the amino acid sequences represented by SEQ ID NOS: 1, 2, 3, 4 and 5 or isolated polypeptides having a homology of at least 80% or more therewith (e.g., at least 90%, at least 95% and even at least 98% homology therewith) or a DNA encoding a polypeptide comprising an amino acid sequence wherein at least one amino acid of the amino acid sequence of a polypeptide comprising an amino acid sequence selected from amino acid sequences represented by SEQ ID) NOS: 1, 2, 3, 4 and 5 is deleted, substituted or added.

In some embodiments, the DNA encoding klotho protein is a DNA comprising a DNA sequence selected from DNA sequences represented by SEQ ID NOS: 6, 7, 8, 9 and 10.

In some embodiments, the DNA encoding klotho protein is a DNA which hybridizes with a DNA described above under stringent conditions. By "DNA which hybridizes under stringent conditions" is meant DNA obtained by colony hybridization, plaque hybridization or Southern blot hybridization using DNA encoding klotho protein, specifically including DNA identified after hybridization, using a filter on which colony- or plaque-derived DNA has been immobilized in the presence of 0.7 to 1.0 M NaCl at 65° C. and washing the resulting filter using 0.1 to 2×SSC solutions (the composition of 1×SSC solution comprises 150 mM sodium chloride and 15 mM sodium citrate) at 65° C.

Hybridization can be carried out according to a method described, for example, in Molecular Cloning, A Laboratory Manual, the 2nd edition (Sambrook, Fritsch, & Maniatis eds., Cold Spring Harbor Laboratory Press, 1989). Specific examples of the DNA which hybridizes include DNA having a homology of 60% or more with a nucleotide sequence of the DNA encoding the polypeptide of an amino acid sequence selected from amino acid sequences represented by SEQ ID NOS: 1, 2, 3, 4 and 5, preferably DNA having a homology of 80% or more, and more preferably DNA having a homology of 95% or more.

It is important to note that in some embodiments it is preferred that the DNA administered to a subject encode allogeneic (from the same species as the subject) klotho protein, as opposed to heterologous klotho protein. For example, for treating cancer in humans, in some embodiments it is preferred to use a DNA encoding for human klotho protein (e.g., SEQ ID NOS: 6, 7 or 10). For example, for treating cancer in a mouse, in some embodiments it is preferred to use a DNA encoding for murine klotho protein (e.g., SEQ ID NOS: 8 or 9).

Specific examples of nucleic acids suitable for implementing some embodiments of the teachings of the present invention are described herein with reference to the nucleic acid sequences in the appended sequence listing. The thus-described listed nucleic acids are summarized:

| SEQ ID NO: | encoding a polypeptide comprising an amino acid sequence represented by: | Accession nr. |
|---|---|---|
| 6* | SEQ ID NO: 1 | AR343616 |
| 7* | SEQ ID NO: 2 | AR343617 |
| 8* | SEQ ID NO: 3 | AR343618 |
| 9* | SEQ ID NO: 4 | AR343619 |
| 10* | SEQ ID NO: 5 | AR343620 |

*fully described in PCT/JP1997/004585

The DNA encoding for klotho protein (especially KL1 or KL1 analogue) may be administered by any suitable route, for example as described in PCT/JP1997/004585. For example, in some embodiments the DNA is provided inserted in a recombinant vector (e.g., a bacteria), and the vector administered by parenteral routes.

According to some embodiments of the present invention, the DNA encoding for klotho protein (especially KL1 or KL1 analogue) may be administered in combination with one or more chemotherapeutic agents, as discussed above for administration of klotho protein as a polypeptide As noted above, in some embodiments, the teachings of the present invention (e.g., administration of a klotho protein, especially KL1 or KL1 analogue) as a polypeptide or of DNA encoding therefore) are directed to treating cancer for example, to reduce or eliminate cancerous tumors and metastatic cells and tumors.

In some embodiments, the teachings of the present invention (e.g., administration of a klotho protein, especially KL1 or KL1 analogue) as a polypeptide or of DNA encoding therefore) are implemented to treat cancer as an adjuvant treatment, that is to say together with known modalities of cancer treatment.

In some embodiments, the teachings of the present invention (e.g., administration of a klotho protein, especially KL1 or KL1 analogue) as a polypeptide or of DNA encoding therefore) are implemented to treat cancer as a neo-adjuvant treatment, for example to reduce the size of a tumor prior to surgical excision thereof.

In some embodiments, the teachings of the present invention are implemented prophylactically (e.g., administration of a klotho protein, especially KL1 or KL1 analogue) as a polypeptide or of DNA encoding therefore). For example, in some embodiments, the present invention is implemented on a person who has not yet been diagnosed with cancer but is a member of a group at high risk of being diagnosed with cancer, for example has a genetic inclination to cancer (family history), a pathological indication of pre cancer (e.g., pre breast cancer), DCIS (ductal carcinoma in situ), clinically significant alcohol use, age or use of HRT (hormone replacement therapy). For example, in some embodiments, the present invention is implemented on a person whose cancer is in remission (complete or partial) but may be susceptible to a return of the disease.

Diagnosis

The present inventors have further surprisingly found that reduced expression of klotho protein correlates with increased tumor proliferative index, which provides an indication of the number of cells that are actively growing. A low proliferative index is associated with a slower growth rate.

In invasive ductal carcinomas, low klotho protein expression was associated with larger tumor size and higher expression of the cell proliferation marker, K167. Thus, it appears that klotho protein expression is down-regulated in the early stages of breast cancer development, such that low or decreased klotho protein expression may serve as a maker of breast cancer.

According to some embodiments of the present invention, there is provided a method for the diagnosis of cancer, comprising assaying the level of klotho protein present in a test sample obtained from a patient, and comparing the level of klotho protein to that of a reference sample, wherein a decreased level of klotho protein in the test sample, relative to that of the reference sample, is indicative of the presence of cancer in the patient.

According to some aspects of this embodiment of the present invention, the cancer is an IGF-dependent cancer, for example, breast cancer, pancreatic cancer, colon cancer, lung cancer, cervical cancer, ovarian cancer, or prostate cancer. According to some aspects of this embodiment of the present invention, the cancer is breast cancer or pancreatic cancer.

In embodiments, the test sample comprises a biopsy of tissue from a tumor, and the standard sample comprises a biopsy of normal tissue taken from an area adjacent to the tumor. Decreased klotho protein expression in the tumor tissue as opposed to the normal tissue indicates that the tumor is cancerous. For example, in embodiments wherein the cancer to be diagnosed is breast cancer, the test sample comprises a biopsy of tissue from a breast tumor, and the standard sample comprises a biopsy of normal breast tissue taken from an area adjacent to the breast tumor. Decreased klotho protein expression in the tumor tissue as opposed to the normal breast tissue indicates that the tumor is cancerous.

According to some embodiments of the present invention, there is provided a method of predicting the development of cancer in a benign breast disease patient, the method comprising measuring a level of klotho protein in a test sample obtained from a benign breast lesion; and comparing the level of klotho protein in the test sample to that of a reference sample comprising breast tissue from an area adjacent to the lesion; wherein a reduced level of klotho protein in the test sample relative to that of the reference sample is indicative of the presence of cancer in the patient or, in embodiments, is indicative of an increased risk for developing of cancer in the patient.

Exemplary embodiments of the invention are discussed hereinbelow with reference to specific materials, methods and examples. The material, methods and examples discussed herein are illustrative and not intended to be limiting. In some embodiments, methods and materials similar or equivalent to those described herein are used in the practice or testing of embodiments of the invention. It is to be understood that the invention is not necessarily limited in its application to the details of construction and the arrangement of the components and/or methods set forth in the following description and/or illustrated in the drawings. The invention is capable of other embodiments or of being practiced or carried out in various ways.

EXAMPLES

Materials and Methods

Chemicals, Antibodies and Constructs:

Insulin, EGF, and 5-fluororacil (5-FU) were obtained from Sigma-Aldrich Corporation (St. Louis, Mo., USA), bFGF was obtained from Biological industries (Kibbutz Beit Haemek, Israel). IGF-1 was obtained from PeproTech Inc (Rocky Hill, N.J.), G418 from Invitrogen (Carlsbad, Calif.), and gemcitabine from Eli Lilly and Company (Indianapolis, Ind., USA). Antibodies used in this study: anti-p53, -PARP, -IGF-3 receptor, and -C/EBPβ (Santa Cruz Biotechnology, Santa Cruz, Calif.), anti-phospho-AKT1 (S473), phospho-IGF-1R (Y1131), phospho-IR (Y1146) total pan-AKT, pGSK3β (S9) (Cell Signaling Technology, Danvers, Mass.), anti-diphosphorylated and -total ERK 1/2 (Sigma), total IRS1 from Upstate Chemicon (Temecula, Calif., USA), phospho-IRS1. (Invitrogen), anti-HA (Covance, Princeton, N.J., USA), anti klotho (Calbiochem International, San Diego, Calif., USA). The klotho protein (for klotho having SEQ ID NO. 3) expression vector was a generous gift of Y. Nabeshima (Kyoto University, Japan). Soluble human Klotho protein (hKL) and soluble murine klotho protein were obtained from R&D Systems (Minneapolis, Minn. USA). Additional murine klotho (termed mKlotho) was produced by the inventors using S2 *Drosophila* expression system. Human KL1 (hKL1) (residues 34-549 of SEQ ID: 2) was obtained from PeproTech Inc. (Rocky Hill, N.J., USA).

siRNA:

Klotho protein directed stealth siRNA duplex oligoribonucleotides and control siRNAs were both designed and purchased from Invitrogen. Lipofectamine 2000 (Invitrogen), and was used to transfect the cells with 100 pmoles of siRNA.

```
Si-1, directed against 1039-1063:
ACCUUUCAUCUAUUCUGCCUGAUUU

Si-2, directed against 1187-1211:
CCUGAGGCAACUGCUUUCCUGGAUU

Si-3, directed against 1274-1298:
CACCAAGAGAGAUGAUGCCAAAUAU

Si-C, scrambled:
CACGAGAUAGAGUAGAACCAACUAU
```

Tissue Arrays and Immunohistochemistry Analysis:

Breast cancer tissue arrays were created, after IRB approval, from cancers diagnosed at Cedars-Sinai Medical Center from 1991 to 1998. Clinical parameters and follow-up information were obtained from hospital records. The tissue arrays were constructed using a manual arrayer (Beecher Instruments, MD) and contained three 1 mm samples for each specimen. For immunohistochemistry analysis, five-micron sections were cut from the tissue array. The slides were deparaffinized through xylenes and graded ethyl alcohols and then rinsed in water, followed by quenching of endogenous peroxidase activity by a 30% solution of hydrogen peroxidase in methanol for 10 minutes. Antigen retrieval was performed by boiling the slides in 0.01 mol/L sodium citrate buffer pH 6.0 in a microwave oven at maximum power for 1 min and at 20% power for 9 minutes, followed by a 20 minutes cool down and rinses in wash buffer. The slides were, then incubated for 1 hour with the anti-klotho protein antibody (Calbiochem, BD Biosciences, San Jose, Calif., 1:100 dilution) after blocking with normal serum for 30 minutes, reacted with the secondary antibody for 30 minutes and signal amplification and chromogen development were conducted for 30 minutes each. The stained slides were counterstained with hematoxylin and mounted. Antibody staining specificity was determined by staining kidney sections, and each run included appropriate positive and negative control slides. Staining was scored by percent of positive tumor cells and staining intensity.

Pancreatic cancer sections were prepared, after IRB approval, from 18 pancreatic cancer samples and 5 normal pancreas samples, diagnosed at the Chaim Sheba Medical Center (Ramat Gan, Israel) and Cedars-Sinai Medical Center (Los Angeles, Calif., USA). Staining was performed as described (12) and scored by percent of positive tumor cells and staining intensity. Negative and low expressions were categorized low, while intermediate and high expressions were categorized as high.

Cells and Transfections:

Breast cancer cell lines were obtained from the American Type Culture Collection (Manassas, Va.). All transfections used LipofectAMINE 2000 (Invitrogen). Stable clones were generated by selection in complete culture medium containing 750 µg/ml G418.

Panc1, MiaPaCa2 and Colo357 pancreatic adenocarinoma cell lines, the pancreatic neurodocrine tumor (NET) cancer cell line BON-1 and the noncancerous HEK-293 were obtained from the American Type Culture Collection (Manassas, Va. USA). All transfections used LipfectAMINE 2000 from Invitrogen.

Real Time Reverse Transcription-PCR (RT-PCR):

For breast cell studies, total RNA was extracted using the RNA isolation kit (Sigma) and processed to cDNA with RevertAid (Fermentas, Vilnius, Lithuania). Primers were designed using Primer Express (Applied Biosystems, Foster City, Calif.) and synthesized by IDT (Coralville, Iowa). Klotho protein specific primers were: Forward 5'-GCTCT-CAAAGCCCACATACTG, reverse 5'-GCAGCATAACGA-TAGAGGCC. Amplification reactions were performed with Platinum qPCR SuperMix (Invitrogen) in triplicates in an ABI Prism™ 7000 (Applied Biosystems) as previously described (Wolf et al., 2007).

For pancreatic cells, total RNA extraction, cDNA production and quantitative RT-PCR were performed as described (Wolf et al., 2008). Total RNA of human normal pancreas was obtained from BioChain (Hayward, Calif., USA). cDNA from pancreatic adenocarcinoma tumor and normal tissue adjacent to the tumor were obtained from the Institutional Tissue Bank of the Chaim Sheba Medical Center after IRB approval.

Western Blot Analysis:

For breast cells, cells were harvested and lysed for total protein extraction in RIPA buffer (50 mM Tris-Cl pH 7.4, 150 mM NaCl, 1% NP-40, 0.25% Na-deoxycholate, 1 mM EDTA, 1 mM NaF) together with a protease inhibitor cocktail (Sigma). 50 µg protein extracts were loaded on 10% polyacrylamide gels, separated electrophoretically and blotted from the gel onto nitrocellulose membrane (Schleicher & Schuell Bioscience GmbH, Dassel, D E). The membranes were then immunoblotted with the indicated antibodies.

For pancreatic cells, protein extraction and Western blotting was performed as described (Wolf et al., 2008).

Immunoprecipitation:

Cells were harvested as for Western blot, and 400 µg protein lysate were incubated with IgG-Sepharose (Sigma) or protein A/G (Pierce, Rockford, Ill.) beads at 4° C. for 1 h to eliminate non-specifically bound proteins. These beads were subsequently used as a negative control. The supernatants were then incubated for 4 hours with either 2 µg anti-HA antibody (Sigma) or 2 µl of anti-IGF-1β-R (Santa Cruz Biotechnology) and IgG-Sepharose or protein A/G (Pierce, Rockford, Ill.), respectively, was added. Following an overnight incubation, the beads were washed 6 times in RIPA buffer and the immunoprecipitated materials were separated by SDS-PAGE and detected by Western blotting.

Colony Assays:

Breast Cells:

Two days following transfection with the indicated plasmids, G418 (750 µg/ml) was added to the culture media; and at day 14, the cells were stained using gentian violet. Untransfected cells were treated similarly, and all died within the 2 weeks of culture in the selection media. Quantification of the results was performed using AlphaImager 2000 (Alpha Innotech, CA).

Pancreatic Cells:

Two days following transfection with the indicated plasmids, G418 (900 µg/ml for Panc1, 1000 µg/ml for MiaPaCa2 and 750 µg/ml for Colo357, HEK-293 and BON1) was added to the culture media. At day 14, cells were stained using crystal violet (Sigma-Aldrich) and quantitated as described (Wolf et al., 2008).

3-(4,5-dimethylthiazol-2-yl)-2,5-diphenyltetrazolium bromide (MTT) Viability Assay Breast Cells:

$7.5 \times 10^3$ cells/well were plated in 96-well plates, cultured in the appropriate culture media, and transfected with either control plasmid or klotho protein plasmid; and at indicated times, cells were cultured for two hours with 500 µg/ml MTT reagent (Sigma-Aldrich, St. Louis, Mo.). The medium was aspirated, and the cells were dissolved by dimethyl sulfoxide (DMSO). Absorbance of the formazan product was measured by an enzyme-linked immunosorbent assay reader.

Pancreatic Cells:

3000 cells/well were plated in 96-well plates, cultured in the appropriate culture media, and treated for 48 hrs as indicated. MTT assay was carried out as described previously (Wolf et al., 2008).

Soft Agar Assay:

To determine the effect of klotho protein on anchorage-independent growth, 15,000 Panc1 cells per well were cultured in Noble agar (Sigma-Aldrich) at a final concentration of 0.3%, on top of 0.5% base agar. Cells were seeded in triplicate wells of 6-well plates, and re-fed twice a week with growth medium containing hKL (0.8 pM) or control vehicle. Colonies were counted after 21 days, following staining with 0.005% crystal violet.

Generation of Soluble Klotho Protein:

Soluble klotho protein was generated essentially as described (Kurosu et al., 2005). In brief, insect cells, which stably express V5-tagged soluble klotho protein, were generated using the *Drosophila* Expression System (Invitrogen). A cDNA fragment encoding the entire extracellular domain of mouse Klotho protein (amino acid residues 31 to 982 of SEQ ID NO: 3) was inserted into a pMT/BiP/V5-His expression vector, allowing inducible expression from metallothionein promoter and secretion of the recombinant protein with V5 and 6×His tags at the C-terminus into conditioned medium. The expression vector was transfected into *Drosophila* Schneider cells by the calcium phosphate method together with pCoHYGRO selection vector. Stable transformants were selected with hygromycin B and cloned by limiting dilution to obtain clones with high expression levels. Expression of soluble Klotho protein was induced in serum-free medium containing 1 mM $CuSO_4$ for 14 days. Klotho protein secreted in the conditioned medium was purified by affinity column chromatography using agarose affinity gel with anti-V5 antibodies (Sigma). Purified Klotho protein and known concentrations of albumin were subjected to SDS-PAGE followed by Sypro Ruby staining (Molecular Probe) to ascertain the concentration and purity of the protein.

Statistical Analysis:

Results are presented as mean±standard deviation (SD). Categorized variables were compared between the study groups using Fisher's exact test and continuous variables were compared using t-test. All significance tests were two-tailed and a P-value of <0.05 was considered as statistically significant. The nature of interaction between Klotho protein and 5-FU or Gemcitabine was analyzed using the additive model (Jonsson et al., 1998). A ratio between the observed and the predicted viability was calculated for all combinations and a ratio <0.8 for the interaction was considered to be synergistic.

I. Breast Cancer Studies

Klotho Protein Expression in Breast Tissue

Immunohistochemical analysis of klotho protein was conducted on breast tissue arrays consisting of 11 normal breast samples, 58 early stage invasive ductal carcinomas (IDC) and 47 pure ductal carcinomas in situ (DCIS) samples. Normal tissue adjacent to the IDC and DCIS was also analyzed. Human kidney sections, which are known to express high klotho protein levels only at the distal tubules (Kato et al., 2000), served as controls.

Clinical and pathological tumor characteristics of the 22 invasive breast cancer samples that showed klotho protein expression were compared to 36 invasive breast cancers that had no klotho protein expression. Results are shown in FIG. 1 and Table 1.

TABLE 1

Klotho protein expression in normal breast, DCIS* and invasive ductal carcinoma of the breast.

| | | Normal breast N = 11 (%) N | Normal adjacent to DCIS N = 45 (%) N | DCIS[1] N = 47 (%) N | Normal adjacent to IDC[2] N = 55 (%) N | IDC N = 58 (%) N |
|---|---|---|---|---|---|---|
| Klotho protein expression | absent | (0) 0 | (0) 0 | (28) 13 | (0) 0 | (38) 22 |
| | low | (0) 0 | (10) 4 | (55) 26 | (9) 5 | (40) 23 |
| | high | (100) 11 | (90) 41 | (17) 8 | (91) 50 | (22) 13 |

DCIS, ductal carcinoma in situ; IDC, invasive ductal carcinoma.
P < 0.0001 for comparisons of normal or adjacent normal samples to either DCIS or IDC samples The relationship between klotho protein expression and tumor proliferative index was evaluated using K167 staining. The relationship between klotho protein expression and tumor size was also studied. Results are shown in Table 2.

TABLE 2

Distribution of study variables by klotho protein levels

| | | No klotho protein expression N = 22 (%) N | klotho protein expression N = 36 (%) N | Overall P value |
|---|---|---|---|---|
| Median Age (range) | | (27-86) 52 | (32-95) 51 | 0.48 |
| Tumor size (T) | 1 | (45) 10 | (72) 26 | for 1 0.08 |
| | 2 | (41) 9 | (25) 9 | vs 2-3 |
| | 3 | (9) 2 | (3) 1 | |
| | Unknown | (5) 1 | (0) 0 | |
| Lymph nodes involvement (N) | Negative | (45) 10 | (58) 21 | 0.16 |
| | Positive | (50) 11 | (28) 10 | |
| | Unknown | (5) 1 | (14) 5 | |
| Histology | IDC | (91) 20 | (100) 36 | 0.14 |
| | Other | (9) 2 | (0) 0 | |
| Grade | 1-2 | (73) 16 | (58) 21 | 0.26 |
| | 3 | (22) 5 | (39) 14 | |
| | Unknown | (5) 1 | (3) 1 | |
| ER | Negative | (9) 2 | (22) 8 | 0.3 |
| | Positive | (73) 16 | (67) 24 | |
| | Unknown | (18) 4 | (11) 4 | |
| PR | Negative | (18) 4 | (22) 8 | 1 |
| | Positive | (64) 14 | (67) 24 | |
| | Unknown | (18) 4 | (11) 4 | |
| KI67 | 1 | (35) 6 | (55) 20 | 0.04 |
| | 2 | (26) 4 | (0) 0 | (vs 2, 3 1) |
| | 3 | (13) 5 | (18) 6 | |
| | Unknown | (26) 7 | (22) 10 | |

IDC, invasive ductal carcinoma; ER, estrogen receptor; PR, progesterone receptor.

Figure 2:
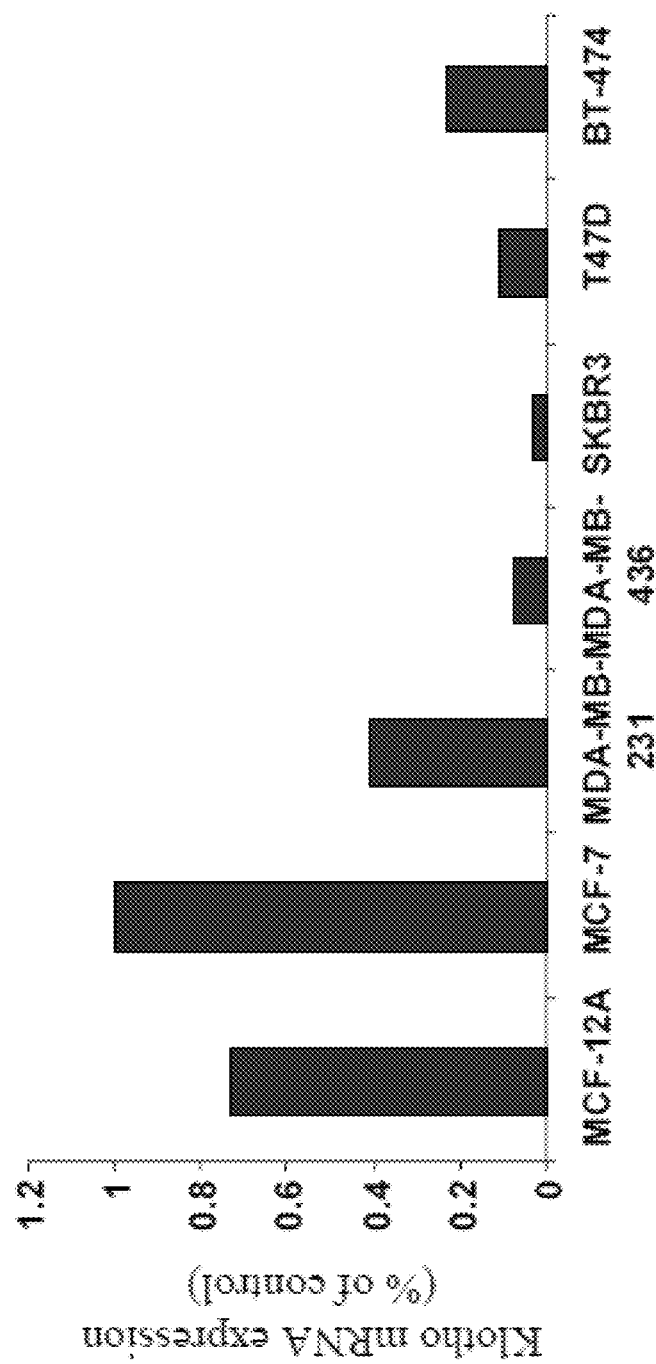
FIG. 2 is a bar chart showing klotho protein mRNA levels as determined by quantitative real-time RT-PCR in different breast cancer cell lines, relative to the expression in MCF-7.

Klotho Protein Expression in Breast Cancer Cell Lines Using Real Time Polymerase Chain Reaction The expression of klotho protein was analyzed in breast cancer cell lines (MCF-12A, MCF-7, MDA-MB-231, SK-BR3, T-47D. and BT-474), using real-time polymerase chain reaction (RT-PCR), which is used to amplify and simultaneously quantify a targeted DNA molecule. It enables both detection and quantification (as absolute number of copies or relative amount when normalized to DNA input or additional normalizing genes) of a specific sequence in a DNA sample. The selected cell lines have different phenotypes and different expressions patterns of the estrogen receptor (ER), Her2 and p53, and thus represent various subclasses of breast cancer (Lacroix & Leclercq, 2004). Results are shown in FIG. 2.

Effect of Over-Expression of Klotho Protein on Growth of Breast Cancer Cells

The effect of klotho protein on growth of breast cancer cells was first assessed using colony formation assays. MCF-7, MDA-MB-231 and the non-cancerous human embryonic kidney (HEK) 293 cells were transfected with either a HA-tagged klotho protein expression vector (pcDNA3-HI-A-KL) or an empty vector (pcDNA3). Transfected cells were cultured in media containing G418 for two weeks and stained to determine the number of surviving colonies.

In order to assess the long-term effects of klotho protein expression, MCF-7 and MDA-MB-231 clones, which stably expressed either pcDNA3 or pcDNA3-HA-KL, were generated. Proliferation was evaluated by 3-(4,5-dimethylthiazol-2-yl)-2,5-diphenyltetrazolium bromide (MTT) assay after seeding for 24-72 h.

Figure 4A:
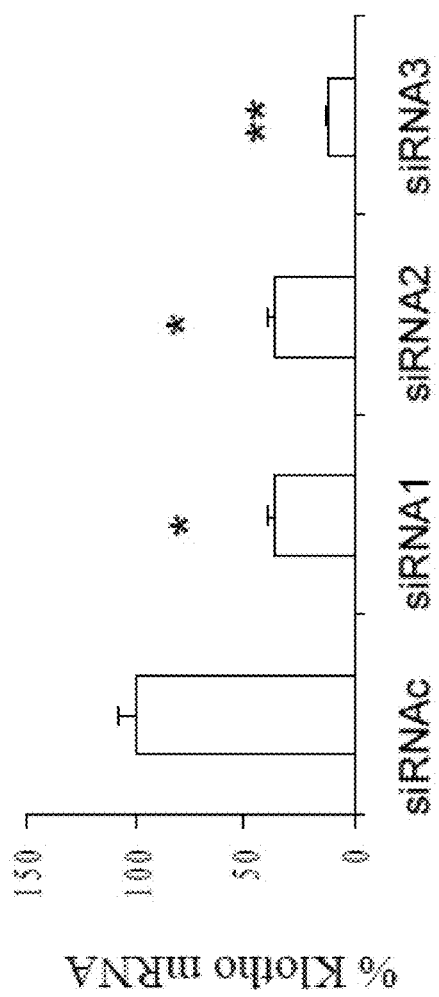
FIG. 4A is a bar chart showing klotho protein mRNA expression in MCF-7 cells transfected with control siRNA (siRNAc) or three klotho protein-directed siRNA (siRNA1-3)
Figure 4B:
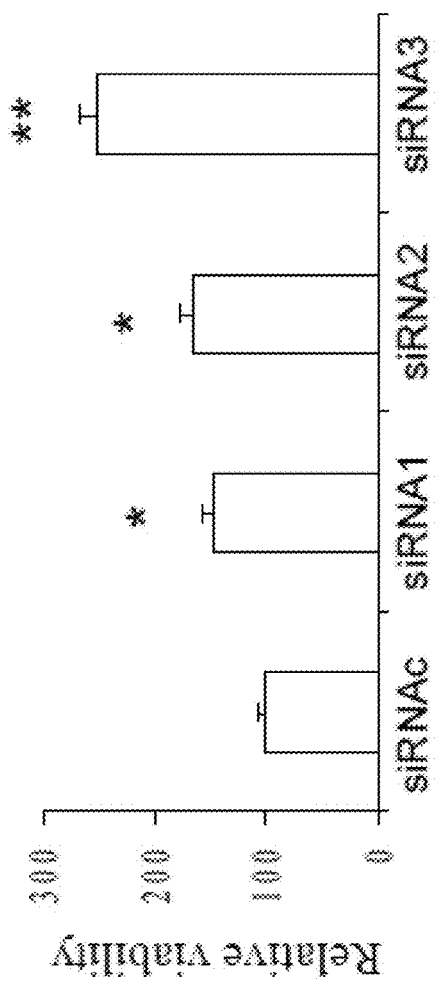
FIG. 4B is a bar chart showing relative viability of MCF-7 cells transfected with control siRNA (siRNAc) or three klotho protein-directed siRNA (siRNA1-3)

As some klotho protein expression was noted in MCF-7 cells (FIG. 2), the effects of down-regulation of klotho protein on these cells was studied. Three klotho protein-directed siRNAs were designed and tested for their ability to silence klotho protein expression in MCF-7 cells, compared to a control siRNA (siRNAc). Results are shown in FIGS. 4a and 4b.

Effect of Over-Expression of Klotho Protein on p53 Levels

Figure 5:
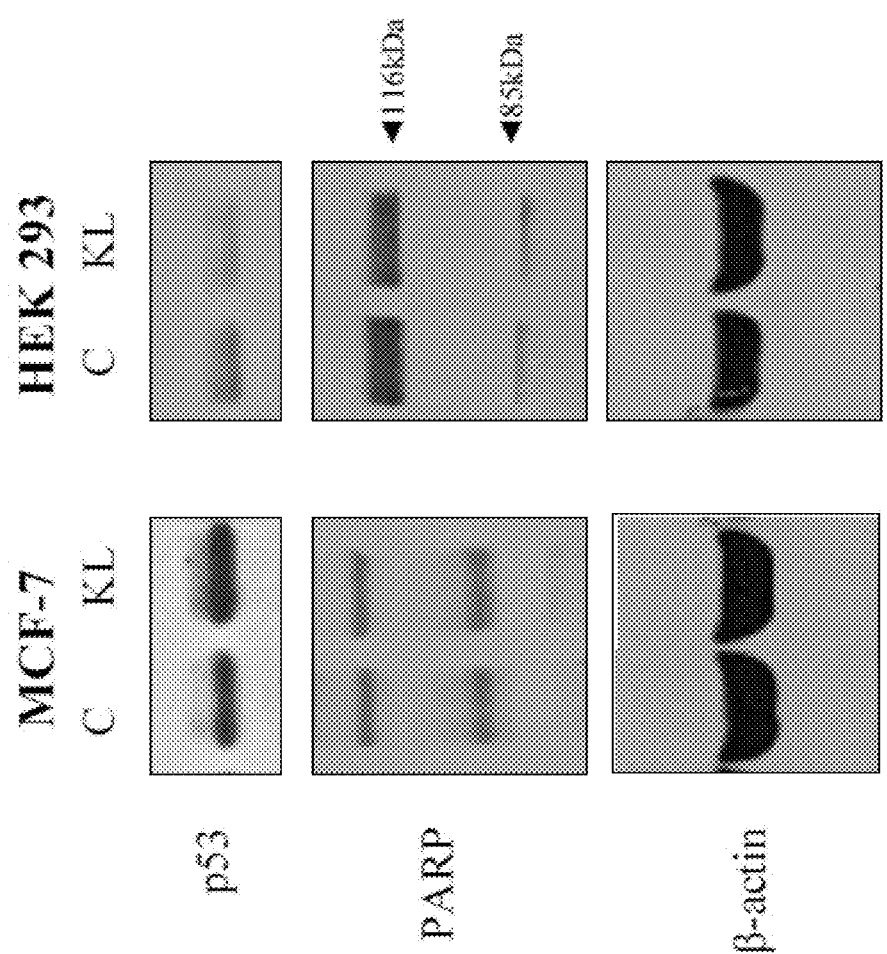
FIG. 5 shows an immunoblot of MCF-7 and HEK293 cells transfected with either klotho protein expressing vector (KL) or an empty vector (C)

In fibroblasts, klotho protein reduces senescence through down-regulation of p53 (de Oliveira, 2006). The effects of klotho protein on p53 levels in MCF-7 breast cancer cells and HEK 293 were therefore analyzed. Results are shown in FIG. 5.

Effect of Klotho Protein on IGF-1-Induced MCF-7 Proliferation

Klotho protein is known to inhibit activation of the IGF-1 pathway in L6 myoblasts cells and rat hepatoma H4IIE cells (Kurosu et al., 2005). This pathway plays an important role in breast cancer tumorigenesis, and IGF-1 induces MCF-7 cell proliferation (Geier et al., 1995; Yee, 2006). In order to test the ability of klotho protein to modulate IGF-1-induced proliferation and survival, MCF-7 cells were transiently transfected with either pcDNA3 or pcDNA3-HA-KL, and grown in 0.5% serum with either IGF-1 or a control vehicle for 24-96 hr. Results are shown in FIG. 6.

Effect of Klotho Protein on Inhibition of Activation of the IGF-1/Insulin Pathway and Relationship with IGF-IR in Breast Cancer Cells The effect of klotho protein was studied on IGF-1 pathway activation in MCF-7 breast cancer cells, which express high IGF-1R levels and showed an enhanced proliferation following IGF-1 treatment (Geier et al., 1995; Haimsohn et al., 2002). MDA-MB-231 cells, which express lower levels of these receptors, were also examined. HEK 293 cells, whose growth is not dependent on the IGF-1 pathway (El-Shewy et al., 2007) and is not inhibited by klotho protein, served as control.

Figures 7A, 7B:
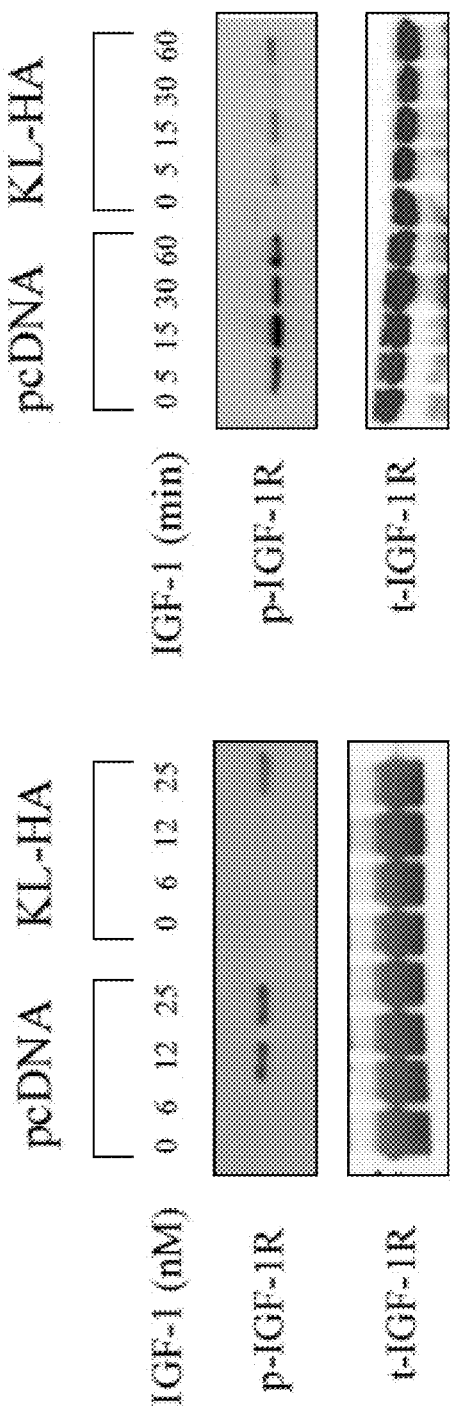
FIG. 7A shows an immunoblot of MCF-7 cells transfected with either klotho protein-HA expression plasmid (KL-HA) or a control vector (pcDNA3) and treated with IGF-1 (15 min) for the indicated doses.
FIG. 7B shows an immunoblot of MCF-7 cells transfected with either klotho protein-HA expression plasmid (KL-HA) or a control vector (pcDNA3) and treated with IGF-1 (12.5 nM) for the indicated times.

In order to elucidate klotho protein activity as an inhibitor of TGF-1-induced activation, MCF-7 cells were transfected with either pcDNA3-HA-KL or an empty vector, starved for 48 hours, treated with IGF-1 for the indicated times and doses, and analyzed using Western blotting for the level of expression and phosphorylation of IGF-1R. Results are shown in FIGS. 7a and 7b.

Figure 8:
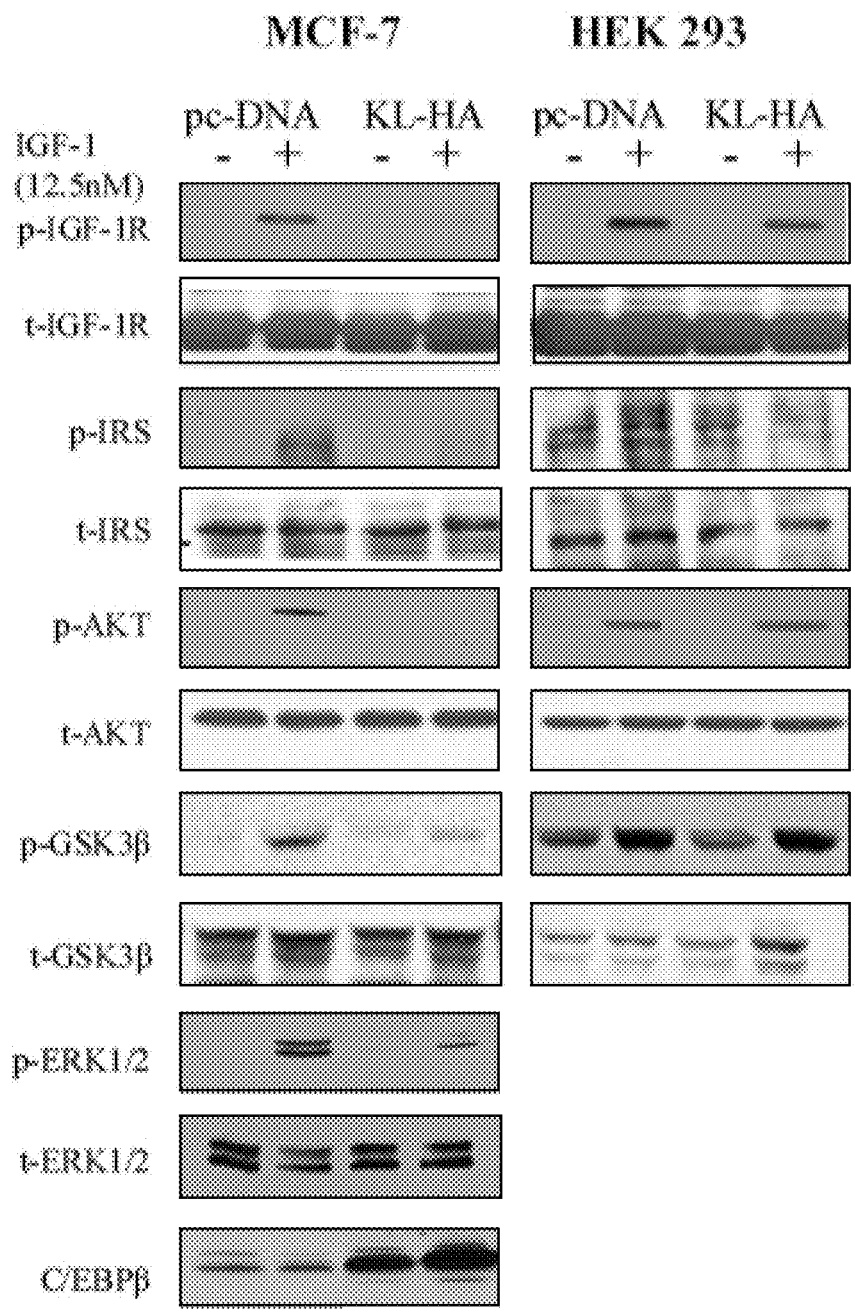
FIG. 8 shows an immunoblot of MCF-7 and HEK293 cells transfected with either klotho protein-HA expression plasmid (KL-IA) or a control vector (pcDNA3) and stimulated with IGF-1 (12.5 nM. 15 min). Cell lysates were immunoblotted using anti-phosphorylated (p) and total (t) IGF-1R, p- and t-IRS-1, p- and t-AKT, p- and t-GSK3β, p- and t-ERK1/2 and C/EBPβ antibodies.

In further experiments, MCF-7, MDA-MB-231 or HEK-293 cells were transfected with either pcDNA3-HA-KL or empty vector and treated with IGF-1 (12.5 nM, 15 min). Results are shown in FIG. 8.

Figure 9A:
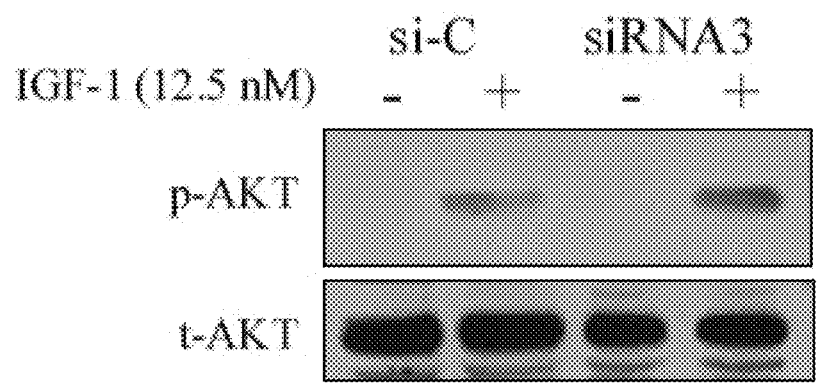
FIG. 9A shows an immunoblot of klotho protein silenced in MCF-7 cells using siRNA3 or control siRNA (si-C). Cell lysates were immunoblotted using anti p- and t-AKT antibody.

The effect of silencing of klotho protein in MCF-7 cells, using siRNA3, was also studied. Results are shown in FIG. 9a.

Figure 9B:
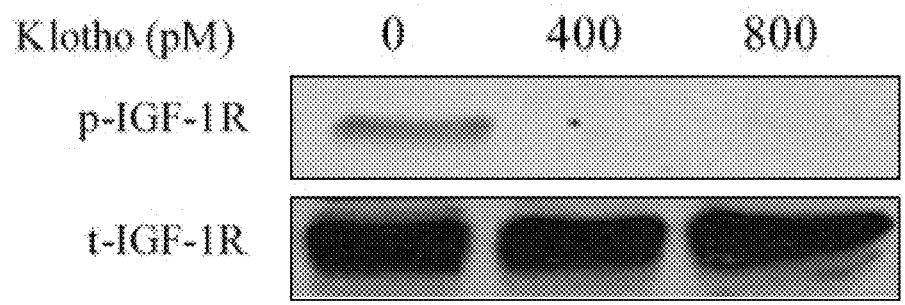
FIG. 9B shows an immunoblot of MCF-7 cells treated with soluble klotho protein and stimulated with IGF-1 (12.5 nM, 15 min). Cell lysates were immunoblotted using anti-phosphorylated (p) and total (t) IGF-1R.

As klotho protein may also be shed and act as a circulating hormone (Kuro-o et al., 1997; Matsumura et al., 1998), the ability of soluble klotho protein to inhibit activation of the IGF-1 pathway in MCF-7 cells was tested. V5-tagged soluble klotho protein was generated as described under "Materials and Methods", its expression and purity were examined using Coomassie staining and its concentration was determined (data not shown). MCF-7 cells were treated with klotho protein for 15 min and, stimulated with IGF-1 (12.5 nM, 15 min), and expression and phosphorylation of the IGF-1R was determined. Results are shown in FIG. 9b.

C/EBPβ is a down-stream target of the GSK3β pathway, which is suppressed following stimulation by IGF-1 (Li et al., 2007). It has tumor suppressor activities in breast cancer and is upregulated during klotho protein-induced adipocyte differentiation (Chihara et al., 2006). The effects of over-expression of klotho protein on C/EBPβ levels were therefore analyzed.

Figure 10:
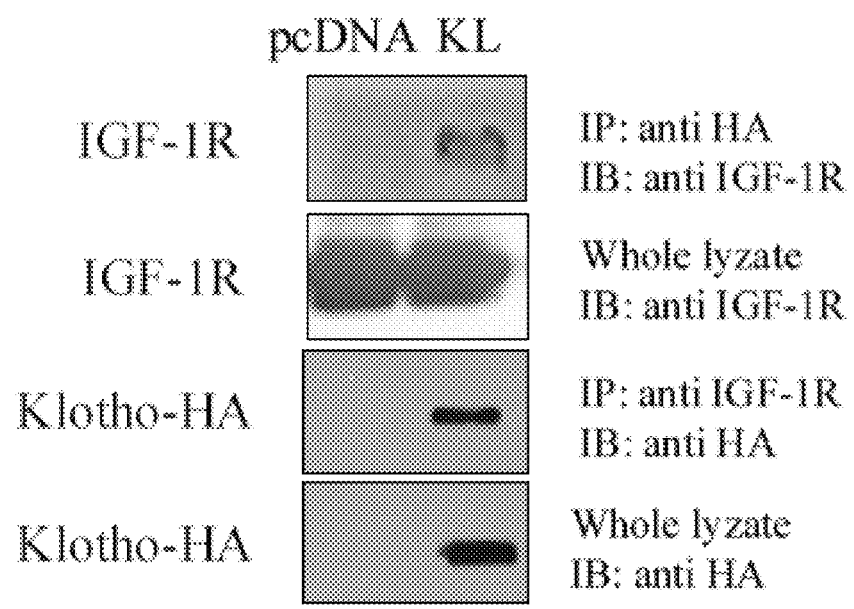
FIG. 10 shows an immunoblot of MCF-7 cells stably expressing HA-klotho protein or a control vector, which were lysed and immunoprecipitated for klotho protein using anti-HA antibody and immunoblotted with anti-1IGF-1R antibodies.

As klotho protein can bind FGFR and other membrane proteins, binding of klotho protein to the IGF-1R was examined. Co-immunoprecipitation assays were conducted using MCF-7 cells either stably (FIG. 10) or transiently (data not shown) expressing HA-klotho protein. HA-klotho protein was detected by Western blotting following immunoprecipitation of the IGF-1R, and the IGF-1R was detected following immunoprecipitation using HA-directed antibody.

Figure 11A:
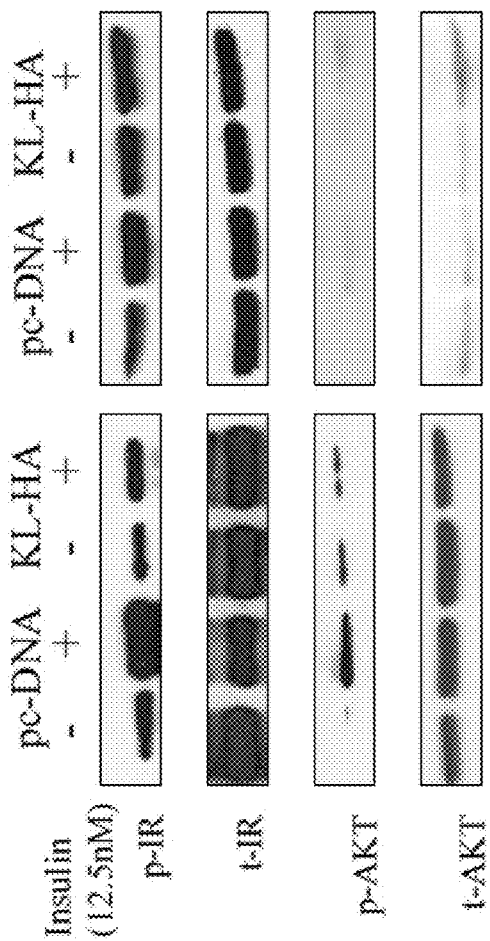
FIG. 11A shows an immunoblot of MCF-7 and HEK293 cells transfected and stimulated with insulin. Cell lysates were immunoblotted using anti-p- and t-insulin receptor (IR) and p- and t-AKT antibodies.
Figure 11B:
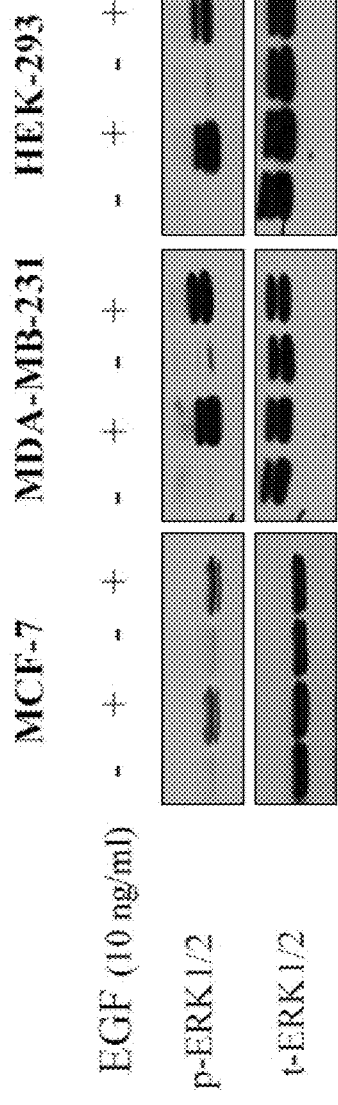
FIG. 11B shows an immunoblot of. MCF-7, MDA-MB-231 and HEK293 cells transfected and stimulated with EGF. Cell lysates were immunoblotted using anti-phosphorylated (p) and total (t) ERK1/2 antibodies.

Effect of Over-Expression of Klotho Protein on Insulin Stimulation and Activation of the EGF Pathway in Breast Cancer Cells The effects of over-expression of klotho protein on the insulin-stimulated pathway were also examined. Results are shown in FIGS. 11a and 11b. The EGF pathway, which plays an important role in the pathogenesis of breast cancer, is not modulated by klotho protein in either L6 or H411E cells (Kurosu et al., 2005). In order to evaluate the effects of klotho protein on this pathway in MCF-7, MDA-MB-231 and HEK293 breast cancer cells, these cells were transfected with either pcDNA3-HA-KL or an empty vector, starved for 48 hours, treated with EGF, and analyzed for the expression and activity of the ERK1/2, which are downstream targets of the EGF pathway.

II. Pancreatic Cancer Studies

Klotho Protein Expression in Pancreatic Cancer Cells

Tissue samples obtained from 3 normal pancreas and 12 pancreatic carcinoma were analyzed using immunohistochemical staining, at ×200 and ×400 magnification. Representative results are shown in FIG. 12a-12d.

Pancreatic carcinoma cell lines Colo357, MiaPaCa2, and Panc1 were also analyzed for klotho protein expression.

Effect of Over-Expression of Klotho Protein on Growth of Pancreatic Cancer Cells The effect of over-expression of klotho protein on growth of pancreatic cancer cells was studied using both a colony formation assay and a 3-(4,5-Dimethylthiazol-2-yl)-2,5-diphenyltetrazolium bromide (MTT) proliferation assay.

Figure 13:
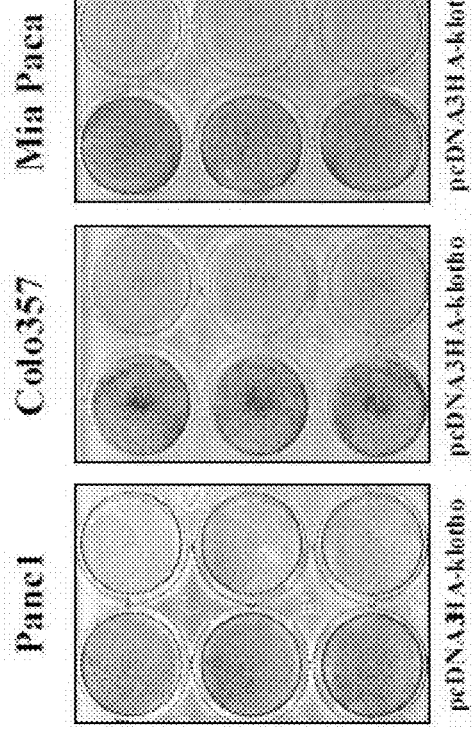
FIG. 13 shows a photograph of a colony formation assay, in which pancreatic carcinoma cell lines Colo357, MiaPaCa2, and Panc1 were transfected with either a HA-tagged klotho protein expression vector (pcDNA3-HA-KL) or an empty vector (pcDNA3) and colonies were stained with crystal violet.

For the colony formation assay, pancreatic carcinoma cell lines Colo357, MiaPaCa2, and Panc1 were transfected with either a HA-tagged klotho protein expression vector (pcDNA3-HA-KL) or an empty vector (pcDNA3). Transfected cells were cultured in media containing G418 for two weeks. Colonies were stained with crystal violet and photographed. Results are shown in FIG. 13.

Figure 14:
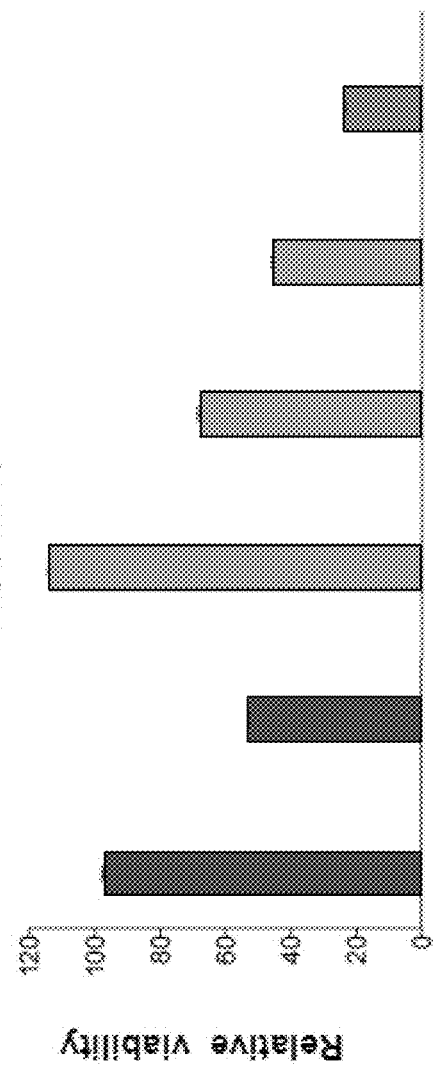
FIG. 14 is a bar chart showing the results of an MTT proliferation assay.

For the MTT proliferation assay, Panc1 cells ($3 \times 10^3$/well) were plated in 96-well plates, cultured in the appropriate culture media containing 10% FCS, and treated with either soluble klotho protein (sol KL), the chemotherapeutic agent 5-Fluorouracil (5-FU), or a combination of sol KL and 5-FU. Medium alone served as control. 48 hr after incubation, cells were cultured for 2 hr with 500 µg/ml MTT reagent, the medium was aspirated, and the cells were dissolved in dimethyl sulfoxide (DMSO). Absorbance of the formazan product was measured by an enzyme-linked immunosorbent assay reader to provide a measure of viability. Results are shown in FIG. 14.

In Vivo Studies of the Effect of Klotho Protein on Pancreatic Cancer

Figure 15:
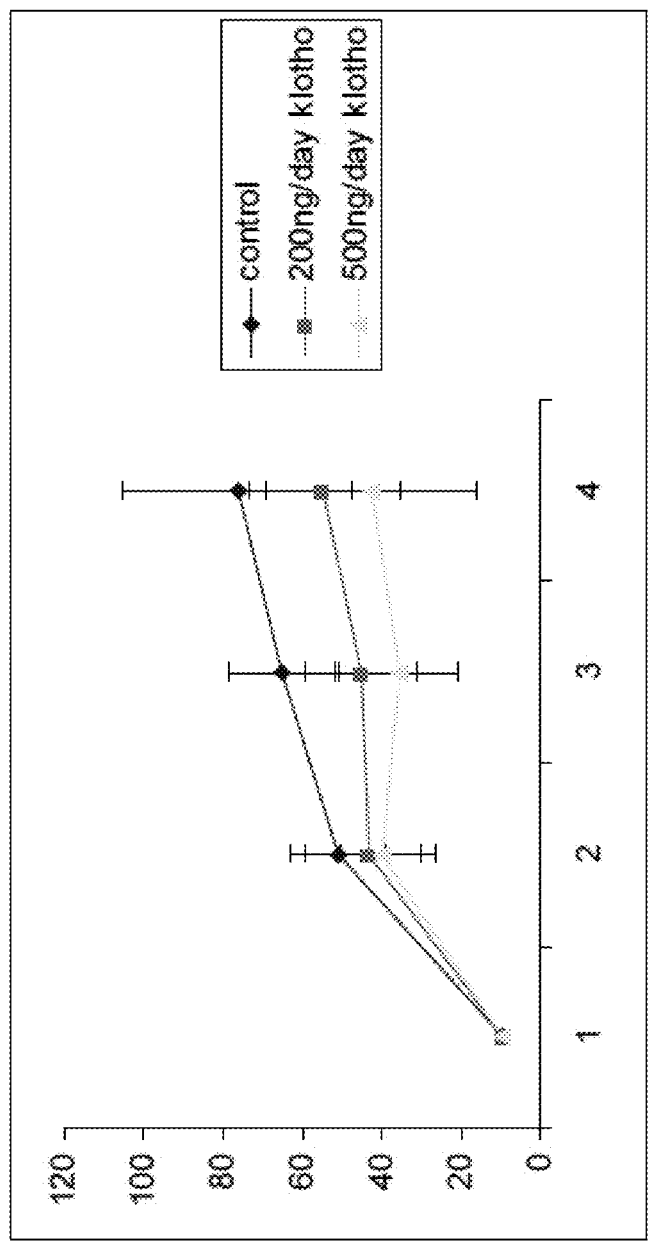
FIG. 15 is a graph showing the effect of klotho protein on tumor size.

Panc1 cells were harvested, washed twice with sterile PBS, counted and resuspended in Matrigel (BD Biosciences). Six-week-old female athymic nude mice were injected subcutaneously in both flanks with cells at a density of $0.5 \times 10^6$ cells/100 µl. The mice were treated with daily intra-peritoneal injections of either soluble klotho protein (prepared as described above): 200 ng/day, 500 ng/day, or vehicle control (saline). Five mice were used in each group. Tumor size was measured weekly with a linear caliper for up to 4 weeks, and tumor volume was estimated using the equation $V=(a \times b^2) \times 0.5236$, where "a" is the larger dimension and "b" the perpendicular diameter. Results are shown in FIG. 15.

Figures 16A, 16B:
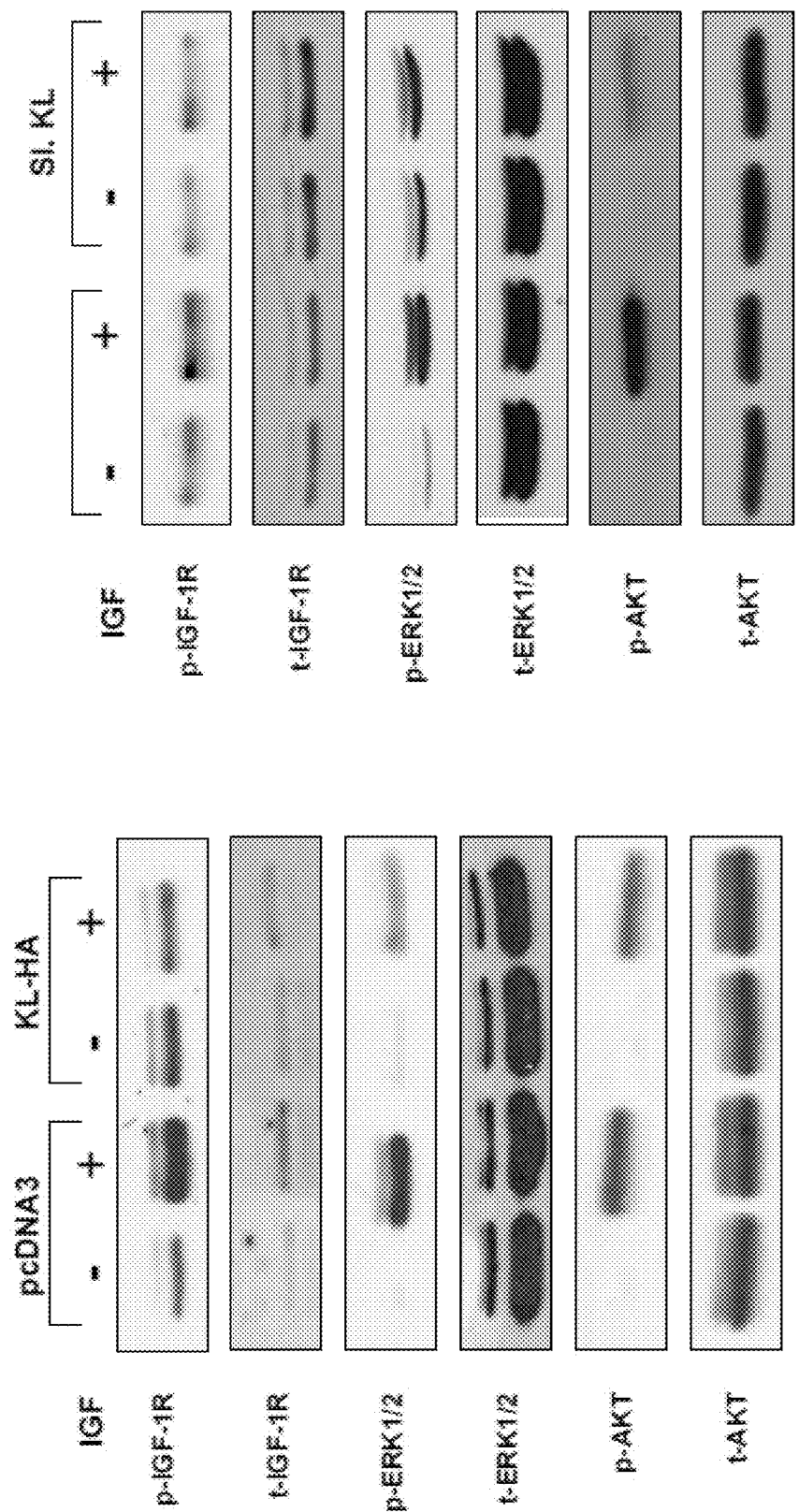
FIG. 16A is an immunoblot of Panc1 cells transfected with either klotho protein-HA expression plasmid (KL-HA) or a control vector (pcDNA3) using antibodies directed against phosphorylated (p) and total (t) IGF-1R, p- and t-AKT, p- and t-ERK1/2.
FIG. 16B is an immunoblot of Panc1 cells treated with klotho protein and stimulated with IGF-1.

Down-Regulation of the IGF-1 Pathway by Klotho Protein in Pancreatic Cancer Cell Lines Panc1 cells were transfected with either klotho protein-HA expression plasmid (KL-HA) or a control vector (pcDNA3). After 24 hrs, cells were serum starved for 48 hr and treated with IGF-1 (12.5 nM, 15 min). Following treatment, cells were harvested and proteins were resolved and immunoblotted using antibodies directed against phosphorylated (p) and total (t) IGF-1R, p- and t-AKT, p- and t-ERK1/2. Results are shown in FIG. 16a.

Since klotho protein is shed and may act as a circulating hormone, the ability of soluble klotho protein to inhibit activation of the IGF-1 pathway in Panc1 cells was tested. V5-tagged soluble klotho protein was generated as described [Kurosu H. et al., 2005]. Panc1 cells were treated with klotho protein for 10 min and stimulated with IGF-1 (12.5 nM, 15 min), and expression and phosphorylation of the IGF-1R, AKT and ERK1/2 was determined. Results are shown in FIG. 16b.

In Vivo Studies of the Effect of Klotho Protein on Various IGF-Dependent Cancers Cells of various human IGF-1 dependent cancers are obtained in the usual way, counted and suspended in Matrigel (BD Biosciences). Six-week-old female athymic nude mice are injected subcutaneously in both flanks with cells at a usual density (e.g., $0.5 \times 10^6$ cells/100 µl). The mice are treated with daily intra-peritoneal injections of either a klotho protein (200 ng/day, 500 ng/day) or vehicle control (saline). Five mice are used in each group. Tumor size is measured weekly with a linear caliper for up to 4 weeks, and tumor volume is estimated using the equation $V=(a \times b^2) \times 0.5236$, where "a" is the larger dimension and "b" the perpendicular diameter. It is seen that the tumors in mice to which the saline control is administered have larger tumors than the mice to which klotho protein is administered.

As noted above, in these studies cancer cell representative of different IGF-1 dependent cancers are placed in mice to demonstrate the efficacy of the teachings of the present invention in treating a respective cancer in humans.

Amongst other cells, HCT116 cells are placed in mice and the mice treated as described above to demonstrate the efficacy of the teachings of the present invention in treating colon cancer in humans.

Amongst other cells, LanCap cells are placed in mice and the mice treated as described above to demonstrate the efficacy of the teachings of the present invention in treating prostate cancer in humans.

Amongst other cells, HeLa cells are placed in mice and the mice treated as described above to demonstrate the efficacy of the teachings of the present invention in treating cervical cancer in humans.

Amongst other cells, lung cancer cells (such as described in Noro R et al. *BMC cancer* 2006, 6, 277-289) are placed in mice and the mice treated as described above to demonstrate the efficacy of the teachings of the present invention in treating lung cancer in humans.

Amongst other cells, ovarian cancer cells (such as described in Masiakos P T et al. *Clinical Cancer Research* 1999, 5, 3488-3499) are placed in mice and the mice treated as described above to demonstrate the efficacy of the teachings of the present invention in treating ovarian cancer in humans.

The Klotho proteins used in the above studies are any of the Klotho proteins disclosed herein, including the isolated polypeptide sequences comprising an amino acid sequence represented by SEQ ID NOS: 1, 2, 3, 4, 5, 11, 12, 13, 14 and 15 and also an isolated polypeptide sequence comprising an amino acid sequence represented by residues 31 to 982 of SEQ ID NO: 1, residues 34 to 1012 of SEQ ID NO: 1, residues 34 to 549 of SEQ ID NO: 2 and residues 36 to 1014 of SEQ TD NO: 3 and also pegylated versions of the same.
Inhibition of Pancreatic Cell Growth by KL1

Figure 17A:
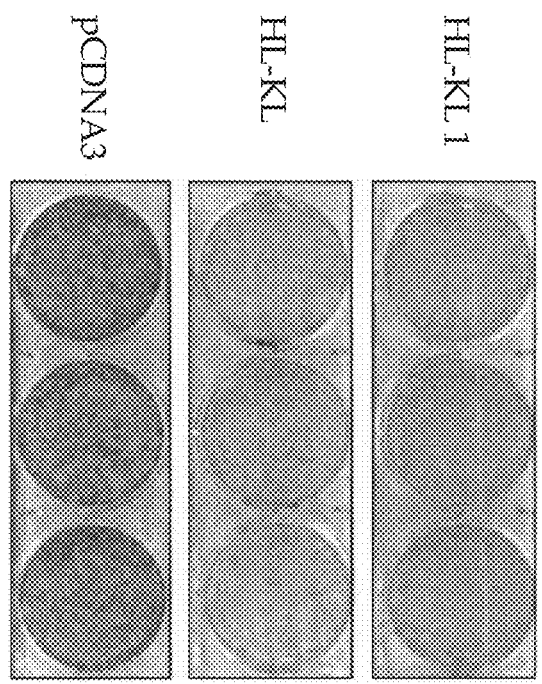
FIG. 17A shows a photograph of a colony formation assay following transfection of Panc1 cells with DNA encoding for FL-mKL (HA-KL), for mKL1 (HA-KL1) or for pCDNA.

The predominant circulating forms of Klotho protein in humans are the full-length protein (sol-hKL), KL1 cleaved product (sol-hKL1), and a splice variant composed only of KL1 (Shiraki-Iida et al., 1998: Ohayama et al., 1998; Matsumara et al., 1998). The ability of KL1 to inhibit growth of pancreatic cancer cells, compared to FL-KL, was explored (FIG. 17A). Panc1 cells were transfected with DNA encoding for full length mouse Klotho expression vector (FL-mKL), mouse KL1 (mKL1) or an empty vector (pcDNA3) and colony assay was performed.

Figure 17B:
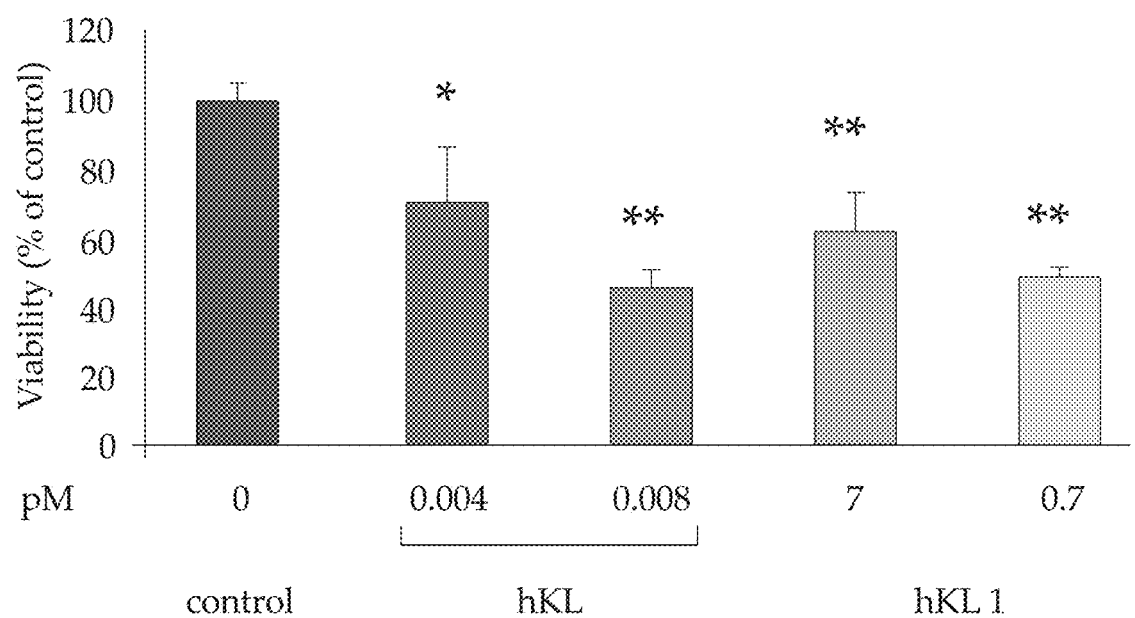
FIG. 17B is a bar graph showing viability of Panc1 cells treated with either sol-hKL or sol-hKL1.
Figure 17C:
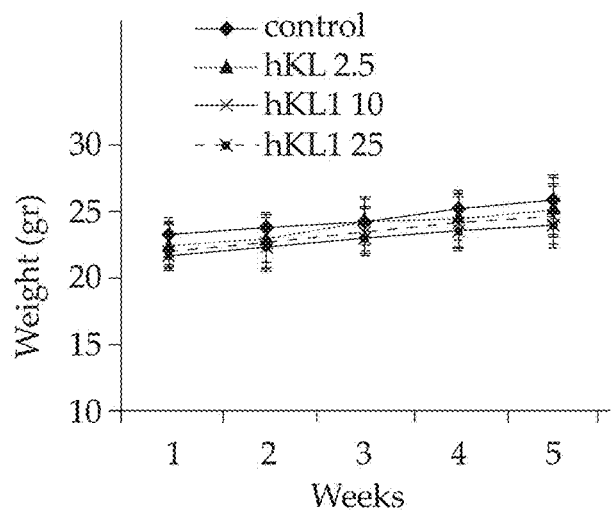
FIG. 17C is a line graph showing change in weight with time for mice treated with either sol-hKL or sol-hKL1 following injection of Panc1 cells.
Figure 17F:
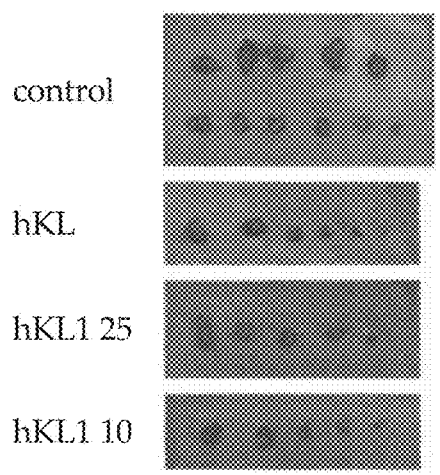
FIG. 17F is a photograph of tumors excised from mice on day of sacrifice.
Figure 17D:
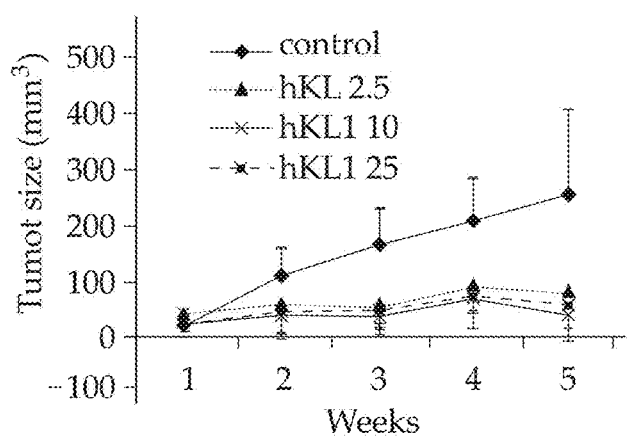
FIG. 17D is a line graph showing change in tumor size with time for mice treated with either sol-hKL or sol-hKL1 following injection of Panc1 cells.
Figure 17G:
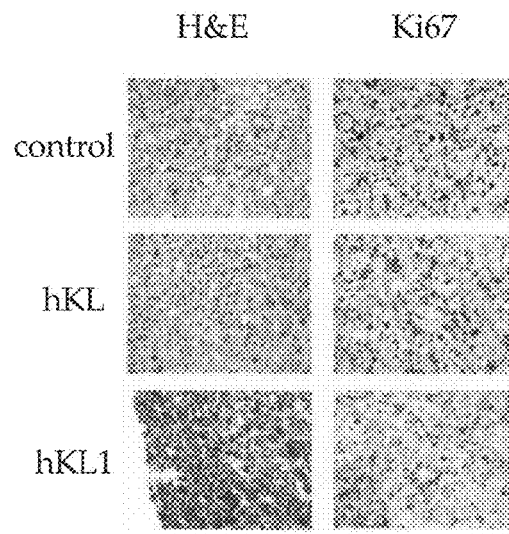
FIG. 17G shows H&E and Ki67 immunohistochemical staining of MiaPaCa2 cells treated with sol-hKL or sol-hKL1 (×400 magnification)

The activity of hKL1 was also tested. Panc1 cells were treated with either sol-hKL or sol-hKL1 for 48 hrs and viability was assessed after 48 hours by MTT assay (FIG. 17B).

Figure 17E:
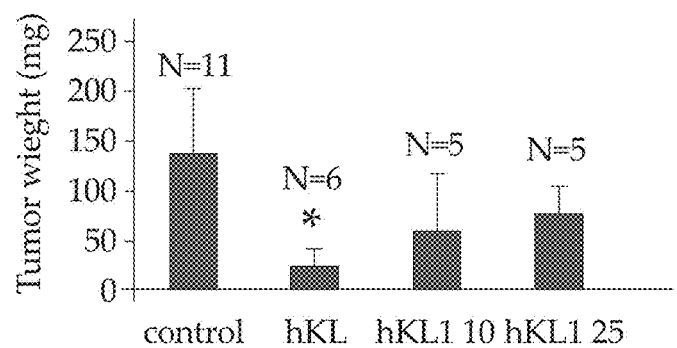
FIG. 17E is a bar graph showing tumor weight on day of sacrifice for mice treated with either sol-hKL or sol-hKL1 following injection of Panc1 cells.

The in vivo growth inhibitory activity of sol-hKL1, compared to sol-hKL, on pancreatic cancer cells was examined (FIG. 17C-G). Panc1 cells were injected into one flank of athymic mice and mice were treated with intraperitoneal injections of either control vehicle (N=12), sol-hKL (2.5 µg/kg, N=7), or sol-hKL1 (10 µg/kg, N=6; 25 µg/kg, N=7), five days a week for five weeks. Weight of mice (FIG. 17C) and tumor volume (FIG. 17D) in control and treated groups were monitored weekly and tumor weight was measured on day of sacrifice (FIG. 17E).

Figure 17H:
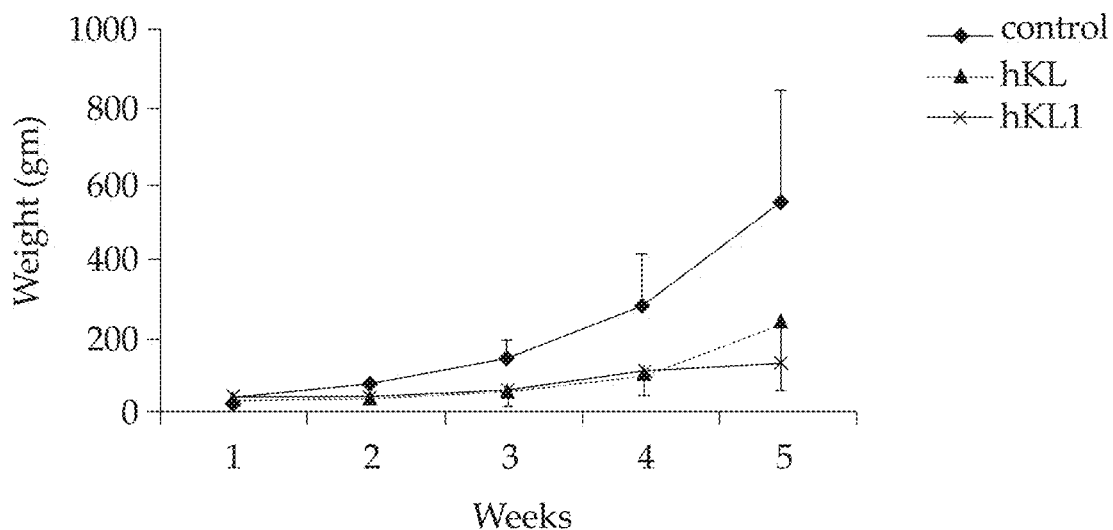
FIG. 17H is a line graph showing change in tumor size with time for mice treated with either sol-hKL or sol-hKL1 following injection of MiaPaCa2 cells.
Figure 17I:
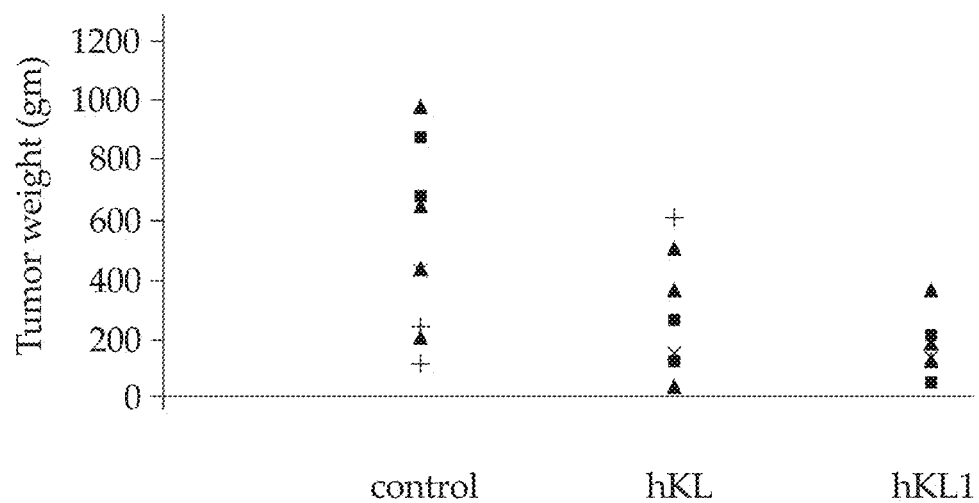
FIG. 17I shows tumor weight on day of sacrifice for mice treated with either sol-hKL or sol-hKL1 following injection of MiaPaCa2 cells.

A similar experiment, with minor differences, was also performed using MiaPaCa2 cells (FIGS. 17H, 17I). Cells were injected into both flanks of athymic mice and mice were treated with either a control vehicle (N=8), sol-hKL (2.5 µg/kg, N=8) or sol-hKL1 (10 µg/kg, N=8).

The effects of sol-hKL and sol-hKL1 on blood counts and chemistry were also studied. For these studies, blood was withdrawn from control, sol-hKL-treated (2.5 µg/kg) or sol-hKL1-treated (10 μg/kg) mice, at the same day as sacrificing and tumor harvesting, following five weeks of treatment.

Figure 17J:
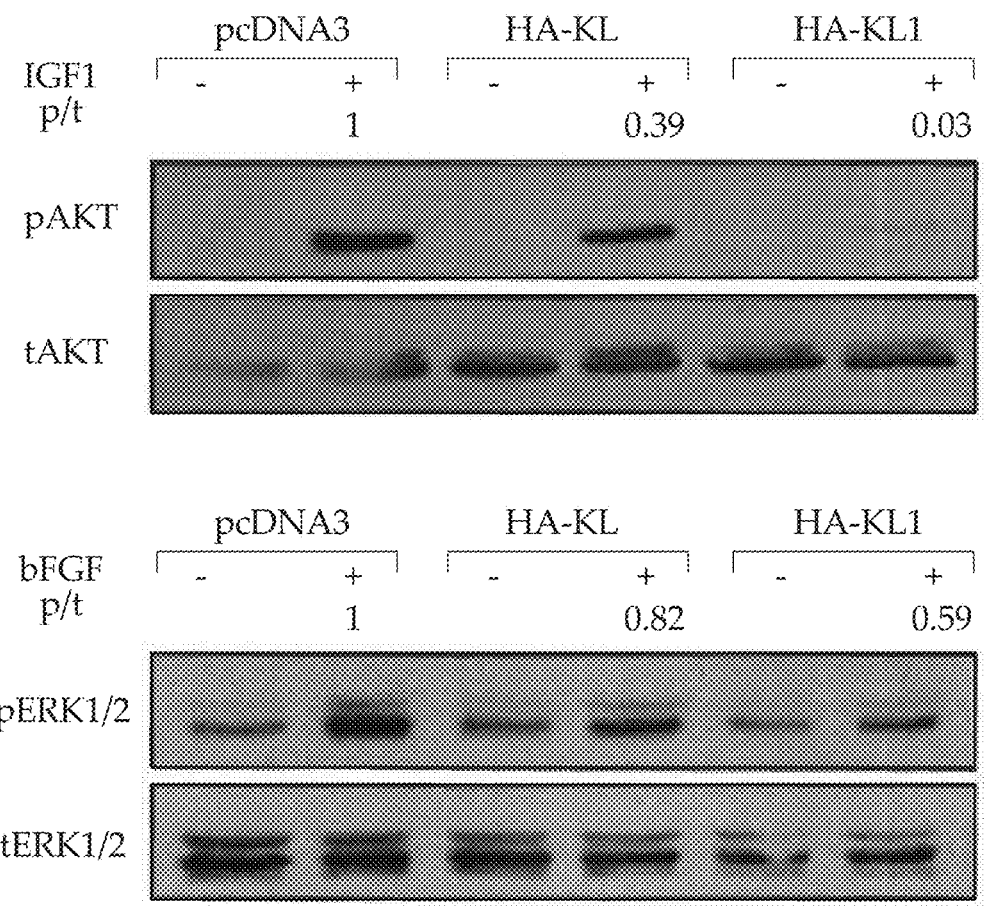
FIG. 17J is an immunoblot of Panc1 cells transfected with either klotho protein-HA expression plasmid (KL-HA), KL-1 protein-HA expression plasmid (KL1-HA) or a control vector (pcDNA3) and stimulated with phosphorylated (p) and total (t) IGF-1R or p- and t bFGF. Cell lysates were immunoblotted using p- and t-AKT (for IGF-1R); or p- and t-ERK1/2 (bFGF)

The effects of KL1 on IGF-1, bFGF and FGF23 signaling were analyzed (FIG. 17J). Panc1 cells were transfected with DNA encoding for FL-mKL (pCDNA3-HA-KL), for mKL (HA-KL1) or an empty vector, starved for 48 hours, treated with IGF-1 (12.5 nM, 15 min) or bFGF (10 ng/ml), and analyzed using Western blotting for the level of expression and phosphorylation of AKT or ERK1/2.

Results

Klotho Protein Expression in Breast Cancer

Immunochemical staining showed that higher klotho protein expression was noted in all normal breast samples and in 90% of the normal breast samples adjacent to IDC or DCIS, compared to only 17% in DCIS and 22% in IDC (p, 0.0001, FIG. 1, Table 1)

A significant association between klotho protein expression and lower proliferative index, as evaluated by K167 staining occurred (p=0.04, Table 2). A trend was also noted toward an association between no klotho protein expression and smaller tumor size (p=0.08, Table 2).

RT-PCR studies showed that high klotho protein expression was found in the non-malignant cell breast cell line MCF-12A, and in the well-differentiated MDF-7 cells, but that low klotho protein expression was found in the less differentiated cell lines MDA-MB-231, SK-BR3, and T-47D (FIG. 2).

Figure 3A:
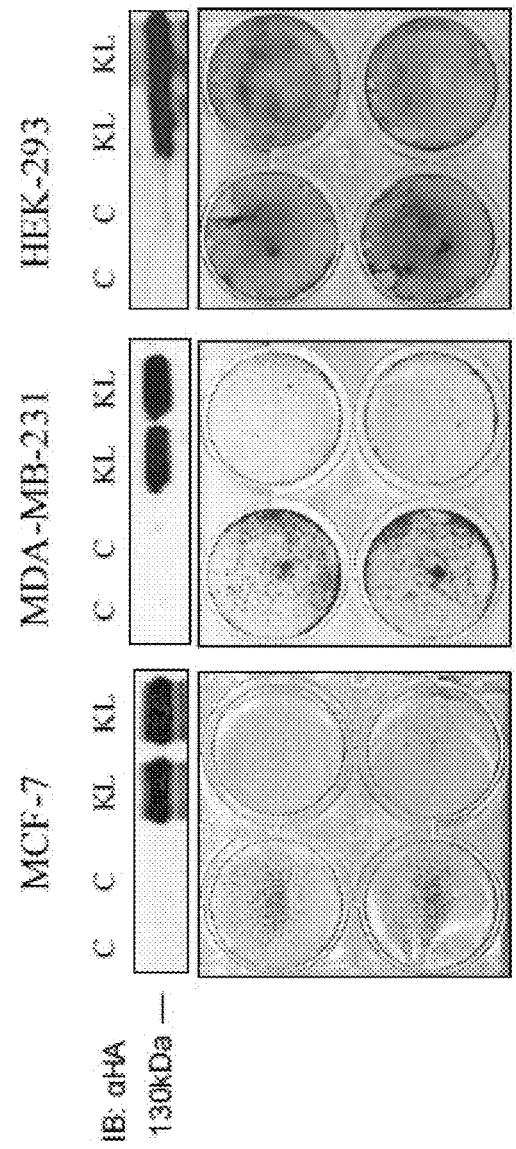
FIG. 3A shows the results of a colony formation assay, in which colonies were stained with crystal violet and photographed.

Transfection assays of the MCF-7 and MDA-MB-231 breast cancer cell lines showed that transient klotho protein upregulation decreased clonal growth of these cells, as measured by colony assays, but did not affect the growth of human embryonic 293 cells. Stable overexpression of klotho protein significantly reduced breast cancer cell proliferation. Klotho protein expression reduced the number and size of surviving colonies of breast cancer cells by 84% and 72% (respectively), compared to empty vector-transfected controls ($p<0.0005$), but had no effect on HEK 293 growth (FIG. 3).

Figure 3B:
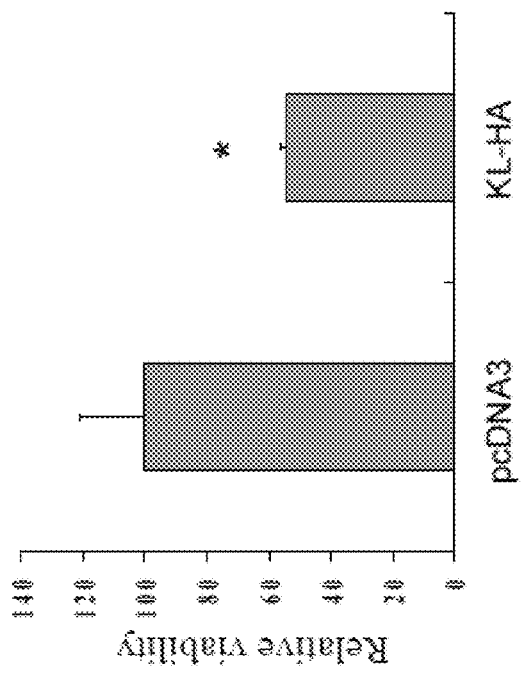
FIG. 3B is a bar chart showing relative viability of stably transfected MCF-7 subclones (KL-HA) and control (pcDNA3)

Proliferation as evaluated by MTT assay was up to 6-fold slower in klotho protein-expressing cells compared to the controls. Results for MCF-7 cells are shown in FIG. 3b.

Analyses of klotho protein mRNA levels following transfection with the various siRNAs revealed 88% reduction of klotho protein expression following transfection with siRNA3 (FIG. 4a). Proliferation of MCF-7 cells, as assessed by MTT assay, increased by 2.5-fold at 48 h following down-regulation of klotho protein using siRNA3, compared to transfection with siRNAc ($p<0.05$, FIG. 4b).

Over-expression of klotho protein was found to reduce p53 levels in HEK 293, but to increase p53 levels in MCF-7 cells (FIG. 5). No changes in expression or cleavage of the apoptosis associated protein polyADP-ribose polymerases (PARP) were noted following klotho protein over-expression of klotho protein in either cell line.

Figures 6A, 6B:
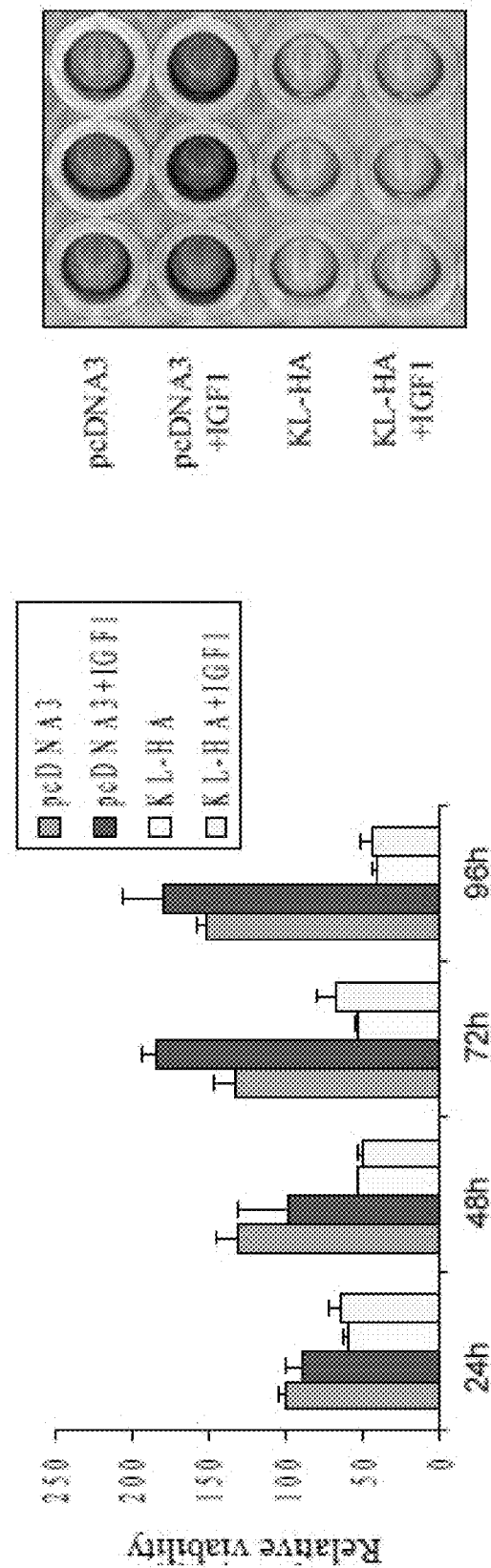
FIG. 6A is a bar chart showing relative viability of MCF-7 cells transfected with either klotho protein expression plasmid (KL-HA) or a control vector (pcDNA3), and treated by IGF-1; (12.5 nM) for the indicated times.
FIG. 6B shows a representative plate of MCF-7 cells, after 96 hr of IGF-1 treatment.

Klotho protein transfection completely inhibited IGF-1 induced cell proliferation in untreated MCF-7 cells, and this inhibition was only minimally restored following addition of IGF-1 to the cells. Thus, while IGF-1 increased by up to 40% cell-proliferation in control pcDNA3-transfected cells, cell proliferation in the HA-KL-transfected cells increased by only 25% (FIGS. 6a and 6b).

As shown in FIG. 7a, maximal activation of the IGF-1/insulin pathway occurred at 15 min of IGF-1 (12.5 nM) and this activation was inhibited in klotho protein over-expressing cells. Klotho protein over-expression in MCF-7 cells was associated with reduced phosphorylation not only of the IGF-1R, but also its downstream targets: IRS-1, AKT1, GSK3β and extracellular signal-regulated kinases (ERK) -1 and -2 (FIG. 7b). Smaller effects were noted in the MDA-MB-231 cells (data not shown), and only minor effects were noted in HEK 293 cells (FIG. 8).

An increased AKT phosphorylation following IGF-1 stimulation in siRNA3 transfected cells was noticed compared to siRNAc transfected cells (FIG. 9a).

The addition of soluble klotho protein inhibited phosphorylation of the IGF-1 receptor, as shown in FIG. 9b.

MCF-7 cells were also treated with a conditioned medium taken from klotho protein-over-expressing cells and found similar results, namely, inhibition of IGF-1 pathway activation (data not shown). These data suggest that the soluble form of klotho protein is a potent inhibitor of the IGF-1 pathway.

Analysis of the effects of over-expression of klotho protein on C/EBPβ levels showed significant up-regulation of C/EBPβ following over-expression of klotho protein in MCF-7 cells, and to a lesser extent in MDA-MB-231 cells, compared to cells transfected with an empty vector (FIG. 8).

Klotho protein inhibited the activation of the insulin pathway in MCF-7 cells but not HEK 293 cells (FIG. 11a). Over-expression of klotho protein affected neither the expression nor phosphorylation of ERK1/2, thus suggesting that the EGF pathway was not affected by over-expression of klotho protein (FIG. 11b).

Klotho Protein Expression in Pancreatic Cancer

Figure 12:
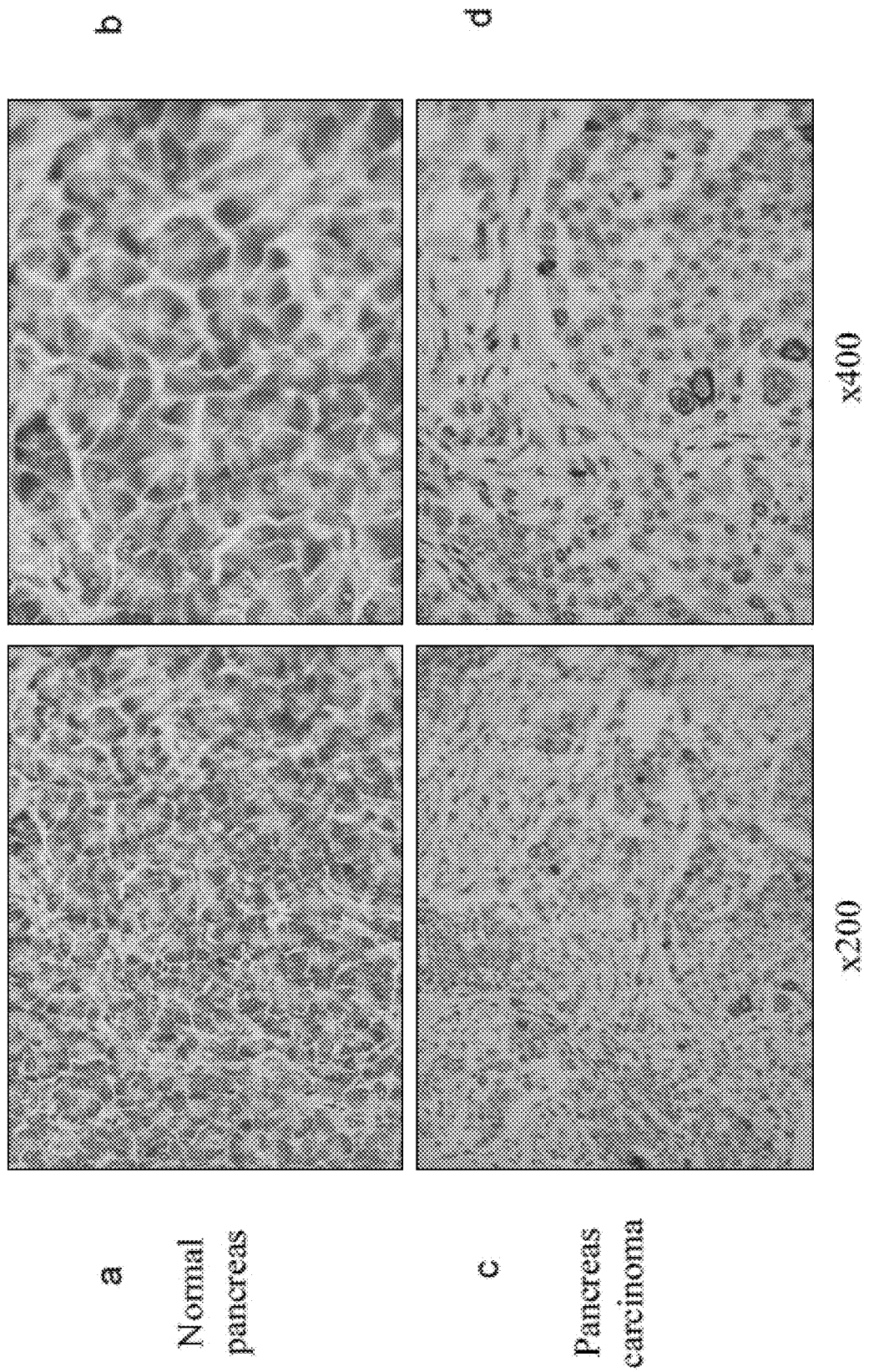
FIG. 12 shows immunohistochemical staining of normal pancreas cells and pancreatic carcinoma, at ×200 and ×400 magnification.

As seen in FIGS. 12a and 12b, at ×200 and ×400 magnification, respectively, immunohistochemical staining revealed the presence of a high level of klotho protein expression in tissue obtained from a normal pancreas. In contrast, as seen in FIGS. 1c and 1d, very low levels of klotho protein expression were seen at ×200 and ×400 magnification, respectively, in tissue derived from a pancreatic carcinoma.

High klotho protein expression was noted in all normal pancreatic samples studied (n=3), but only in 2 out of 12 pancreatic cancer samples. 6 out of 12 carcinoma samples did not express detectable levels of klotho protein and 4 expressed only low levels of klotho protein (see Table 3 below).

Carcinoma cell lines Colo357 and MiaPaCa2 expressed high levels of klotho protein, while Panc1 expressed only low levels of klotho protein.

TABLE 3

|  | Normal (n = 3) | Carcinoma (n = 12) |
|---|---|---|
| High klotho protein (+) | 3 | 2 |
| Weak klotho protein (+/−) | 0 | 4 |
| Undetectable (−) | 0 | 6 |

FIG. 13 presents the results of a colony formation assay, which shows that klotho protein expression significantly reduced the number and size of surviving colonies, as compared to empty-vector transfected colonies.

As seen in FIG. 14, MTT proliferation assay showed that Panc1 cells showed a reduction in viability in response to soluble klotho protein. Treatment with 5 nM caused more than 40% reduction in viability. Moreover, the combination of soluble klotho protein and 5-FU (500 µM) showed additive effect: while 5-FLU alone reduced viability by 50%, the combination reduced viability by 70%.

Animal studies showed that klotho protein treatment of mice resulted in a significant dose-response arrest of tumor growth, as seen in FIG. 15.

Klotho protein over-expression was found to be associated with reduced phosphorylation of the IGF-1R, and its downstream targets: AKT1 and ERK1/2, as shown in FIG. 16a. Similarly, the addition of soluble klotho protein inhibited phosphorylation of all three proteins, as shown in FIG. 16b.

Maximal activation occurred at 15 min of IGF-1 (12.5 nM) and this activation was inhibited in klotho protein over-expressing cells.

Pancreatic Cell Growth Inhibition by KL1

Similar growth inhibitory activities of Panc1 cells were noted for mKL1 and FL-mKL (FIG. 17A).

Reduction of viability of Panc1 cells by 50% was observed following treatment with sol-hKL1 at concentrations 100-times higher than sol-hKL (FIG. 17B. *p<0.005 for comparison between treated and control cells). Data are shown as mean±s.d, of three independent experiments.

Treatment with either sol-hKL or sol-hKL1 significantly inhibited tumor growth following injection of Panc1 cells (FIGS. 17D-F, p<0.05) both in terms of tumor volume and weight. Immunohistochemistry analysis of the proliferation marker Ki67 revealed a significant reduction in the percent of proliferating cells in four tumors harvested from treated mice compared to four controls (50% compared to 70%, p=0.02 FIG. 17G). No changes in weight (FIG. 17C) or general health were noted in mice treated with either sol-hKL or sol-hKL1.

After four weeks of treatment following injection of MiaPaCa2 cells, all the injected tumors were observed in the control group, while two tumors (12%) of the sol-hKL-treated mice and four (25%) of the sol-hKL1-treated mice completely regressed (FIG. 17I). Moreover, sol-hKL1 inhibited tumor growth more effectively than sol-hKL (FIGS. 17H-I).

Figure 17K:
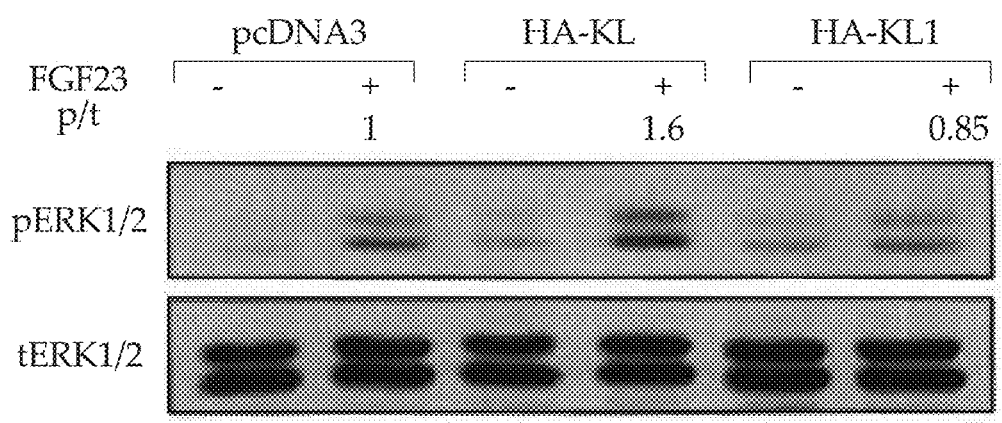
FIG. 17K is an immunoblot of MDCT cells transfected with either klotho protein-HA expression plasmid (KL-HA), KL-1 protein-HA expression plasmid (KL1-HA) or a control vector (pcDNA3) and stimulated p- and t-FGF23. Cell lysates were immunoblotted using p- and t-ERK1/2 and C/EBPβ antibodies.

Treatment with either sol-hKL or sol-hKL1 did not affect blood counts or liver function tests (data not shown). Importantly, sol-hKL but not sol-hKL1, altered blood urea, cholesterol and phosphate levels (Table 4). Glucose levels were determined after fasting in the MiaPaCa2 xenograft experiment. While treatment with sol-hKL mildly increased glucose levels, sol-hKL1 did not have any significant effect on glucose level (Table 4).

mKL1 reduced phosphorylation of AKT and ERK1/2 to a greater extent than FL-mKL (FIG. 17J). However, mKL1 had no effect on the phosphorylation of ERK1/2 following FGF23 stimulation in Mouse Distal Convoluted Tubules (MDCT) cell line (FIG. 17K). Thus, FL-mKL and mKL1 present cell-type and pathway-dependent differential activities.

Discussion

The present inventors have identified, for the first time, tumor suppressor activities for klotho protein in breast cancer. High klotho protein expression was observed in normal breast, while low expression was noted in DCIS and invasive cancer, and re-introduction of klotho protein into breast cancer cells slowed their growth and was associated with inhibited activation of the insulin/IGF pathways and up-regulation of the tumor suppressor C/EBPβ.

Klotho protein is abundantly expressed in the distal convoluted renal tubules and in the choroids plexus in the brain. However, klotho protein is also expressed in various sex-hormone responsive organs including placenta, testis, prostate and ovary (Kuro-o et al., 1997). Thus, its expression in the normal mammary gland could be anticipated. The present analysis was conducted on a relatively large number of breast samples and corroborated staining specificity using well-established negative and positive controls. Moreover, a search of published breast cancer transcriptome profiles, using the Oncomine database (http://www.oncomine.org) further supported these findings and revealed reduced klotho protein expression in breast cancer, and an association between lower expression and adverse tumor characteristics.

The present observation of an association between low klotho protein expression and higher proliferation also indicate a tumor suppressor role for klotho protein in breast cancer. Very low expression of klotho protein was observed both in DCIS and invasive cancers, and preliminary observations indicate reduced klotho protein expression already in ductal hyperplasia (data not shown). These data suggest that loss of klotho protein expression is required in the early stages of breast cancer tumorigenesis. Thus, klotho protein expression pattern may serve as novel prognostic factor in breast cancer, and perhaps may be able to predict cancer development from pre-malignant lesions. However, a much larger number of samples is required in order to elucidate the prognostic significance of klotho protein expression.

Klotho protein is a type I transmembrane protein which localizes at the plasma membrane, as well as in the cytoplasm, where it dimerizes with Na+K+-ATPase in the Golgi apparatus (Imura et al., 2007). In accordance with these data, immunostaining analysis revealed klotho protein expression both in the plasma membrane and the cytoplasm. However, klotho protein may also be shed and act as a circulating hormone (Chen et al., 2007).

The present inventors have identified inhibition of the IGF-1 pathway following either klotho protein over-expression in breast cancer cells, treatment of the cells with a soluble form of klotho protein or treatment of the cells with a condition medium taken from klotho protein over-expressing cells. Thus, klotho protein activities in the mammary gland may be mediated not only by expression within the cells but also through shedding of soluble klotho protein and a paracrine effect on surrounding cells. However, as klotho protein expression is lost only in DCIS or invasive cancers, and not in the adjacent normal mammary tissue, and as soluble klotho protein inhibits the growth of breast cancer cells in vitro, we hypothesize that even if a soluble form of klotho protein is excreted from the normal mammary cells, it either does not reach the tumor cells or is inactivated within the tumor, or its concentration is not sufficient to affect the nearby cancer cells.

Activity of the IGF-1R and the IR, and their down-stream signaling components, including IRS-1, Grb2, shc, PI-3K and AKT has been associated with breast cancer tumorigenesis. Moreover, specific IGF-1R inhibitors show anti-tumoral effects against breast cancer (Haluska et al., 2006; Mitsiades et al., 2004). Thus, loss of klotho protein-mediated inhibition of the insulin/IGF-1 pathways may serve as a novel mechanism involved in breast cancer tumorigenesis. Importantly, while klotho protein has been shown previously to inhibit activation of the IGF-1R without altering IGF-1R ability to bind IGF-1 (Kurosu et al., 2005), the present inventors have shown for the first time, a direct interaction between klotho protein and the IGF-1R. The mechanism by which klotho protein inhibits IGF-1 signaling however needs to be further explored.

Several lines of evidence suggest a growth inhibitory role for the transcription factor C/EBPβ in breast cancer tumorigenesis. C/EBPβ inhibits proliferation of breast cancer cells through up-regulation of 15-PGDH, the major prostaglandin catabolic enzyme, mediates TGF cytostatic response in metastatic breast cancer, and plays an important role in oncogene induced senescence (Gery et al., 2005; Gomis et al., 2006; Wolf et al., 2006a). Interestingly, C/EBPβ may serve as a link between klotho protein, the insulin/IGF-1 pathways and breast cancer growth inhibition. C/EBPβ is involved in klotho protein signaling and is up-regulated during klotho protein-induced adipocyte differentiation (Chihara et al., 2006). Moreover, the IGF-1 pathway can negatively regulate C/EBPβ by phosphorylation of GSK3β that leads to C/EBPβ down-regulation (Li et al., 2007). Our observation of C/EBPβ up-regulation following klotho protein over-expression suggests a role for the interaction between klotho protein, the IGF-1 pathway and C/EBPβ in breast cancer tumorigenesis.

A striking cell-type dependent klotho protein activity was observed. In MCF-7 cells, klotho protein reduces clonogenic proliferation, increases p53 expression, inhibits the insulin/IGF-1 pathways and increases the response to bFGF (data not shown), while the opposite effects are observed in the non-cancerous HEK 293 cells. Moreover, over-expression of klotho protein in vascular endothelial cells down-regulates p53 and reduces apoptosis and senescence (Ikushima et al., 2006), while its silencing in human primary fibroblasts up-regulates p53 and induces premature senescence (de Oliveira, 2006). Thus, the effects observed by the present inventors in breast cancer cells are opposite to the effects observed in various non-cancerous cells. Interestingly, differential growth inhibition has been shown recently following EGF pathway inhibition, which reduced breast cancer cell proliferation but enhanced myocyte growth (Spector et al., 2007). This phenomenon was attributed to the ability of normal myocytes to overcome stress by increasing their oxidative activity, compared to the cancer cells, which show only glycolytic activity. Perhaps similar mechanisms may also be involved in the differential response to over-expression of klotho protein and IGF-1 pathway inhibition. As klotho protein has been shown to play a role in cellular response to oxidative stress activities (Yamamoto et al., 2005), as well as in glucose metabolism (Utsugi et al., 2000), this hypothesis should be further explored.

In summary, the present inventors have identified klotho protein, for the first time, as a tumor suppressor gene in breast cancer and as a modulator of the IGF-1 pathway in breast cancer cells. As klotho protein is expressed in various sex hormone responsive organs, and as klotho protein may also serve as a circulating hormone, its role in the pathogenesis of other malignant diseases should also be explored.

Only full length klotho protein (FL-KL) can function as a co-receptor for FGF23 (Kurosu et al., 2006; Wu et al., 2008). Indeed, KL1 did not affect signaling by FGF23 in MDCT cells (FIG. 1K). Accordingly, hypophosphatemia, which may be attributed to the activity of FGF23, was observed in mice treated with FL-KL, but not in mice treated with KL1. These data are supported by a recent clinical observation, where genetic overexpression of Klotho protein in a young girl resulted in hypophosphatemia attributed to abnormal regulation of FGF23 signaling (Brownstein et al., 2008). On the other hand, each of KL1 or KL2 can independently regulate cell-surface expression of TRPV5 and ROMK ion channels (46, 47), and the present inventors show here, for the first time, that KL1 is a potent inhibitor of bFGF and IGF-1 signaling. Taken together, these observations imply differential activities of FL-KL and KL1 toward different signaling pathways and in different cell lines. While KL1 is as effective as FL-KL for the treatment of cancer, KL1 has fewer other biological effects and therefore an improved safety profile.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention.

To the extent that section headings are used, they should not be construed as necessarily limiting.

REFERENCES

Arking D E. Becker D M, Yanek L R, Fallin D, Judge D P, Moy T F, et al. (2003). KLOTHO allele status and the risk of early-onset occult coronary artery disease. *Am J Hum Genet* 72: 1154-1161.

Arking D E, Krebsova A, Macek M Sr., Macek M Jr, Arking A, Mian I S, et al. (2002). Association of human aging with a functional variant of klotho. *Proc Natl Acad Sci USA* 99: 856-861.

Bartucci M. Morelli C, Mauro L, Ando' S. Sunlacz E. (2001). Differential Insulin-like Growth Factor I Receptor Signaling and Function in Estrogen Receptor (ER)-positive MCF-7 and ER-negative MDA-MB-231 Breast Cancer Cells. *Cancer Res* 61: 6747-6754.

Bergmann U et al. (1995). Insulin-like growth factor I overexpression in human pancreatic cancer: evidence for autocrine and paracrine roles. *Cancer Res.* 15: 55(10): 2007-11.

Brownstein C A, Adler F. Nelson-Williams C, Iijima J, Li P, Imura A. et al. (2008). A translocation causing increased alpha-klotho level results in hypophosphatemic rickets and hyperparathyroidism. *Proc Natl Acad Sci USA*. 105: 3455-60.

Chen C-D, Podvin S, Gillespie E, Leeman S E, Abraham C R. (2007). Insulin stimulates the cleavage and release of the extracellular domain of Klotho by ADAM10 and ADAM17. *Proc Natl Acad Sci USA* 104: 19796-19801.

Chihara Y, Rakugi I H, Ishikawa K, Ikushima M, Maekawa Y, Ohta J, et al. (2006). Klotho protein promotes adipocyte differentiation. *Endocrinology* 147: 3835-3842.

de Oliveira R M (2006). Klotho RNAi induces premature senescence of human cells via a p53/p21 dependent pathway. *FEBS Lett* 580: 5753-5758.

Edderkaoui M et al. Insulin-like growth factor-1 receptor mediates the prosurvival effect of fibronectin.

El-Shewy H M, Lee M-H, Obeid L M, Jaffa A A, Luttrell L M. (2007). The Insulin-like growth factor type 1 and insulin-like growth factor type 2/mannose-6-phosphate receptors independently regulate ERK1/2 activity in HEK293 cells. *J Biol Chem* 282: 26150-26157.

Geier A, Beery R, Haimsohn M, Karasik A. (1995). Insulin-like growth factor-1 inhibits cell death induced by anti-cancer drugs in the MCF-7 cells: involvement of growth factors in drug resistance. *Cancer Invest* 13: 480-486.

Gery S, Tanosaki S, Bose S, Bose N, Vadgama J, Koeffler H P. (2005). Down-regulation and growth inhibitory role of C/EBP{alpha} in breast cancer. *Clin Cancer Res* 11: 3184-3190.

Gomis R R, Alarcon C, Nadal C, Van Poznak C, Massague J. (2006). C/EBP[beta] at the core of the TGF[beta] cytostatic response and its evasion in metastatic breast cancer cells. *Cancer Cell* 10: 203-214.

Haimsohn M, Beery R, Karasik A, Kanety H, Geier A. (2002). Aurintricarboxylic acid induces a distinct activation of the IGF-I receptor signaling within MDA-231 Cells. *Endocrinology* 143: 837-845.

Haluska P, Carboni J M, Loegering D A, Lee F Y, Wittman M, Saulnier M G, et al. (2006). In vitro and in vivo antitumor effects of the dual insulin-like growth factor-I/insulin receptor inhibitor, BMS-554417. *Cancer Res* 66: 362-371.

Ikushima M, Rakugi H, Ishikawa K, Maekawa Y, Yamamoto K, Ohta J. (2006). Anti-apoptotic and anti-senescence effects of Klotho on vascular endothelial cells. *Biochem Biophys Res Commun* 339: 827-832.

Imura A, Iwano A, Tohyama O, Tsuji Y, Nozaki K, Hashimoto N, et al. (2004). Secreted Klotho protein in sera and CSF: implication for post-translational cleavage in release of Klotho protein from cell membrane. *FEBS Lett* 565: 143-147.

Imura A, Tsuji Y, Murata M, Maeda R, Kubota K, Iwano A, et al. (2007) {alpha}-Klotho as a Regulator of Calcium Homeostasis. *Science* 316: 1615-1618.

Ito S, Kinoshita S, Shiraishi N, Nakagawa S, Sekine S, Fujimori T, et al. (2000). Molecular cloning and expression analyses of mouse [beta]klotho, which encodes a novel Klotho family protein. *Mech Dev* 98: 115-119.

Jonsson E, Fridborg H, Nygren P, Larsson R. (1998). Synergistic interactions of combinations of toptecan with standard drugs in primary cultures of human tumor cells from patients. *Eur J Clin Pharmacol* 54: 509-14.

Karna E et al. Serum and tissue level of insulin-like growth factor-I (IGF-I) and IGF-I binding proteins as an index of pancreatitis and pancreatic cancer. Int J Exp Pathol. 2002 October; 83(5):239-45.

Kato Y, Arakawa E, Kinoshita S, Shirai A, Furuya A, Yamano K, et al. (2000). Establishment of the anti-klotho monoclonal antibodies and detection of klotho protein in kidneys. *Biochem Biophys Res Commun* 267: 597-602.

Kim Y, Kim J-H, Nam Y J, Kong M, Kim Y J, Yu K-H, et al. (2006). Klotho is a genetic risk factor for ischemic stroke caused by cardioembolism in Korean females. *Neurosci Lett* 407: 189-194.

Kuro-o M, Matsumura Y, Aizawa H, Kawaguchi H, Suga T, Utsugi T, et al. (1997). Mutation of the mouse klotho gene leads to a syndrome resembling ageing. *Nature* 390: 45-51.

Kurosu H, Ogawa Y, Miyoshi M, Yamamoto M, Nandi A, Rosenblatt K P, et al. (2006). Regulation of fibroblast growth factor-23 signaling by klotho. *J Biol Chem* 281: 6120-6123.

Kurosu H et al. Suppression of aging in mice by the hormone Klotho. *Science*. 2005 Sep. 16; 309(5742):1829-33. J Biol Chem. 2007 Sep. 14; 282(37):26646-55.

Kurosu H, Yamamoto M. Clark J D, Pastor J V, Nandi A, Gurnani P, et al. (2005). Suppression of aging in mice by the hormone klotho. *Science* 309: 1829-1833.

Lacroix M, Leclercq G. (2004). Relevance of breast cancer cell lines as models for breast tumours: an update. *Breast Cancer Res Treat* 83: 249-289.

Li X, Kim J W, Gronborg M. Urlaub H, Lane M D, Tang Q-Q. (2007). Role of cdk2 in the sequential phosphorylation/activation of C/EBPbeta during adipocyte differentiation. *Proc Natl Acad Sci* (USA 104: 11597-11602.

Matsumura Y, Aizawa H, Shiraki-Iida T, Nagai R, Kuro-o M, Nabeshima Y-i. (1998). Identification of the human klotho gene and its two transcripts encoding membrane and secreted klotho protein. *Biochem Biophys Res Commun* 242: 626-630.

Mitsiades C S, Mitsiades N S, McMullan C J, Poulaki V, Shringarpure R, Akiyama M, et al. (2004). Inhibition of the insulin-like growth factor receptor-1 tyrosine kinase activity as a therapeutic strategy for multiple myeloma, other hematologic malignancies, and solid tumors. *Cancer Cell* 5: 221-230.

Ohyama Y, Kurabayashi M, Masuda H, Nakamura T, Aihara Y, Kaname T, et al. (1998). Molecular cloning of rat klotho cDNA: markedly decreased expression of klotho by acute inflammatory stress. *Biochem Biophys Res Commun* 251: 920-925.

Shiraki-Iida T, Aizawa H, Matsumura Y, Sekine S, Iida A, Anazawa H, et al. (1998). Structure of the mouse klotho gene and its two transcripts encoding membrane and secreted protein. *FEBS Lett* 424: 6-10.

Spector N L, Yarden Y, Smith B, Lyass L, Trusk P, Pry K, et al. (2007). Activation of AMP-activated protein kinase by human EGF receptor 2/EGF receptor tyrosine kinase inhibitor protects cardiac cells. *Proc Natl Acad Sci USA* 104: 10607-10612.

Urakawa I, Yamazaki Y, Shimada T, Iijima K, Hasegawa H, Okawa K, et al. (2006). Klotho converts canonical FGF receptor into a specific receptor for FGF23. *Nature* 444: 770-774.

Utsugi T, Ohno T, Ohyama Y, Uchiyama T, Saito Y, Matsumura Y. et al. (2000). Decreased insulin production and increased insulin sensitivity in the klotho mutant mouse, a novel animal model for human aging. *Metabolism* 49: 1118-1123.

Wolf I, Bose S, Williamson E A, Miller C W, Karlan B Y, Koeffler H P. (2007). FOXA1: Growth inhibitor and a favorable prognostic factor in human breast cancer. *Int J Cancer* 120: 1013-1022.

Wolf I, Levanon-Coheen S, Bose S, Ligumsky H, Sredni B, Kanety H, et al. (2008). Klotho: a tumor suppressor and a modulator of the IGF-1 and FGF pathways in human breast cancer. *Oncogene* 27: 7094-105.

Wolf I, O'Kelly J, Rubinek T, Tong M, Nguyen A, Lin B T, et al. (2006a). Hydroxyprostaglandin dehydrogenase is a tumor suppressor of human breast cancer. *Cancer Res* 66: 7818-7823.

Wolf I, Sadetzki S, Gluck I, Obermnan B, Ben-David M, Papa M Z, et al. (2006b). Association between diabetes mellitus and adverse characteristics of breast cancer at presentation. *Eur J Cancer* 42: 1077-1082.

Wu X, Lemon B, Li X, Gupte J, Weiszmann J, Stevens J, et al. (2008). C-terminal tail of FGF19 determines its specificity towards Klotho co-receptors. *J Biol Chem* 283: 33304-9.

Yamamoto M, Clark J D, Pastor J V, Gurnani P, Nandi A, Kurosu H, et al. (2005). Regulation of oxidative stress by the anti-aging hormone klotho. *J Biol Chem* 280: 38029-38034.

Yee D. (2006). Targeting insulin-like growth factor pathways. *Br J Cancer* 94: 465-468.

Zarrabeitia M, Hernandez J, Valero C, Zarrabeitia A, Ortiz F, Gonzalez-Macias J, et al. (2007). Klotho gene polymorphism and male bone mass. *Calcif Tissue Int* 80: 10-14.

What is claimed is:

1. A method of treatment by inhibiting tumor growth or reducing tumor size in a subject having cancer, comprising administering to a subject in need thereof a pharmaceutically effective amount of a composition comprising an isolated polypeptide consisting of an amino acid sequence having at least 80% homology to the amino acid sequence represented by SEQ ID NO: 2, or a DNA encoding therefor, wherein the pharmaceutically effective amount is effective in inhibiting tumor growth or reducing tumor size in the patient.

2. The method of claim 1, wherein said cancer is an IGF-1 dependent cancer.

3. The method of claim 1, wherein said cancer is selected from the group consisting of colon cancer, prostate cancer, lung cancer, cervical cancer and ovarian cancer.

4. The method of claim 1, wherein said cancer is breast cancer.

5. The method of claim 1, wherein said cancer is pancreatic cancer.

6. The method of claim 1, wherein said DNA encoding said polypeptide is provided inserted in a recombinant vector suitable for gene therapy.

7. The method of claim 6, wherein said homology is at least 90%.

8. The method of claim 1, further comprising co-administration of a chemotherapeutic agent.

* * * * *